(12) United States Patent
Sung et al.

(10) Patent No.: US 8,187,571 B1
(45) Date of Patent: *May 29, 2012

(54) PHARMACEUTICAL COMPOSITION OF NANOPARTICLES

(75) Inventors: Hsing-Wen Sung, Hsinchu (TW); Hosheng Tu, Newport Beach, CA (US)

(73) Assignees: GP Medical, Inc., Newport Beach, CA (US); National Tsing Hua University, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/928,878

(22) Filed: Dec. 22, 2010

Related U.S. Application Data

(63) Continuation-in-part of application No. 11/975,279, filed on Oct. 18, 2007, now Pat. No. 7,985,426, which is a continuation-in-part of application No. 11/328,552, filed on Jan. 10, 2006, now Pat. No. 7,304,045, which is a continuation-in-part of application No. 10/958,864, filed on Oct. 5, 2004, now Pat. No. 7,348,026.

(51) Int. Cl.
*A61K 51/00* (2006.01)

(52) U.S. Cl. ................................. 424/1.73; 424/1.69
(58) Field of Classification Search ................ 424/1.69, 424/1.73
See application file for complete search history.

(56) References Cited

U.S. PATENT DOCUMENTS
6,726,934 B1   4/2004   Prokop

OTHER PUBLICATIONS

Selvin PR, "The renaissance of fluorescence resonance energy transfer" Natural Structural Biology 2000;7(9):730-734.
Zhang J et al, "Self-assembled nanoparticles based on hydrophobically modified chitosan as carriers for doxorubicin" Nanomedicine: Nanotechnology, Biology and Medicine 2007;3:258-265.
Chiu YL et al, "The characteristics, cellular uptake and intracellular trafficking of nanoparticles made of hydrophobically-modified chitosan" Journal of Controlled Release 2010;146:152-159.
Janes KA et al., "Chitosan nanoparticles as delivery systems for doxorubicin" Journal of Controlled Release 2001;73:255-267.

*Primary Examiner* — Maryam Monshipouri

(57) ABSTRACT

The invention discloses a pharmaceutical composition of nanoparticles, wherein each nanoparticle comprises N-palmitoyl chitosan that is conjugated with at least two different moieties, the moieties including a donor moiety and an acceptor moiety having a distance of 10 nm or less enabling Förster resonance energy transfer.

17 Claims, 30 Drawing Sheets

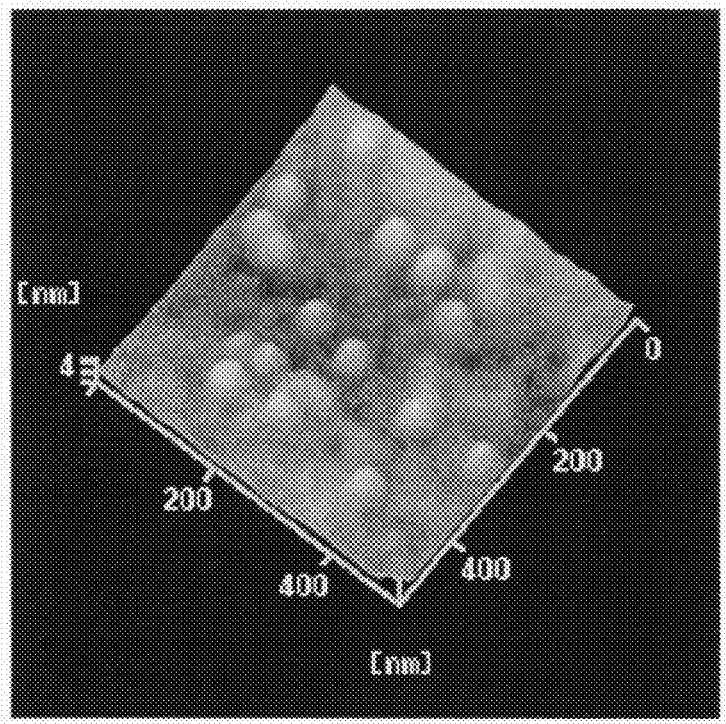
(A) P/C = 0/10
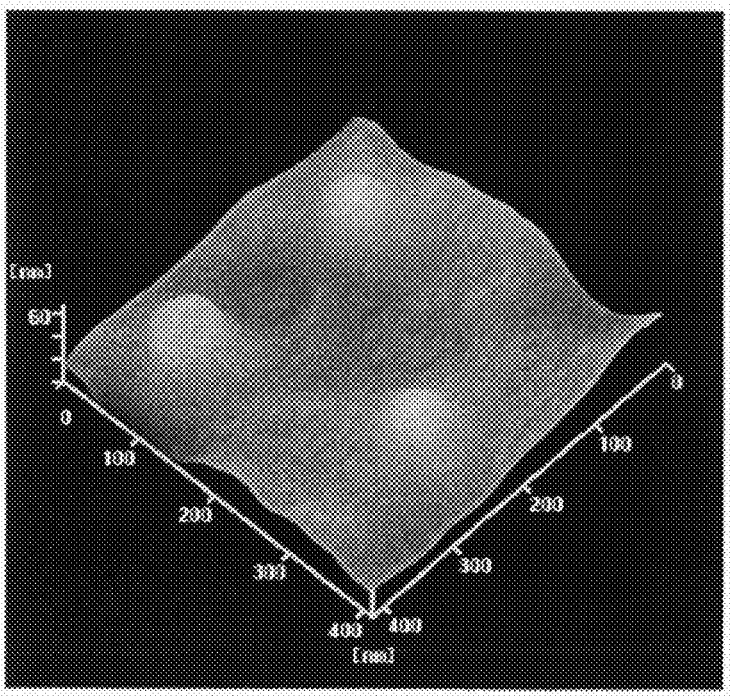
(B) P/C = 0.5/10
FIG. 4

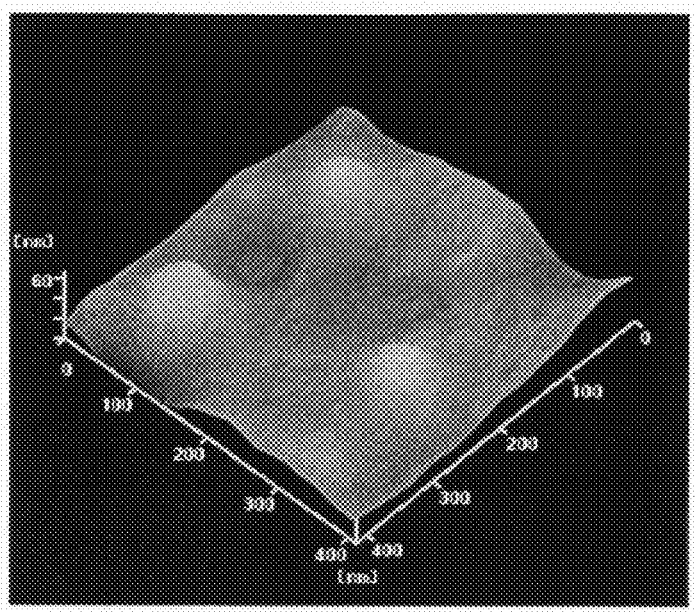
(C) P/C = 2/10
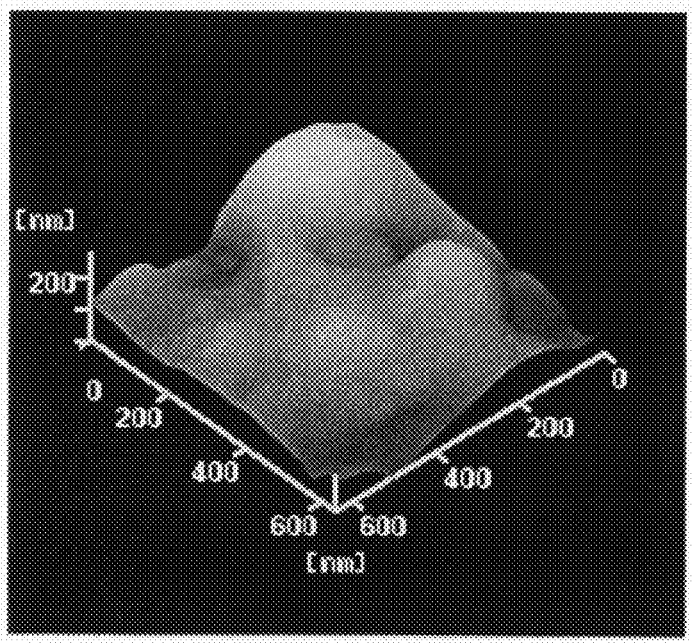
(D) P/C = 3/10
FIG. 4 (continued)

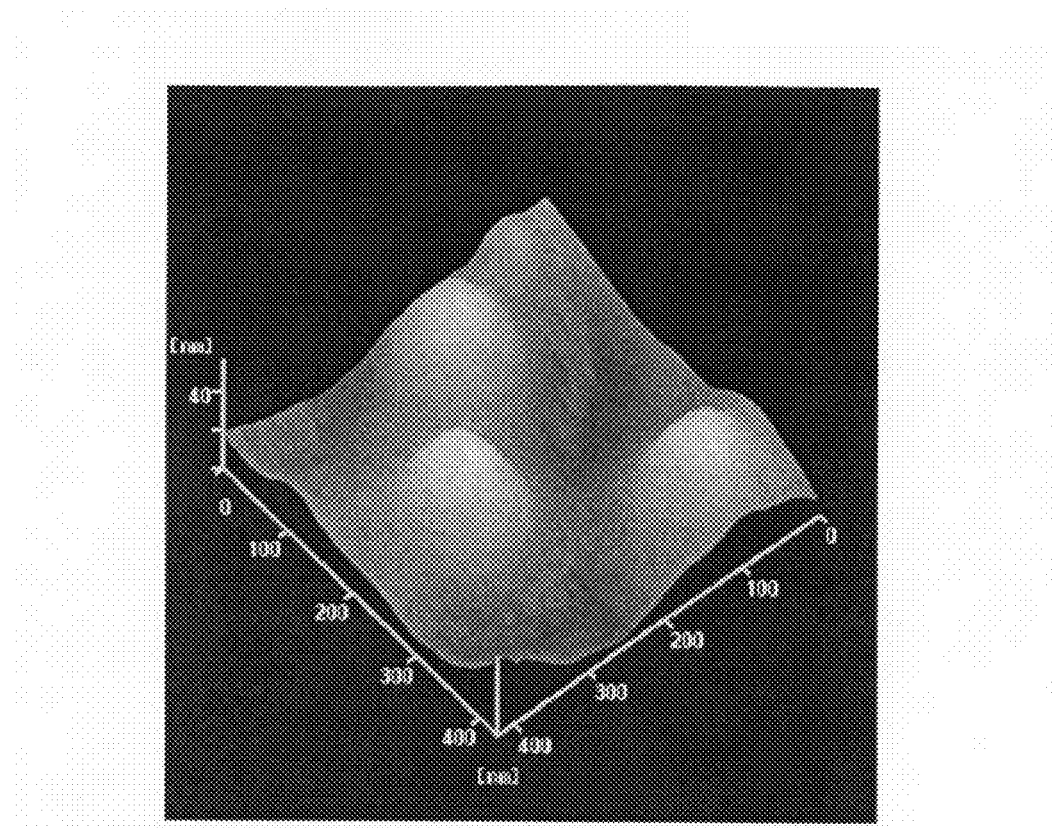
(E) P/C = 1/10
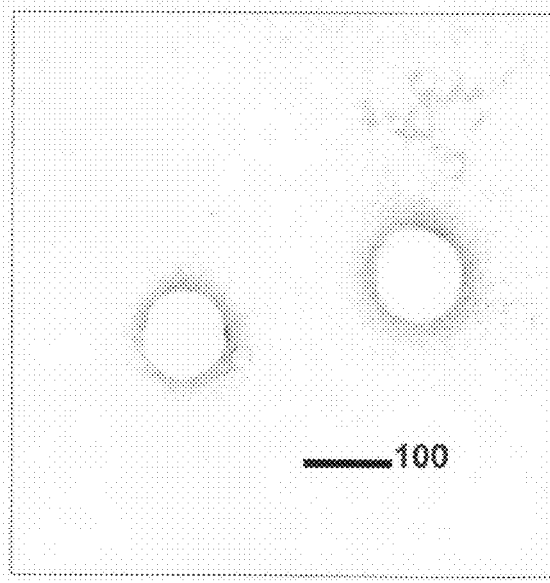
(F) P/C = 1/10
FIG. 4 (continued)

FIG. 7
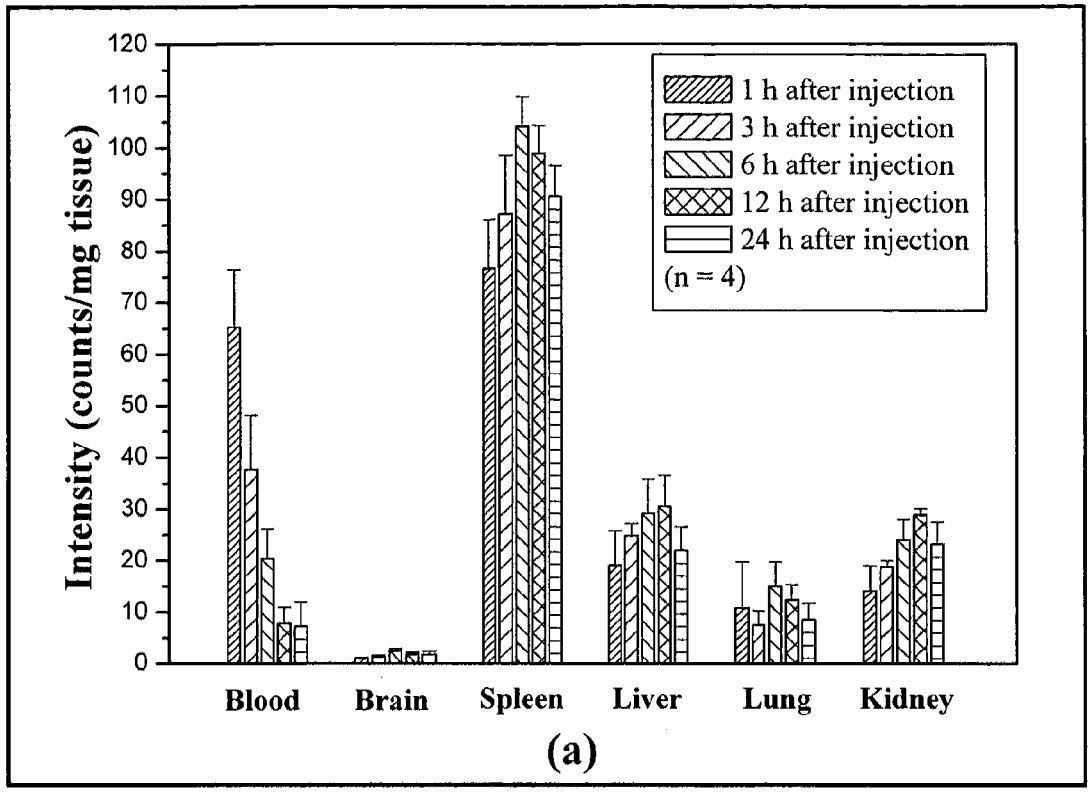
(a)
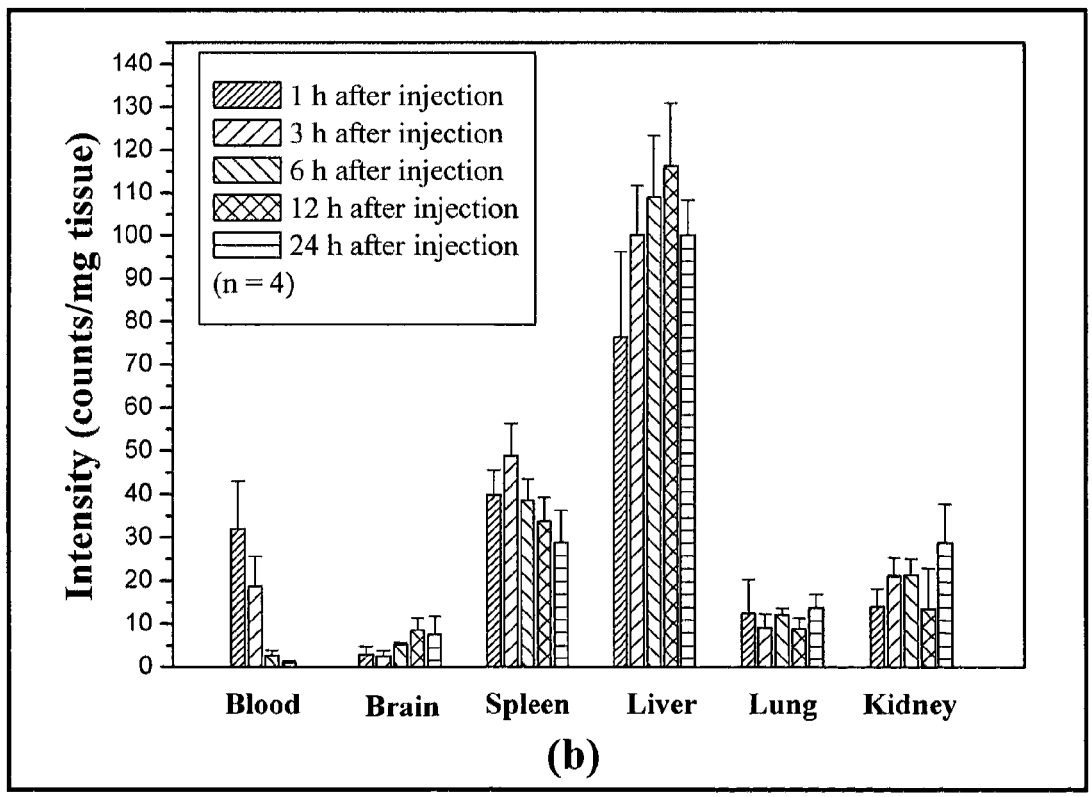
(b)

FIG. 8
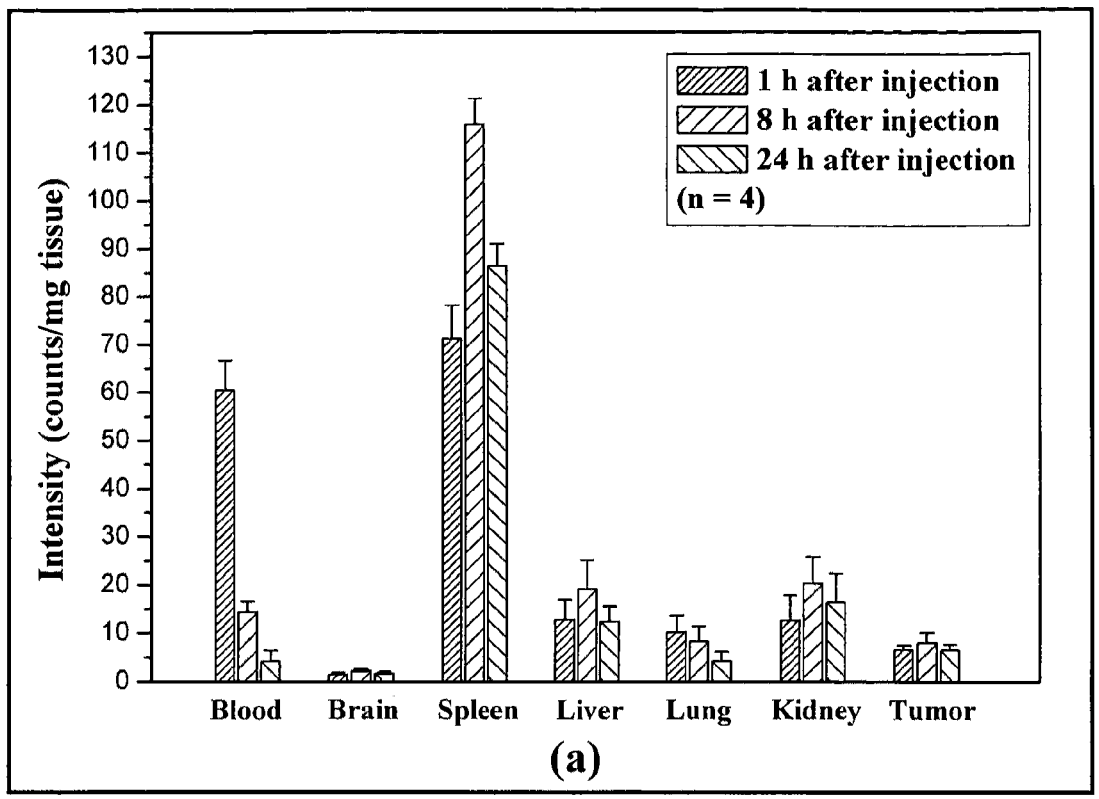
(a)
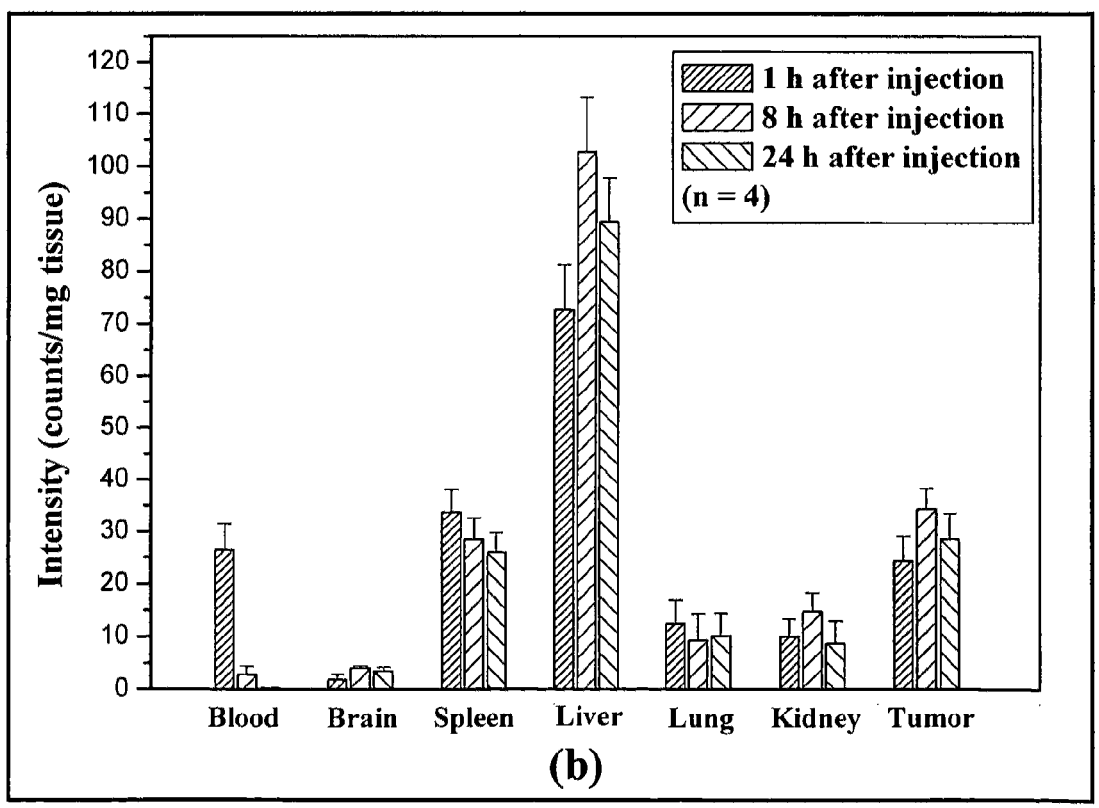
(b)

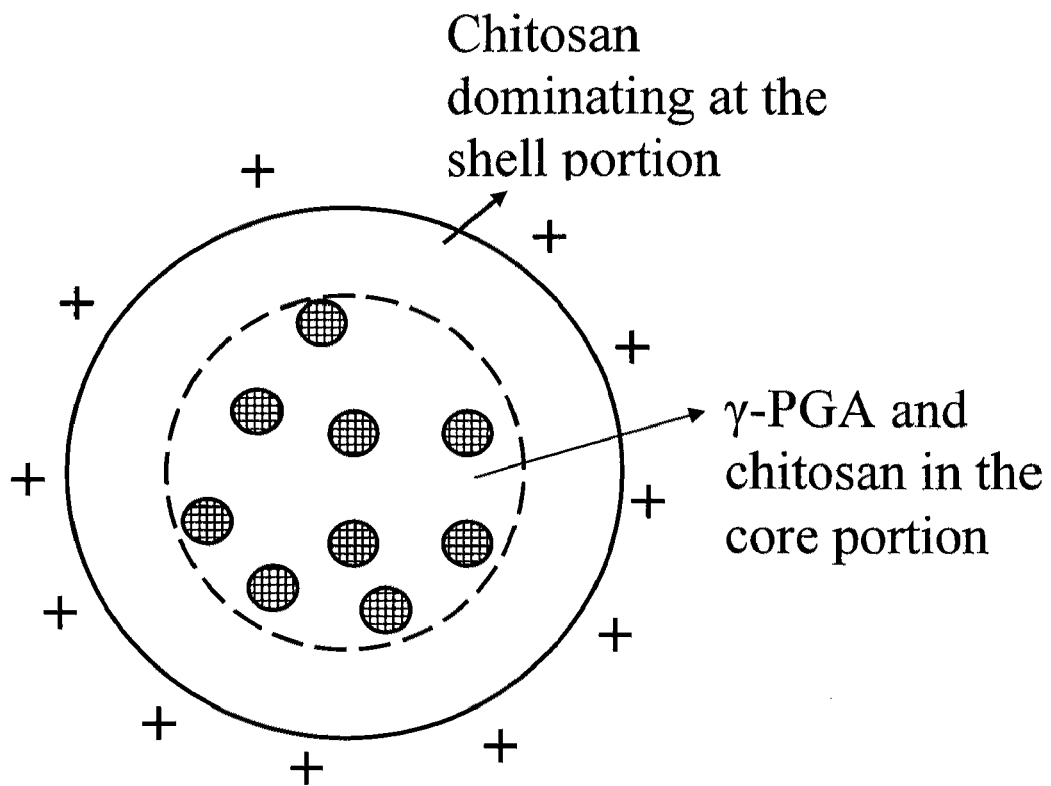
Note: The symbol  denotes a liposome micelle that contains at least one thermal triggered phase-transition compound within the micelle
FIG. 15

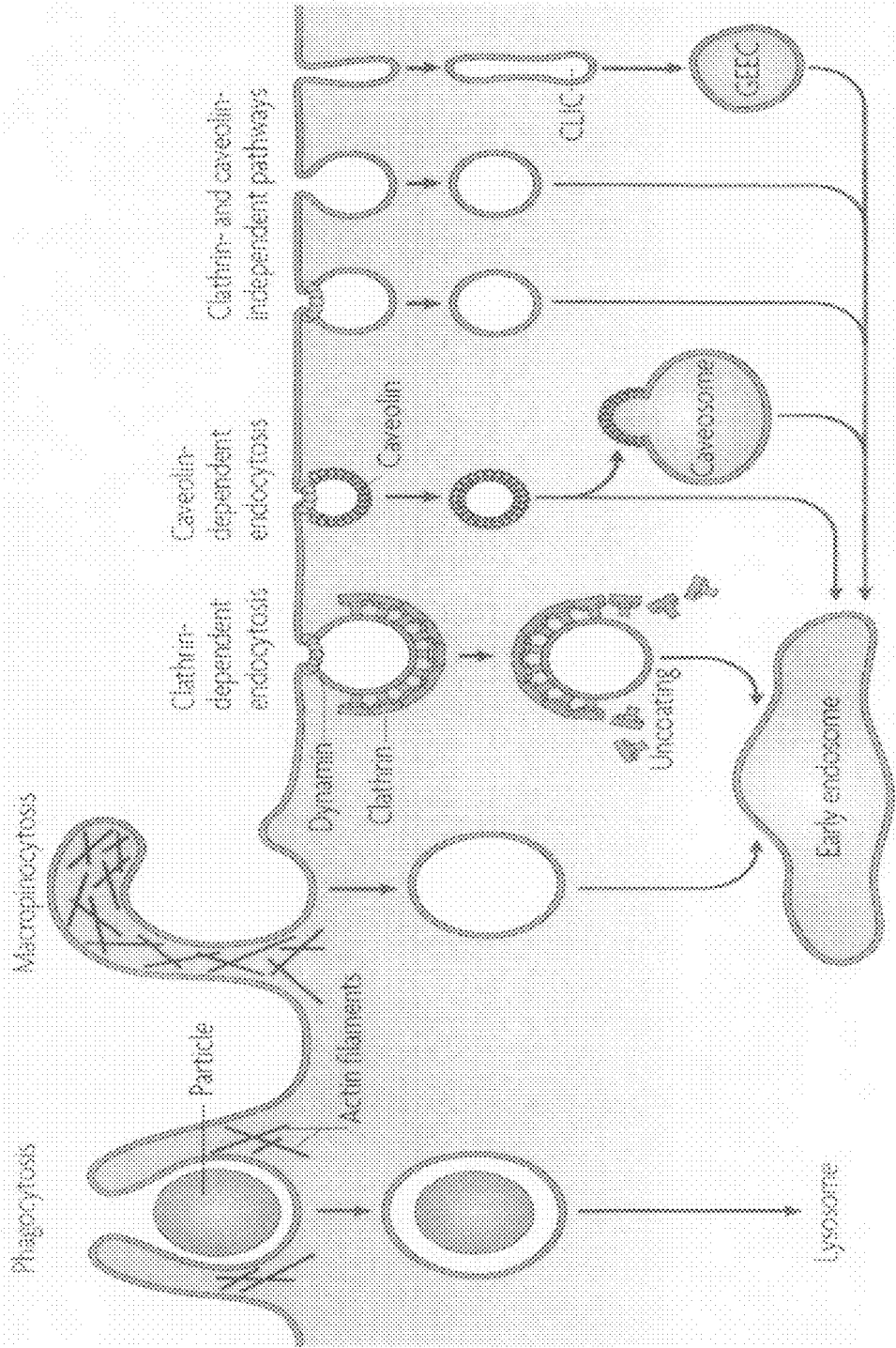
FIG. 19 Endocytosis pathway

FIG 20a
Chemical Structures
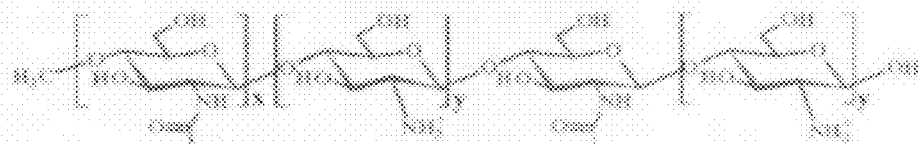
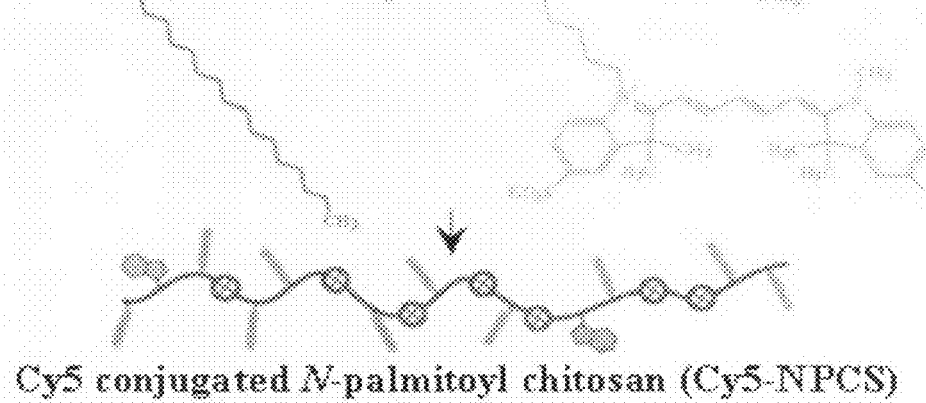
Cy5 conjugated N-palmitoyl chitosan (Cy5-NPCS)
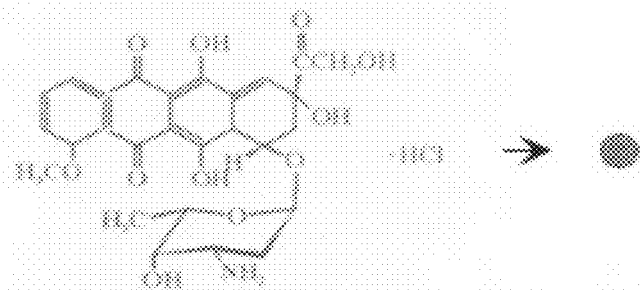
Doxorubicin hydrochloride (DOX)
*in aqueous environment*
*self-assembly of DOX-loaded Cy5-NPCS NPs*
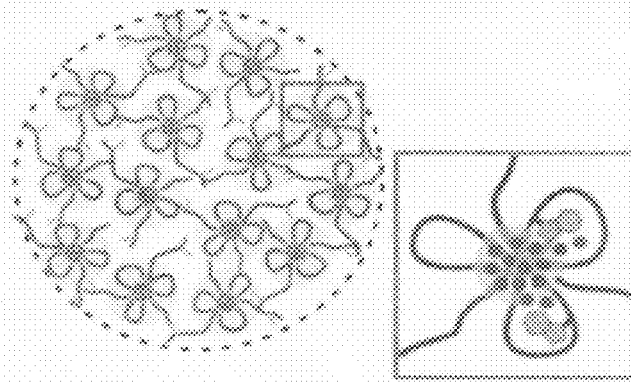 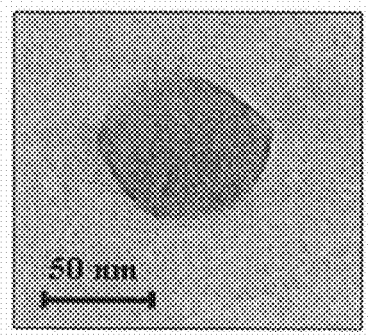
TEM image

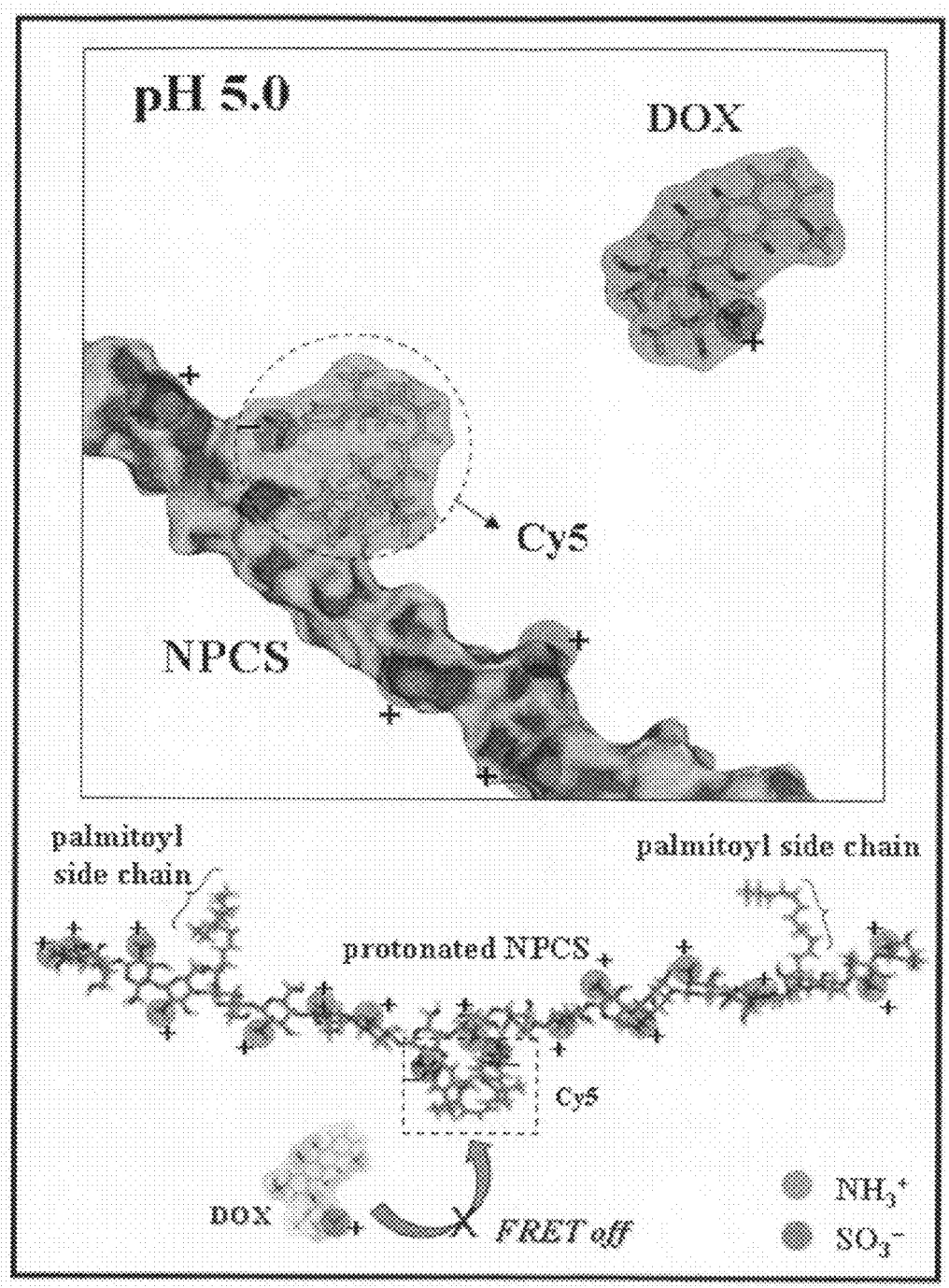

PHARMACEUTICAL COMPOSITION OF NANOPARTICLES

CROSS-REFERENCE TO RELATED APPLICATIONS

This application is a continuation-in-part application of U.S. patent application Ser. No. 11/975,279 filed Oct. 18, 2007, now U.S. Pat. No. 7,985,426, which is a continuation-in-part application of U.S. patent application Ser. No. 11/328,552 filed Jan. 10, 2006, now U.S. Pat. No. 7,304,045, which is a continuation-in-part application of U.S. patent application Ser. No. 10/958,864 filed Oct. 5, 2004, now U.S. Pat. No. 7,348,026, the entireties of the priority documents are hereby incorporated by reference.

FIELD OF THE INVENTION

The present invention is related to a pharmaceutical composition of nanoparticles and methods of intracellularly monitoring/imaging the release of an anticancer agent, doxorubicin from pH-responsive nanoparticles using Förster resonance energy transfer.

BACKGROUND OF THE INVENTION

Chemotherapy for cancers is usually limited by the toxicity of drugs to normal tissues. Additionally, short circulation half-life in plasma, limited aqueous solubility, and non-selectivity are usually encountered by most of the currently available anticancer drugs and thus restrict their therapeutic efficacy (Adv. Drug Deliver. Rev. 2002; 54:695-713). To reduce the toxicity and increase the therapeutic efficacy of anticancer drugs, various drug carriers, such as soluble polymers, polymeric nanoparticles, liposomes, and microspheres have been investigated (J. Control. Release 2000; 69:225-236; J. Control. Release 2003; 92:49-67; J. Biomed. Mater. Res. 2003; 65A:271-282). The hydrophilic shell-forming block determines surface properties of the nanoparticles and influences interactions between the surrounding environments and the nanoparticles (Biomaterials 2003; 24:2053-2059).

Nanoparticles may be delivered to specific sites by size-dependant passive targeting or by active targeting (Cancer Res. 1986; 46:6387-6392; J. Control. Release 1999; 62:253-262). To obtain a high degree of selectivity to a specific organ and to enhance the uptake of drug-loaded nanoparticles into the target cells, active targeting has been attempted. Liver has been one of the most desirable target organs in the body due to various liver-related metabolic and infectious diseases and cancers (Int. J. Pharm. 1999; 188:39-47). The asialoglycoprotein (ASGP) receptor is known to be present on hepatocytes and several human hepatoma cell lines (Adv. Drug Deliver. Rev. 1989; 4:49-63). Therefore, liver targeting is achieved by designing drug delivery systems conjugated with a ligand that can bind to the ASGP receptors.

Poly(lactide) (PLA), poly($\epsilon$-caprolactone) (PCL), poly($\beta$-benzyl L-aspartate) (PLBA), and poly($\gamma$-benzyl L-glutamate) (PLBG) have been used mostly for the core-forming hydrophobic segment of nanoparticles (J. Control. Release 2004; 94:323-335). On the other hand, poly(ethylene oxide) (PEO), a non-toxic and highly hydrated polymer, has been used as the outer shell segment of nanoparticles because of its superior biocompatibility (J. Control. Release 2004; 94:323-335). In one embodiment of the present invention, PLA was used for the hydrophobic segment of the block copolymer, while a natural compound [poly($\gamma$-glutamic acid), $\gamma$-PGA], produced as capsular substance or as slime by members of the genus *Bacillus*, was used as the hydrophilic segment.

$\gamma$-PGA is unique in that it is composed of naturally occurring L-glutamic acid linked together through amide bonds rather than a nondegradable C—C backbone such as PEO. It was reported that this naturally occurring $\gamma$-PGA is a water-soluble, biodegradable, and non-toxic polymer (Crit. Rev. Biotechnol. 2001; 21:219-232). A related, but structurally different, polymer poly($\alpha$-glutamic acid), ($\alpha$-PGA) is usually synthesized from poly($\gamma$-benzyl-L-glutamate) by removing the benzyl protecting group with the use of hydrogen bromide (Adv. Drug Deliver. Rev. 2002; 54:695-713). Li et al. conjugated paclitaxel onto $\alpha$-PGA via covalent bonding to form a new drug formulation (Cancer Res. 1998; 58:2404-2409). Their pre-clinical data suggested that the uptake of $\alpha$-PGA-paclitaxel by tumor cells was about 5-fold greater than that of paclitaxel. Additionally, $\alpha$-PGA-paclitaxel had a significantly longer circulation half-life in plasma than paclitaxel (Adv. Drug Deliver. Rev. 2002; 54:695-713). For the potential of targeting liver cancer cells, the prepared nanoparticles are further conjugated with galactosamine. Hashida et al. reported using $\alpha$-PGA as a polymeric backbone and galactose moiety as a ligand to target hepatocytes (J. Control. Release 1999; 62:253-262). Their in vivo results indicated that the galactosylated $\alpha$-PGA had a remarkable targeting ability to hepatocytes and degradation of $\alpha$-PGA was observed in the liver. The internalization efficiency of the prepared nanoparticles with or without galactosamine conjugated into HepG2 cells (a liver cancer cell line) was examined in vitro using a confocal laser scanning microscope.

Liver cancer is a common lethal disease in Asia (Br J Cancer 1998; 78:34-39). It is also the ninth leading cause of cancer deaths in the United States (Cancer Lett. 1999; 136: 109-118). It is known that chemotherapy for cancers is usually limited by the toxicity of drugs to normal tissues (Adv. Drug Deliver. Rev. 2002; 54:695-713). The self-assembled nanoparticles, composed of amphiphilic block copolymers, have a hydrophobic inner core and a hydrophilic outer shell. In a co-pending application U.S. Ser. No. 10/958,864, filed Oct. 5, 2004, it is disclosed that poly($\gamma$-glutamic acid) (abbreviated as $\gamma$-PGA) and poly(lactide) (abbreviated as PLA) are used to synthesize amphiphilic block copolymers via a simple coupling reaction between $\gamma$-PGA and PLA to prepare a novel type of self-assembled nanoparticles (J. Control. Release 2005; 105:213-225). No aggregation or precipitation of the nanoparticles was observed during storage for up to 1 month, because of the electrostatic repulsion between the negatively charged nanoparticles (J. Control. Release 2005; 105:213-225). $\gamma$-PGA, produced by certain *Bacillus* species, is a naturally occurring anionic homo-polyamide that is made of L-glutamic acid units connected by amide linkages between $\alpha$-amino and $\gamma$-carboxylic acid groups (Crit. Rev. Biotechnol. 2001; 21:219-232). Because of its water-solubility, biodegradability, edibility, and non-toxicity toward humans, several applications of $\gamma$-PGA in food, cosmetics, and medicine have been investigated in the past few years.

Owing to its unique structure, paclitaxel readily enters mammalian cells and preferentially binds to tubulin in polymerized microtubules (J. Biol. Chem. 1995; 270:20235-20238). This binding stabilizes microtubules and greatly interferes with microtubular reorganization necessary, among other factors, for spindle formation and cell division (Cancer Lett. 1999; 136:109-118). Thus, exposure of susceptible cells to paclitaxel has been shown to initially cause arrest in the G2/M phase and finally to cell death through apoptotic mechanisms (Cancer Res. 1996; 56:816-825).

Most chemotherapy drugs are generally taken up non-specifically by all types of cells resulting in serious side effects. Physical cancer therapy, such as radiofrequency ablation, has less side effects but it is difficult to target the specific tumor site or the in vivo range of heating. Therefore, patients may have a recurrence of cancer.

Liposomes have good biocompatibility and can carry hydrophobic or hydrophilic drug. Liposomes can carry the thermal sensitive compound (also known as thermal triggered phase-transition compound), such as $NH_4HCO_3$, which is able to generate $CO_2$ by heat to an elevated temperature in situ to rapidly blow up the liposomes inside a cell. In general, cells would be little damaged if the cell temperature were maintained lower than about 42° C.

Stimuli-responsive nanoparticles (NPs) have been receiving much attention as a drug-delivery vehicle for therapeutic applications. Here we disclose a pharmaceutical composition of biodegradable nanoparticles and a method of intracellularly monitoring/imaging the release of an anticancer drug (for example doxorubicin) from pH-responsive nanoparticles using Förster resonance energy transfer. It is also disclosed pH-responsive doxorubicin (DOX)-loaded NPs, made of N-palmitoyl chitosan bearing a Cy5 moiety (Cy5-NPCS), as an anticancer delivery device.

SUMMARY OF THE INVENTION

Some aspects of the invention provide pH-responsive doxorubicin (DOX)-loaded NPs. The nanoparticles are made of N-palmitoyl chitosan (NPCS) bearing a Cy5 moiety (Cy5-NPCS), as an anticancer delivery device or vehicle. Cy3 and Cy5 are reactive water-soluble fluorescent dyes of the cyanine dye family. The results of our molecular dynamic simulations showed the ability of Cy5-NPCS to self-associate that offered the close proximity between the donor (DOX) and the acceptor (Cy5) required for Förster resonance energy transfer (FRET), while the pH-driven structure transition prescribed the on-to-off switch of the FRET energy transfer. The caveolae-mediated pathway played a major role in the internalization of NPCS NPs. In one embodiment, using the concept of FRET, the DOX fluorescence in the cytosol demonstrated the presence of NPCS NPs in the slightly acidic early endosomes. Following NPCS NPs trafficking into a more acidic organelle (late endosomes/lysosomes), a more evident release of DOX into the cytosol was observed. The released DOX then gradually accumulated in the cell nuclei, leading to a significant cytotoxicity as means for cancer treatment.

Some aspects of the invention provide a liposome nanoparticle or micelle or a pharmaceutical composition of liposome nanoparticles or micelles, the nanoparticle/micelle comprising liposome and at least one thermal triggered phase-transition compound. In one embodiment, the liposome micelle is a liposome-shelled micelle with liposome dominating on the outer surface. In another embodiment, the outer surface is positively charged. In still another embodiment, the liposome micelle further comprises at least one anticancer drug (for example, paclitaxel), chemotherapy components (for example, doxorubicin and cyclophosphamide for treating breast cancer), and/or cancer targeting moiety (for example, galactosamine toward hepatoma cells).

Some aspects of the invention provide a pharmaceutical composition of nanoparticles, the nanoparticles consisting of a positively charged chitosan, a negatively charged substrate, optionally a zero-charge compound, and liposome micelles that contains at least one thermal triggered phase-transition compound, such as ammonium bicarbonate.

Some aspects of the invention provide a pharmaceutical composition of liposome nanoparticles loaded with at least one thermal triggerable phase-transition compound that are adapted for delivery to a blood vessel of the animal subject. In one embodiment, the liposome nanoparticles are further loaded with at least one bioactive agent. Basically, the liposome portion of the liposome nanoparticles of the present invention is relatively thermal insensitive whereas the active content portion of the thermal triggerable phase-change compound of the liposome nanoparticles is highly thermal sensitive. In one embodiment, the liposome portion of the liposome nanoparticles is less thermal sensitive than the thermal triggerable phase-change compound of the liposome nanoparticles.

Some aspects of the invention provide a process for preparing self-assembled nanoparticles using poly(γ-glutamic acid) (γ-PGA) and poly(lactide) (PLA) to synthesize block copolymers via a simple coupling reaction between γ-PGA and PLA. In a further embodiment for targeting liver cancer cells, galactosamine is further conjugated on the prepared nanoparticles as a targeting moiety. γ-PGA, a water-soluble, biodegradable, and non-toxic compound, was produced by microbial fermentation (*B. licheniformis*, ATCC 9945a) and then was hydrolyzed. The hydrolyzed γ-PGA with a molecular weight of 4 kDa and a polydispersity index of 1.3 was used, together with PLA (10 kDa, polydispersity index 1.1), to synthesize block copolymers. The prepared nanoparticles had a mean particle size of about 140 nm with a zeta potential of about −20 mV. One object of the invention provides a process for preparing self-assembled nanoparticles using poly(glutamic acid) (PGA) and poly(lactide) (PLA) to synthesize block copolymers via a simple coupling reaction between PGA and PLA. In one embodiment, the PGA is selected from the group consisting of γ-PGA, α-PGA, water-soluble salts of PGA, metal salts of PGA. In a further embodiment for targeting liver cancer cells, galactosamine is further conjugated on the prepared nanoparticles as a targeting moiety.

Some aspects of the invention relate to a compound or dose for treating liver cancers in a patient comprising nanoparticles composed of γ-PGA-PLA block copolymers conjugated with galactosamine. In a further embodiment, the compound or the dose comprises a therapeutically effective amount of the nanoparticles.

Some aspects of the invention relate to a compound or pharmaceutical composition for treating liver cancers in a patient comprising of nanoparticles composed of γ-PGA-PLA block copolymers, wherein the nanoparticles are loaded with at least one bioactive agent.

Some aspects of the invention relate to a compound or pharmaceutical composition for treating liver cancers in a patient comprising nanoparticles composed of γ-PGA-PLA block copolymers conjugated with galactosamine, wherein the nanoparticles are loaded with at least one bioactive agent.

Some aspects of the invention relate to a compound or pharmaceutical composition for treating liver cancers in a patient comprising nanoparticles composed of γ-PGA-PLA block copolymers configured for targeting tissue cells, wherein the nanoparticles are loaded with at least one bioactive agent of DNA, RNA or siRNA. In one embodiment, the γ-PGA-PLA block copolymers are conjugated with galactosamine for targeting liver tissue cells. In another embodiment, the γ-PGA-PLA block copolymers are conjugated with a tissue-specific targeting moiety for that specific tissue.

In one embodiment, the nanoparticles are mixed in a solution with a nanoparticle concentration of up to 100 μg/ml. In one embodiment, a γ-PGA component prior to polymerization for forming the γ-PGA-PLA block copolymers has a molecular weight of about 4 kDa with a polydispersity index of about 1.3. In another embodiment, the nanoparticles comprise a hydrophobic inner core and a hydrophilic outer shell.

In one embodiment, a mean particle size for the nanoparticles in the compound or dose is in the range of about 10 to 500 nm, preferably in the range of about 50 to 200 nm, and most preferably in the range of about 100 to 150 nm.

In one embodiment, the bioactive agent associated with the nanoparticles of the present invention comprises an anticancer drug or is selected from the group consisting of doxorubicin, adriamycin, cisplatin, taxol, and 5-fluorouracil. In another embodiment, the bioactive agent associated with the nanoparticles of the present invention is selected from the group consisting of epipodophyllotoxins, camptothecins, endiyne antibiotics, taxanes, coformycins, anthracycline glycosides, mytomycin, combretastatin, anthrapyrazoles, and polyamine biosynthesis inhibitors.

Some aspects of the invention relate to a dual-particle tumor targeting system comprising a first ligand-mediated targeting nanoparticle(s) and a second EPR-mediated targeting nanoparticle(s), wherein the first and second nanoparticles are mixed in a solution delivering to the target tumor. In one embodiment, the first nanoparticle alone or the second nanoparticle alone is not cytotoxic to a cell. In another embodiment, the co-location of the first nanoparticle and the second nanoparticle in the tumor cell kills or inactivates the cell. In one embodiment, the nanoparticle-containing solution is configured and adapted for intravenous or intra-arterial injection for treating the tumor or cancer in a patient.

In one embodiment, the first or second nanoparticle of the dual-particle tumor targeting system is biodegradable. In another embodiment, the first or second nanoparticle of the dual-particle tumor targeting system comprises γ-PGA-PLA block copolymers. In a further embodiment, the first nanoparticle is conjugated with galactosamine and/or further comprises a pro-drug ganciclovir or a radiotracer.

In one embodiment, the second nanoparticle of the dual-particle tumor targeting system comprises HSV thymidine kinase gene. In another embodiment, the second nanoparticle of the dual-particle tumor targeting system further comprises matrix metalloproteinases, or an endothelial cells specific promoter selected from a group consisting of VEGF receptor-2 promoter, $\alpha_v\beta_3$ integrin promoter, and bFGF receptor promoter. In an alternate embodiment, the second nanoparticle comprises EC-specific promoter and HSV-TK gene constructed plasmid.

In one embodiment, the first and second nanoparticles of the dual-particle tumor targeting system are mixed in a solution with a nanoparticle concentration of up to 100 μg/ml in the solution. In one embodiment, the first or second nanoparticle is loaded with at least one bioactive agent. In one embodiment, the first nanoparticle, second nanoparticle, or both comprise a hydrophobic inner core and a hydrophilic outer shell.

Some aspects of the invention relate to a method for selectively inhibiting angiogenesis within a tumor, the method comprising delivering a dose of combined. EC-specific promoters and HSV-TK genes to the tumor. In one embodiment, the tumor is hepatoma. In another embodiment, the dose is loaded within a nanoparticle(s). In still another embodiment, the dose further comprises a first ligand-mediated targeting nanoparticle(s), and wherein the EC-specific promoters and HSV-TK genes are loaded within a second nanoparticle(s).

It is one object of the present invention to provide a nanoparticle system and a method for administering DNA, RNA (including short interfering, double-stranded, micro or short hairpin RNA) into an animal subject. In one embodiment, the administration is via injection into a blood vessel through a vein or an artery.

The invention provides a nanoparticle system comprising compounds, compositions, and methods useful for modulating the expression of genes, such as those genes associated with angiogenesis and proliferation, using short interfering RNA molecules. Some aspects of the invention further provide a nanoparticle system that comprises compounds, compositions, and methods useful for modulating the expression and activity of vascular endothelial growth factor (VEGF) and/or vascular endothelial growth factor receptor (e.g., VEGFr1, VEGFr2, VEGFr3) genes, or genes involved in VEGF and/or VEGFr pathways of gene expression and/or VEGF activity by RNA interference (RNAi) using small nucleic acid molecules.

Some aspects of the invention provide a nanoparticle system used in the method of administering the siNA in an animal subject by transcutaneous injection or injection through a vein or an artery, the nanoparticle system comprising chemically synthesized double stranded short interfering nucleic acid (siNA) molecule that directs cleavage of a vascular endothelial growth factor receptor 1 (VEGEr1) RNA via RNA interference (RNAi).

Some aspects of the invention provide a pharmaceutical composition of nanoparticles for lodging in a target tissue of an animal subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 μm to 500 μm in size.

In one preferred embodiment, the lodging of a nanoparticle in a target tissue is promoted/facilitated or enhanced by incorporating ligand-mediated targeting moiety (agent) in the nanoparticle. By ways of illustration, nanoparticle is conjugated with proteins or ligands (for example, galactosamine) that bind to the surface receptor (for example, ASGP Receptor) of hepatocyte (normal cells) and/or hepatocyte-derived cell lines such as hepatoma (abnormal cells). The nanoparticles would be swallowed up by receptor-mediated endocytosis of those cells. This is referred to as "ligand-mediated specific cell targeting" and may be used to lodge DNA, RNA into target tissue cells via a ligand-receptor binding mechanism for the ligand to bind a surface receptor of the cells.

One aspect of the invention provides a pharmaceutical composition of nanoparticles for lodging in a target tissue of an animal subject, each nanoparticle comprising a first component of a positively charged chitosan, a second component of negatively charged substrate that complexes with the first positively charged component, wherein the second component comprises a material selected from the group consisting of γ-PGA, α-PGA, PGA derivatives, glycosaminoglycans, and alginate, and a third component of ligand-mediated targeting moiety. In one embodiment, the second component comprises heparin.

Some aspects of the invention provide a pharmaceutical composition of nanoparticles for lodging in a target tissue cell in situ of an animal subject, the nanoparticles comprising poly(glutamic acid)-poly(lactide) block copolymers that are conjugated with a ligand, wherein the ligand has ligand-receptor binding affinity for the ligand to bind a surface receptor of the tissue cell. In one embodiment, the ligand comprises a receptor-antagonist ligand. In this case, the ligand functions as a targeting medium (with little biological function)

whereas the encapsulated bioactive agent reveals desired biological or biochemical functions. In another embodiment, the PGA is selected from the group consisting of γ-PGA, α-PGA, water-soluble salts of PGA, metal salts of PGA.

One aspect of the invention provides a pharmaceutical composition of nanoparticles for lodging in (or attracting to via the conjugated ligand) a target tissue cell in situ (or in vivo) of an animal subject, the nanoparticles comprising PGA-PLA block copolymers that are conjugated with a ligand, wherein the target tissue cell comprises a liver cell, a tumor or cancer cell.

One aspect of the invention provides a pharmaceutical composition of nanoparticles for lodging in a target tissue cell of an animal subject further comprising at least one bioactive agent, wherein the bioactive agent encapsulated within the nanoparticles is a protein or a peptide.

One aspect of the invention provides a pharmaceutical composition of nanoparticles for lodging in a target tissue cell of an animal subject further comprising at least one bioactive agent, wherein the bioactive agent encapsulated within the nanoparticles is plasmid protein.

One aspect of the invention provides a pharmaceutical composition of nanoparticles for lodging in a target tissue cell of an animal subject further comprising at least one bioactive agent, wherein the bioactive agent encapsulated within the nanoparticles comprises a ribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles is a deoxyribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles comprises a small interfering ribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles comprises a growth factor.

One aspect of the invention provides a pharmaceutical composition of nanoparticles for lodging in a target tissue cell of an animal subject further comprising at least one bioactive agent, wherein the bioactive agent encapsulated within the nanoparticles comprises paclitaxel.

One aspect of the invention provides a pharmaceutical composition of nanoparticles for lodging in a target tissue cell of an animal subject further comprising at least one bioactive agent, wherein the nanoparticle is mixed with trehalose in a freeze-drying process.

One aspect of the invention provides a pharmaceutical composition of nanoparticles for lodging in a target tissue cell of an animal subject further comprising at least one bioactive agent, wherein the nanoparticle is mixed with hexan-1,2,3,4,5,6-hexyl in a freeze-drying process.

One aspect of the invention provides a pharmaceutical composition of nanoparticles for lodging in a target tissue cell of an animal subject, wherein the nanoparticle is crosslinked or partially crosslinked.

One aspect of the invention provides a pharmaceutical composition of nanoparticles for lodging in a target tissue cell of an animal subject, wherein the nanoparticle further comprises an adenovirus vector, the adenovirus vector comprising a small interfering ribonucleic acid. One aspect of the invention provides a pharmaceutical composition of nanoparticles for lodging in a target tissue cell of an animal subject, wherein a surface of the nanoparticle is positively charged. In an alternate embodiment, the surface of the nanoparticle is negatively charged.

Some aspects of the invention provide a method of treating a cancer or tumor cell of an animal subject, comprising steps of: (a) providing a pharmaceutical composition of nanoparticles, wherein the nanoparticles comprise liposome and at least one thermal triggered phase-transition compound; (b) lodging the nanoparticles in the cancer or tumor cell in situ of the animal subject; and (c) supplying thermal energy to the at least one thermal triggered phase-transition compound, wherein the thermal energy is sufficient to cause a phase transition of the thermal triggered phase-transition compound.

Some aspects of the invention provide a method of treating a cancer or tumor cell by providing a pharmaceutical composition of liposome nanoparticles of the present invention to an animal subject, wherein the liposome comprises HSPC (L-α-phosphatidylcholine, hydrogenated), DOTMA (N-[1-(2,3-dioleyloxy)propyl]-N,N,N-trimethylammonium chloride), and cholesterol. In one embodiment, the thermal triggered phase-transition compound is ammonium bicarbonate. In one embodiment, the nanoparticles are adapted for delivery to a blood vessel of the animal subject. In another embodiment, the lodging step is via an endocytosis pathway.

Some aspects of the invention provide a method of treating a cancer or tumor cell by providing a pharmaceutical composition of liposome nanoparticles of the present invention to an animal subject and supplying thermal energy to the at least one thermal triggered phase-transition compound, the thermal energy is supplied via a radiofrequency energy source, via an ultrasonic energy source, via a high-intensity focused ultrasound, or via an electromagnetic energy source. In one embodiment, the duration of the thermal energy supplied to the compound is within 60 minutes, preferably within 30 minutes, and most preferably within 10 minutes.

Some aspects of the invention provide a pharmaceutical composition of nanoparticles for cancer treatment, wherein each nanoparticle comprises N-palmitoyl chitosan, a targeting moiety (for example Cy5, galactosamine, or the like), and at least one anticancer agent. In one embodiment, the anticancer agent is selected from the group consisting of doxorubicin (DOX), cyclophosphamide, paclitaxel, adriamycin, cisplatin, and 5-fluorouracil.

Some aspects of the invention provide a pharmaceutical composition of nanoparticles, wherein each nanoparticle comprises N-palmitoyl chitosan (NPCS) that is conjugated with at least two different moieties, the moieties including a donor moiety and an acceptor moiety having a distance of 10 nm or less between the donor moiety and the acceptor moiety that enables Förster resonance energy transfer. In one embodiment, the donor moiety is an anticancer agent, wherein the anticancer agent may be selected from the group consisting of doxorubicin (DOX), cyclophosphamide, paclitaxel, a chemotherapy component, adriamycin, cisplatin, 5-fluorouracil, alkylating agents, antimetabolites, anthracyclines, plant alkoloids, topoisomerase inhibitors, antimitotics, and anticancer antibiotics.

One aspect of the invention provide Cy5 as the acceptor moiety of the pharmaceutical composition to form anticancer agent-loaded Cy5-NPCS nanoparticles. In one embodiment, the anticancer agent-loaded Cy5-NPCS nanoparticles are characterized with enhanced intracellular localization and anticancer agent release. In another embodiment, the anticancer agent-loaded Cy5-NPCS nanoparticles are characterized with a distance of 10 nm or less between the donor moiety and the acceptor moiety for enabling Förster resonance energy transfer (FRET). In one embodiment, the acceptor moiety is galactosamine or Cy5. In some embodiment, the nanoparticles are adapted for delivery to a blood vessel of an animal subject.

Some aspects of the invention provide Cy3 as the donor moiety and Cy5 as the acceptor moiety of the pharmaceutical composition, wherein the nanoparticles are adapted for sensing a change of an environmental pH intracellularly or extracellularly or the nanoparticles are adapted for discriminating varied acidity of cellular organelles. In one embodiment, the change of an environmental pH is in the range of about 4.0-7.5.

BRIEF DESCRIPTION OF THE DRAWINGS

FIGS. 4A-4F show morphology of the nanoparticles prepared with varying feed weight ratios of paclitaxel to block copolymer (the P/C ratio) obtained by the AFM and TEM.

FIG. 7 shows biodistributions of the nanoparticles loaded with rhodamine 123 (a) without galactosamine conjugated (the NPs) and (b) with galactosamine conjugated (the Gal-NPs) in normal mice.

FIG. 8 shows biodistributions of the nanoparticles loaded with rhodamine 123 (a) without galactosamine conjugated (the NPs) and (b) with galactosamine conjugated (the Gal-NPs) in hepatoma-tumor-bearing nude mice.

FIG. 15 shows a CS-γ-PGA chitosan-shelled nanoparticle having positive surface charges and at least one thermal triggered phase-transition compound (the bioactive agent) being associated in micelles before being encapsulated in nanoparticles.

FIG. 19 shows proposed endocytosis pathways for liposome micelles uptake.

FIG. 24(a)-(b) shows the molecular dynamic simulations showing the conformation transition of DOX-loaded Cy5-NPCS nanoparticles (NPs) at pH 7.0 (simulating the pH environment in the caveosomes) and at pH 5.0 (simulating the pH environment in the lysosomes).

DETAILED DESCRIPTION OF THE EXEMPLARY EMBODIMENTS

Figure 1:
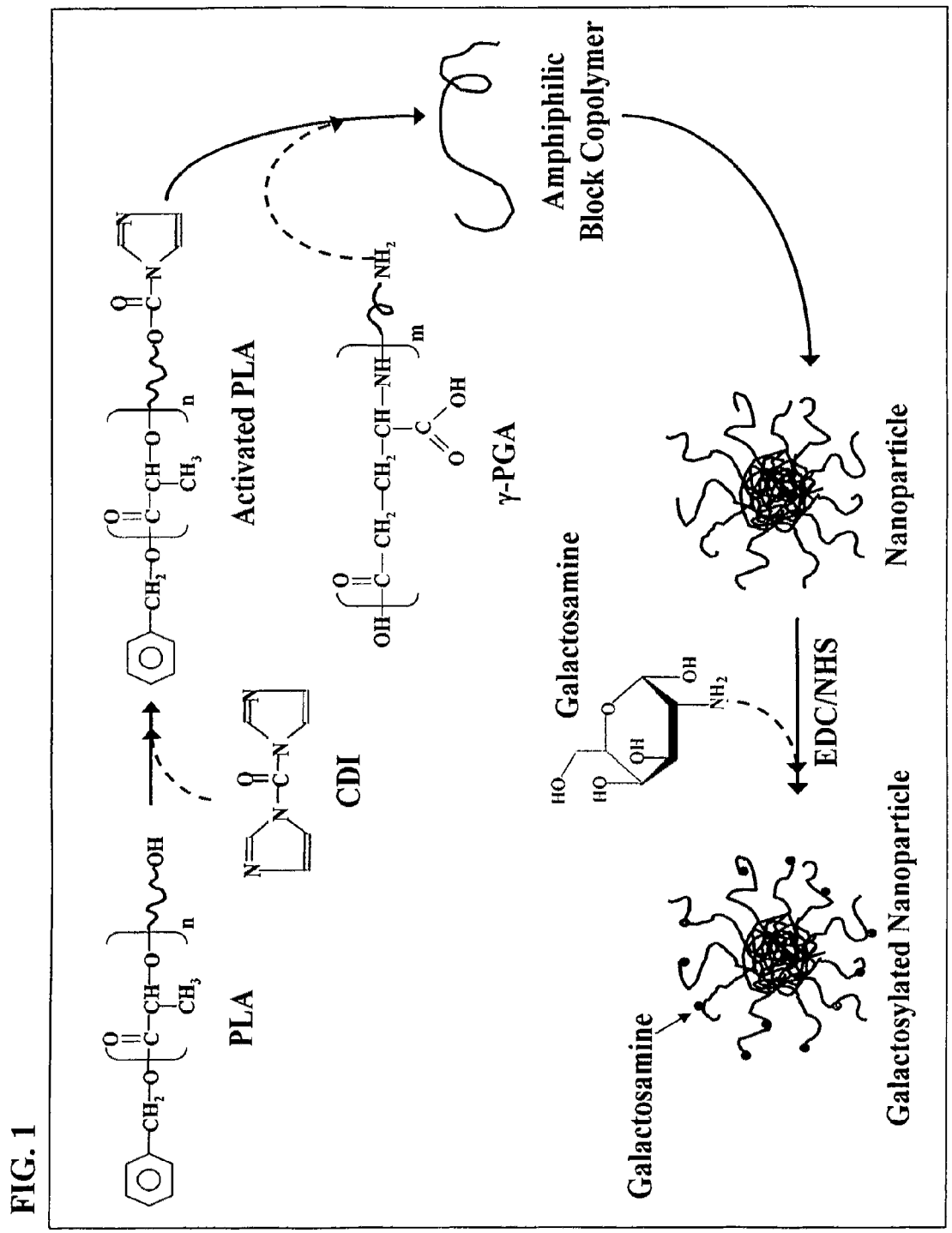
FIG. 1 shows schematic illustrations of synthesis of γ-PGA-PLA block copolymers and formation of self-assembled nanoparticles with galactosamine conjugated.

The preferred embodiments of the present invention described below relate particularly to preparation of pH responsive nanoparticles and a method of intracellularly monitoring/imaging the release of doxorubicin from pH-responsive nanoparticles using Förster resonance energy transfer (FRET). The embodiments further relate to a dual-emission FRET nanoprobe for sensing/imaging pH changes in the biological environment. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Over the past few decades, biodegradable nanoparticles composed of amphiphilic block copolymers have attracted considerable interests as an effective drug carrier. Additionally, numerous attempts have been made to increase the effectiveness of anticancer drugs by increasing their concentration at the target site. In one embodiment, biodegradable and biocompatible polymers, γ-PGA and PLA, are used to synthesize γ-PGA-PLA block copolymers via a simple coupling reaction between γ-PGA and PLA to prepare self-assembled nanoparticles. In addition, galactosamine is conjugated on the prepared nanoparticles as a targeting moiety.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully understood, although it is likely that γ-PGA is linked to the increased survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

Example No. 1

Materials for Making γ-PGA-PLA Block Copolymers

Paclitaxel powder (purity >99%) and clinical commercial paclitaxel [Phyxol®, contained 6 mg paclitaxel, 527 mg Cremaphor EL and 47.7% (v/v) alcohol per milliliter] were obtained from Sinphar Pharmaceutical Co., Ltd. (Taipei, Taiwan). PLA [poly(L-lactide), Mn: 10 kDa, with a polydispersity index of 1.1 determined by the GPC analysis] was supplied by the Biomedical Engineering Center, Industrial Technology Research Institute (Hsinchu, Taiwan). Dimethyl sulfoxide (DMSO<0.01% water), N,N'-carbonyldiimidazole (CDI, 98%), and dichloromethane were acquired from Fluka (Bucks, Switzerland). L-glutamic acid (purity >99%), N-(3-dimethylaminopropyl)-N'-ethylcarbodiimide (EDC), N-hydroxysuccinimide (NHS), galactosamine, and sodium cholate were purchased from Sigma (St. Louis, Mo.). 4-Dimethylaminopyridine (DMAP) and 1,4-dioxane were obtained from ACROS (Janssen Pharmaceuticalaan, Belgium). All other chemicals used in preparing nanoparticles are reagent grade.

Example No. 2

Production and Purification of γ-PGA

γ-PGA (FIG. 1) was produced by *Bacillus licheniformis* (ATCC 9945, Bioresources Collection and Research Center, Hsinchu, Taiwan) as per the method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4 \cdot 7H_2O$, 0.5 g/l, $FeCl_3 \cdot 6H_2O$, 0.04 g/l; $CaCl_2 \cdot 2H_2O$, 0.15 g/l; $MnSO_4 \cdot H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-l jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and 2M HCl. The dissolved oxygen concentration (DOC) was initially controlled at 40% of air saturation by supplying air and by controlling the agitation speed up to 1,000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in distilled water to remove insoluble impurities by centrifugation for 20 minutes at 24,000×g at 4° C. The aqueous γ-PGA solution was desalted by dialysis (MWCO: 12,000-14,000, Spectrum Laboratories, Inc., Laguna Hills, Calif.) against distilled water for 12 hours with water exchanges several times, and finally was lyophilized to obtain pure γ-PGA.

The purified γ-PGA was confirmed by the proton nuclear magnetic resonance ($^1$H-NMR) and the Fourier transformed infrared (FT-IR) analyses. Analysis of $^1$H-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned in the range of 400-4000 $cm^{-1}$.

In the $^1$H-NMR spectrum of the purified γ-PGA obtained from fermentation, five chief signals observed at 1.73, 1.94, 2.19, 4.14, and 8.15 ppm representing the protons of β-$CH_2$, γ-$CH_2$, α-CH, and amide, respectively. Additionally, the fermented product after purification showed no detected macromolecular impurities by the $^1$H-NMR analysis, suggesting that the obtained white power of γ-PGA was highly pure.

Example No. 3

Hydrolysis of γ-PGA

The average molecular weight (Mn) of the purified γ-PGA obtained via the previous fermentation procedure was about 320 kDa. The purified γ-PGA was then hydrolyzed in a tightly sealed steel container at 150° C. for distinct durations. The average molecular weight along with the polydispersity index of the hydrolyzed γ-PGA were determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polyethylene glycol (molecular weights of 106-22,000 g/mol) and polyethylene oxide (molecular weights of 20,000-1,000,000 g/mol) standards of narrow polydispersity index (PL Laboratories, UK) were used to construct a calibration curve. The mobile phase contained 0.01M $NaH_2PO_4$ and 0.2M $NaNO_3$ and was brought to a pH of 7.0. The flow rate of mobile phase was 1.0 ml/min, and the columns and the RI detector cell were maintained at 30° C.

Figure 2:
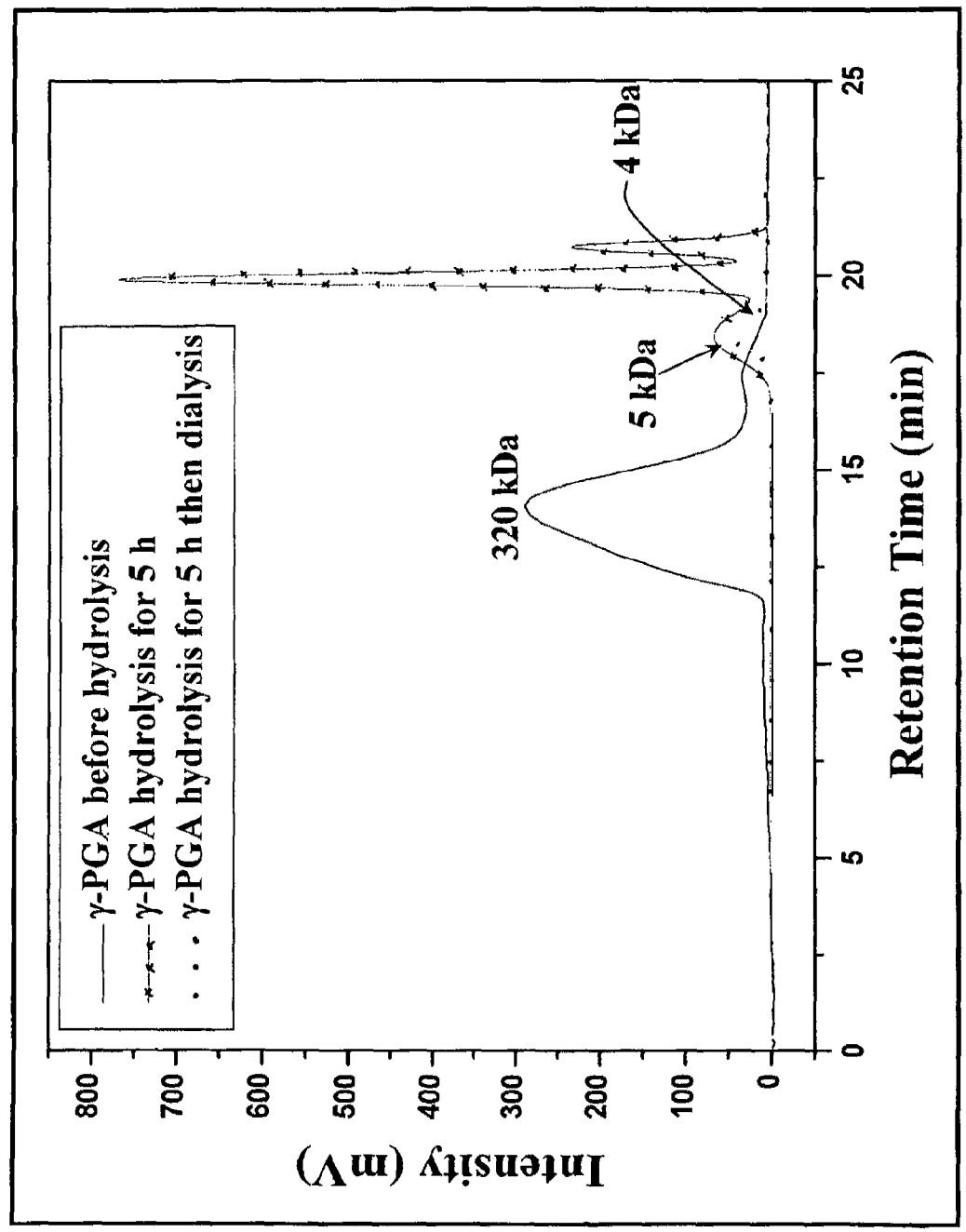
FIG. 2 shows chromatograms of the purified γ-PGA obtained from fermentation (γ-PGA before hydrolysis), the obtained γ-PGA after a 5-h hydrolysis at 150° C. (γ-PGA hydrolysis for 5 h), and the hydrolyzed γ-PGA after dialysis twice against deionized water (γ-PGA hydrolysis for 5 h then dialysis).

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 2, the purified γ-PGA obtained from fermentation had a high average molecular weight (Mn ~320 kDa) with a polydispersity index of about 1.8. When γ-PGA was hydrolyzed at 150° for 5 hours, the average molecular weight of γ-PGA was reduced to about 5 kDa. To reduce the polydispersity index of the hydrolyzed γ-PGA, the hydrolyzed γ-PGA (~5 kDa) was further dialyzed twice (using a membrane with MWCO: 3,500 and a membrane with MWCO: 6,000-8,000) against deionized water. Thus obtained γ-PGA had an average molecular weight of about 4 kDa with a polydispersity index of 1.3 (FIG. 2). This specific γ-PGA was used subsequently, together with PLA, to synthesize block copolymers to prepare the nanoparticles.

Example No. 4

Synthesis of γ-PGA-PLA Block Copolymers

Block copolymers composed of γ-PGA and PLA were synthesized using CDI to activate the terminal hydroxyl group of PLA. CDI (82 mg) was dissolved in 1,4-dioxane (20 ml) in a nitrogen atmosphere and PLA (0.1 g) was subsequently added into the solution. The clear solution was stirred at 37° C. for 2 hours. Afterward, the solution was dialyzed extensively against deionized water at 4° C. Finally, the activated PLA was obtained via centrifugation.

The acidified form of the hydrolyzed γ-PGA (10 mg, Mn ~4 kDa, PDI=1.3) was dissolved in DMSO (5 ml) in a dry, stoppered 20 ml round bottom flask in a nitrogen atmosphere. After dissolution of DMAP (3 mg), a calculated amount of activated PLA (25 mg) was added. The solution was stirred at room temperature for 3 days, after which the reaction was stopped by adding 0.1 ml of concentrated HCl to neutralize DMAP and imidazole. The reaction mixture was transferred to a dialysis tube and dialyzed for 2 days against deionized water at 4° C. Finally, the product (γ-PGA-PLA block copolymers) was lyophilized and stored at −20° C. until used. The molecular weight distribution of the synthesized block copolymers was determined using a GPC system equipped with a Jordi Gel DVB Mixed Bed column (250×10 mm, Jordi Associates, Inc., MA) and a RI detector. Tetrahydrofuran (THF) was used as an elution solvent (1 ml/min) and polystyrene standards for column calibration.

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 2, the purified γ-PGA obtained from fermentation had a high average molecular weight (Mn ~320 kDa) with a polydispersity index of about 1.8. When γ-PGA was hydrolyzed at 150° C. for 5 hours, the average molecular weight of γ-PGA was reduced to about 5 kDa. To reduce the polydispersity index of the hydrolyzed γ-PGA, the hydrolyzed γ-PGA (~5 kDa) was further dialyzed twice (using a membrane with MWCO: 3,500 and a membrane with MWCO: 6,000-8,000) against deionized water. Thus obtained γ-PGA had an average molecular weight of about 4 kDa with a polydispersity index of 1.3 (FIG. 2). This specific γ-PGA was used subsequently, together with PLA, to synthesize block copolymers to prepare the nanoparticles.

Example No. 5

Preparation of the Paclitaxel-Loaded Nanoparticles

The paclitaxel-loaded nanoparticles were produced using an emulsion/solvent evaporation technique. Briefly, 10 mg of block copolymers were dissolved in 1 ml methylene chloride, and paclitaxel was subsequently added with varying feed weight ratios to block copolymer [paclitaxel/copolymer (P/C)=0.5/10, 1/10, 2/10, and 3/10]. The solution was then stirred for 2 hours at room temperature and was emulsified in 50 ml of a 0.1 wt % sodium cholate solution using a sonicator (VCX-750, Sonics & Materials Inc., Newtown, Conn., cycles of 1 second sonication followed by 1 second of pauses, total time 20 minutes). Afterward, the solvent was evaporated in a vacuum oven at 37° C. for 1 hour. The resulting suspension was filtered through a 0.8-μm membrane filter (Whatman) and then centrifuged for 60 min at 18,000 rpm at 4° C. The supernatant was subsequently discarded and the pellet was resuspended by 10 ml phosphate buffered saline (PBS, pH 7.4, Sigma). The size distribution and zeta potential of the prepared nanoparticles were measured using a Zetasizer (3000HS, Malvern Instruments Ltd., Worcestershire, UK).

TEM and AFM were used to observe the morphology of the paclitaxel-loaded nanoparticles. The TEM sample was prepared by placing a drop of the paclitaxel-loaded nanoparticle solution onto a 400 mesh copper grid coated with carbon. About 2 minutes after deposition, the grid was tapped with a filter paper to remove surface water and negatively stained by using a 2% (by w/v) phosphortungsten acid (PTA) solution. The AFM sample was prepared by casting a drop of the paclitaxel-loaded nanoparticle solution on a slide glass and then dried in vacuum.

Figure 3:
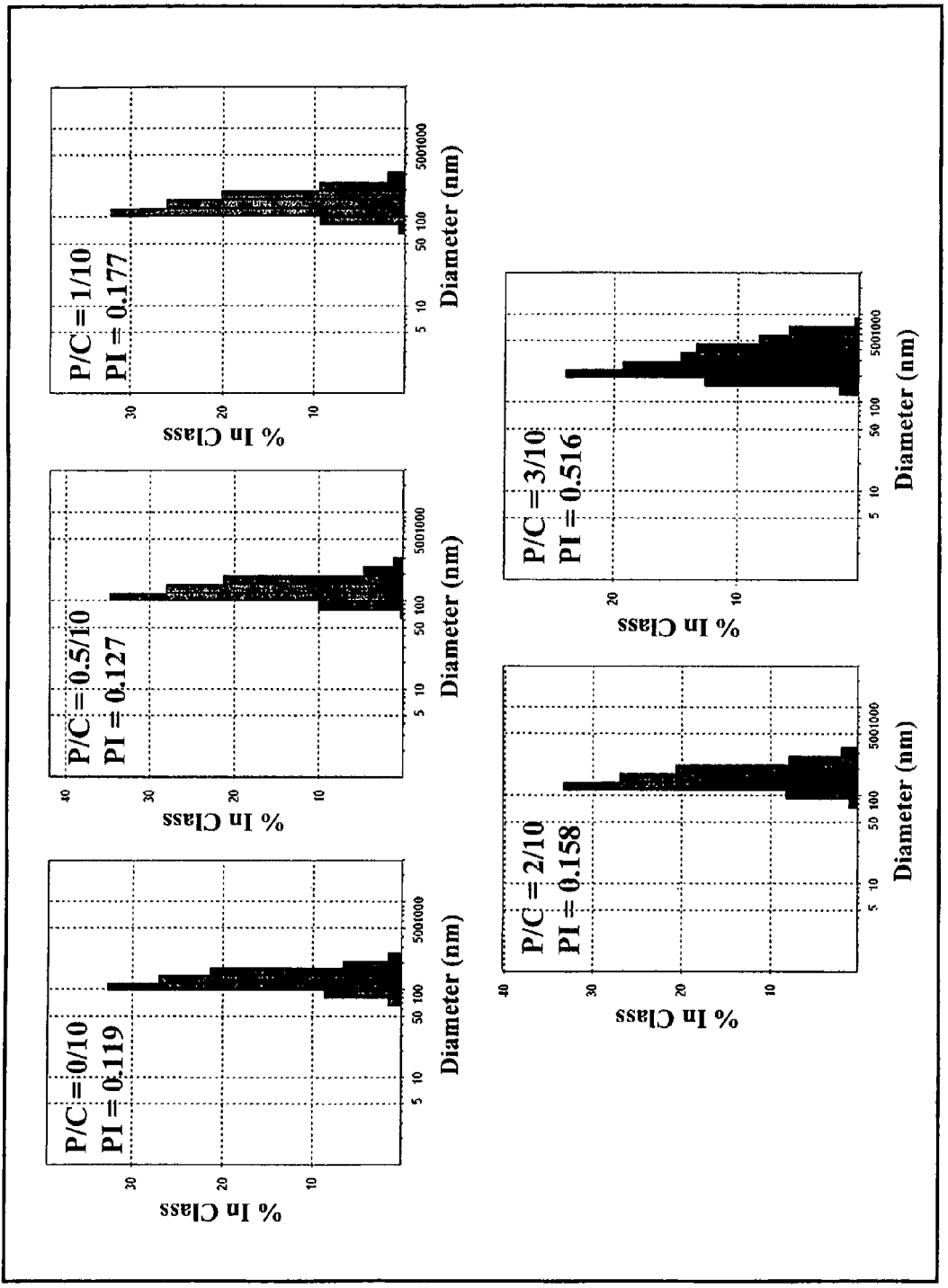
FIG. 3 shows size distributions of the nanoparticles prepared with varying feed weight ratios of paclitaxel to block copolymer (the P/C ratio). PI: the polydispersity index of the size distribution of the prepared nanoparticles.

The size distribution and zeta potential of the prepared nanoparticles play important roles in determining their fates after administration. As shown in Table 1, the particle size of the prepared nanoparticles increases significantly with increasing the P/C ratio. Dynamic light scattering measurements further demonstrated that all the prepared nanoparticles have a narrow size distribution, with the exception of those prepared with a P/C ratio of 3/10 (FIG. 3). The AFM and TEM examinations showed that the morphology of all the prepared nanoparticles is spherical in shape with a smooth surface (FIG. 4).

TABLE 1

Particle size, zeta potential, and drug loading content (LC) and loading efficiency (LE) of the nanoparticles prepared with varying feed weight ratios of paclitaxel to block copolymer (the P/C ratio).

| P/C Ratio (n = 4) | Particle Size (nm) | Zeta Potential (mV) | LC (%) | LE (%) |
|---|---|---|---|---|
| 0/10 | 115.4 ± 4.2 | −21.4 ± 2.3 | — | — |
| 0.5/10 | 125.9 ± 5.5 | −22.5 ± 3.2 | 3.7 ± 0.1 | 76.5 ± 2.4 |

TABLE 1-continued

Particle size, zeta potential, and drug loading content (LC) and loading
efficiency (LE) of the nanoparticles prepared with varying feed weight
ratios of paclitaxel to block copolymer (the P/C ratio).

| P/C Ratio (n = 4) | Particle Size (nm) | Zeta Potential (mV) | LC (%) | LE (%) |
|---|---|---|---|---|
| 1/10 | 128.8 ± 3.4 | −19.6 ± 1.8 | 5.1 ± 0.2 | 53.7 ± 1.7 |
| 2/10 | 144.4 ± 2.6 | −20.3 ± 2.7 | 5.8 ± 0.2 | 30.8 ± 2.3 |
| 3/10 | 263.2 ± 6.8 | −19.2 ± 2.2 | 6.1 ± 0.2 | 21.7 ± 4.2 |

Hashida et al. reported that the majority of the fenestrate of the liver sinusoid is usually smaller than 200 nm in diameter. Thus, large particles hardly reach the liver's parenchymal cells. Additionally, drug carriers with a diameter larger than 200 nm are readily scavenged non-specifically by monocytes and the reticuloendothelial system. It was reported that smaller particles tended to accumulate at the tumor sites due to the EPR (enhanced permeability and retention) effect and a greater internalization was also observed.

As shown in Table 2, the particle size of the Gal-NPs was comparable to that of the NPs ($p>0.05$). However, the zeta potential of the former was significantly lower than that of the latter ($p<0.05$). This is because galactosamine was conjugated to the carboxyl (—COO$^-$) groups on γ-PGA (the hydrophilic shell of the nanoparticles) and thus reduced the negative surface charge of the Gal-NPs. The drug loading content and loading efficiency of the Gal-NPs were relatively lower than those of the NPs ($p<0.05$).

TABLE 2

Particle size, zeta potential, and drug loading content (LC) and
loading efficiency (LE) of the paclitaxel-loaded nanoparticles
without (NPs) or with (Gal-NPs) galactosamine conjugated.

| Samples (n = 4) | Particle Size (nm) | Zeta Potential (mV) | LC (%) | LE (%) |
|---|---|---|---|---|
| NPs | 128.8 ± 3.4 | −19.6 ± 1.8 | 5.1 ± 0.2 | 53.7 ± 1.6 |
| Gal-NPs | 127.5 ± 2.5 | −10.6 ± 2.0 | 4.8 ± 0.2 | 50.2 ± 2.1 |

It was found that the prepared paclitaxel-loaded nanoparticles have a negative surface charge with a zeta potential of about −20 mV (Table 1), due to the carboxyl (—COO$^-$) groups on the hydrophilic γ-PGA shell. This may affect the cellular uptake of the prepared nanoparticles due to electrostatic repulsion forces between the nanoparticles and the rather negatively charged surface of cells. However, Wakebayashi et al. suggested that introduction of a specific ligand on the nanoparticles may enhance their cellular uptake via a receptor-mediated endocytosis. Additionally, it was reported that positively charged carriers might induce a non-specific interaction with unintended target tissues, particularly under in vivo conditions after administration.

Example No. 6

Loading Content and Efficiency of the Paclitaxel-Loaded Nanoparticles

The drug loading content and loading efficiency of the nanoparticles were determined using a high-performance liquid chromatography (HPLC) system equipped with a $C_{18}$ analytic column (4.6×250 mm, particle size 5 μm, ThermoQuest, BDS, Runcorn, UK). Two milligrams of the freeze-dried paclitaxel-loaded nanoparticles were dissolved in 1 ml dichloromethane under vigorous vortexing. This solution was dried by evaporating dichloromethane in vacuum and then was dissolved in a mixture of 50/50 (v/v) ethanol and deionized water for the HPLC analysis. The flow rate of the mobile phase (60% acetonitrile and 40% deionized water by v/v), delivered by an HPLC pump (TCP, P-100, Riviera Beach, Fla.), was 1 ml/min at 30° C. The injection volume was 40 μl and paclitaxel eluted from the column was monitored with an UV detector (Jasco 875-UV, Tokyo, Japan) at 227 nm. The drug loading content and loading efficiency of the nanoparticles were calculated using the equations listed below, respectively.

$$\text{Loading Content (\%)} = \frac{\text{weight of paclitaxel in the nanoparticles}}{\text{weight of the nanoparticles}} \times 100\%$$

$$\text{Loading Efficiency (\%)} = \frac{\text{weight of paclitaxel in the nanoparticles}}{\text{weight of the feeding paclitaxel}} \times 100\%$$

Paclitaxel is highly hydrophobic with a solubility of approximately 1 μg/ml aqueous solution at pH 7.4. Thus, in the drug loading process, incorporation of paclitaxel in the nanoparticles and precipitation of paclitaxel in aqueous solution competed with each other. With increasing the P/C ratio, incorporation of paclitaxel in the nanoparticles (the drug loading content) appears to increase, while precipitation of paclitaxel in aqueous solution is more pronounced and consequently results in a significantly lower drug loading efficiency (Table 1, $p<0.05$).

Example No. 7

Release of Paclitaxel from the Loaded Nanoparticles

The release profiles of paclitaxel from the prepared nanoparticles were investigated in PBS at 37° C. The freeze-dried paclitaxel-loaded nanoparticles were weighed and resuspended in a centrifuge tube containing 20 ml PBS. The tube was placed in a shaker water bath at 37° C. At particular time intervals, the tube was taken out and centrifuged. The supernatant was poured out, freeze-dried, and then dissolved in a mixture of 50/50 (v/v) ethanol and deionized water for the HPLC analysis. The pellet was resuspended in 20 ml fresh PBS for continuous release measurements. The paclitaxel released at each time point was calculated using a calibration curve.

Paclitaxel was continuously released from the nanoparticles prepared with distinct P/C ratios. All samples exhibited a burst release of paclitaxel at the initial stage. About 10-25% of the encapsulated drug was released in the first hour. This may be due to some portion of drugs were deposited at the region near the γ-PGA shell of the prepared nanoparticles.

With increasing the P/C ratio, the release rate of paclitaxel from the prepared nanoparticles decreases significantly. It was reported that a hydrophobic drug encapsulated within the nanoparticles partially crystallizes at a higher drug loading content, while it forms a molecular dispersion at a lower drug loading content. The crystallized drug in the hydrophobic core of the nanoparticles is expected to dissolve more gradually and diffuse to their outer aqueous phase more slowly than that in the form of a molecular dispersion. Additionally, it would take a longer time for the encapsulated drug to diffuse across the polymer matrix to the aqueous medium for a larger size of nanoparticles (i.e., with increasing the P/C ratio, see Table 1).

Figure 5:
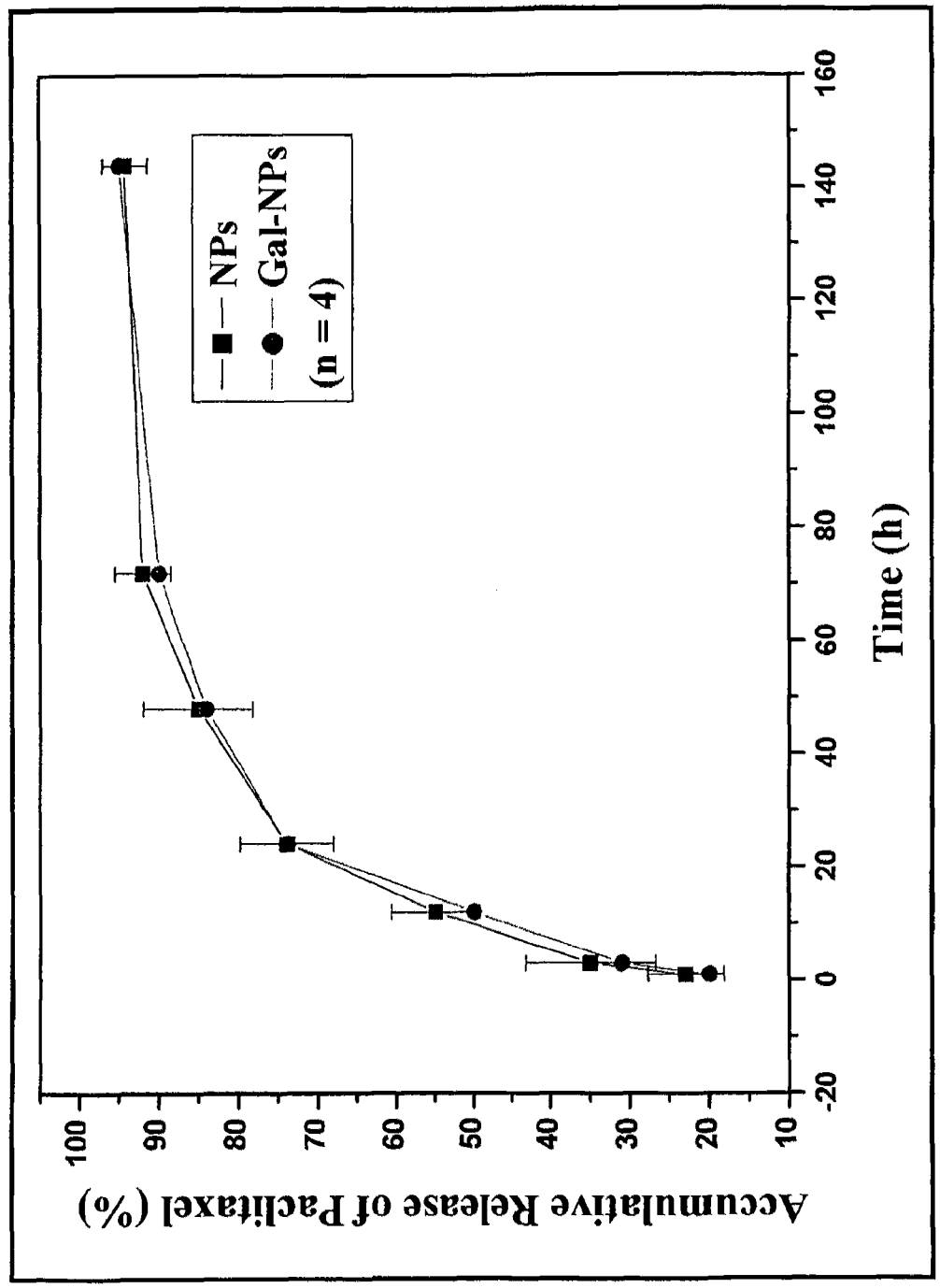
FIG. 5 shows release profiles of paclitaxel from the nanoparticles without (NPs) or with (Gal-NPs) galactosamine conjugated.

As shown in FIG. 5, both the NPs and the Gal-NPs have a similar release profile of paclitaxel (p>0.05) and exhibit a burst release of paclitaxel at the initial stage. About 20% of the encapsulated drug in the NPs or the Gal-NPs was released in the first hour. This may be due to some portion of drugs were deposited at the region near the γ-PGA shell of the prepared nanoparticles.

Example No. 8

Conjugation of Galactosamine to the Paclitaxel-Loaded Nanoparticles

Galactosamine was conjugated to the paclitaxel-loaded nanoparticles via an amide linkage by EDC in the presence of NHS. The conditions found in our co-pending application U.S. Ser. No. 10/958,864 filed Oct. 5, 2004, to conjugate galactosamine on the nanoparticles that had the greatest amount of nanoparticles internalized in HepG2 cells were used in the present study. The obtained galactosylated nanoparticles were separated from unreacted molecules via ultrafiltration and then lyophilized. The content of galactosamine conjugated on the nanoparticles was determined by the Morgan Elson assay.

As discussed earlier, with increasing the P/C ratio, the drug loading content of the prepared nanoparticles increases significantly, while their drug loading efficiency decreases remarkably (Table 1). To obtain a comparatively high drug loading content simultaneously with a high loading efficiency (Table 1), the nanoparticles prepared with a P/C ratio of 1/10 (the NPs) were used for the rest of the study. For the potential of targeting liver cancer cells, galactosamine was conjugated to the paclitaxel-loaded nanoparticles (the Gal-NPs). As determined by the Morgan Elson assay, the amount of galactosamine conjugated on the Gal-NPs was 66.2±2.4 nmole/mg nanoparticles (n=4). The particle size of the Gal-NPs (127.5±2.5 nm) was comparable to that of the NPs (128.8±3.4 nm, p>0.05). However, the zeta potential of the former (−10.6±2.0 mV) was significantly lower than that of the latter (−19.6±1.8 mV, p<0.05). This is because galactosamine was conjugated to the carboxyl (—$COO^-$) groups on γ-PGA and thus reduced the negative surface charge of the Gal-NPs.

Example No. 9

Viability of HepG2 Cells Treated with Distinct Paclitaxel Formulations

The cytotoxicity of the paclitaxel-loaded nanoparticles with or without galactosamine conjugated was evaluated in vitro by the MTT assay, using a clinically available paclitaxel formulation (Phyxol®, Sinphar Pharmaceutical) as a control. The assay is based on mitochondrial dehydrogenase cell activity as an indicator of cell viability. Briefly, MTT [3-(4, 5-dimethyl-thiazol-yl)-2,5-diphenyltetrazolium bromide, Sigma] was dissolved in PBS with a concentration of 5 mg/ml as a stock MTT solution and filtered for sterilization. HepG2 cells were seeded in 24-well plates at $5\times10^4$ cells/well and were allowed to adhere overnight. The growth medium was replaced with a fresh one containing varying concentrations (0.25-8 µg/ml) of distinct paclitaxel formulations investigated in the study: Phyxol®, the nanoparticles without galactosamine conjugated (the NPs), and the nanoparticles with galactosamine conjugated (the Gal-NPs).

The cells were then incubated for 3 days and washed twice by 1 ml PBS. Subsequently, the cells were incubated in a growth medium containing 1 mg/ml MTT agent for an additional 4 hours at 37° C. and 500 µl of DMSO was added to each well to ensure solubilization of formazan crystals. Finally, the optical density readings were performed using a multiwell scanning spectrophotometer (MRX Microplate Reader, Dynatech Laboratories Inc., Chantilly, Va.) at a wavelength of 570 nm.

Hepatoma cells are known to recognize galactose- and N-acetylgalactosamine-terminated glycoproteins via the asialoglycoprotein (ASGP) receptors located on their surfaces. It was found in our previous study that in the incubation with the rhodamine-123-containing nanoparticles without galactosamine conjugated, little fluorescence was observed in HepG2 cells on the images taken by the CLSM. This indicated that without galactosamine, only a small amount of the nanoparticles were able to be internalized in cells, due to electrostatic repulsion forces between the nanoparticles and the cells as mentioned earlier. Hence, the NPs prepared in the study released paclitaxel mainly outside of the cells (i.e., in the culture medium). The released paclitaxel was then diffused into HepG2 cells and led to inhibit the growth of the cells. Accordingly, under in vivo conditions after administration, the normal tissues may be non-selectively exposed to paclitaxel released from the NPs in the blood stream, which can lead to unwanted toxic side effects.

In contrast, with increasing the galactosamine content conjugated on the rhodamine-123-containing nanoparticles, the intensity of fluorescence observed in HepG2 cells increases significantly at 30 min after incubation. This indicates that the galactosylated nanoparticles had a specific interaction with HepG2 cells via ligand-receptor (ASGP) recognition. Therefore, the Gal-NPs prepared in the study were first internalized into HepG2 cells via the ASGP receptors, and then released the encapsulated paclitaxel inside cytoplasm to inhibit the growth of the cells. Thus, the active targeting nature of the Gal-NPs may lead to a high degree of selectivity to the hepatic tumor and enhance their cellular uptake, with a consequent decrease in systemic toxicity.

Figure 6:
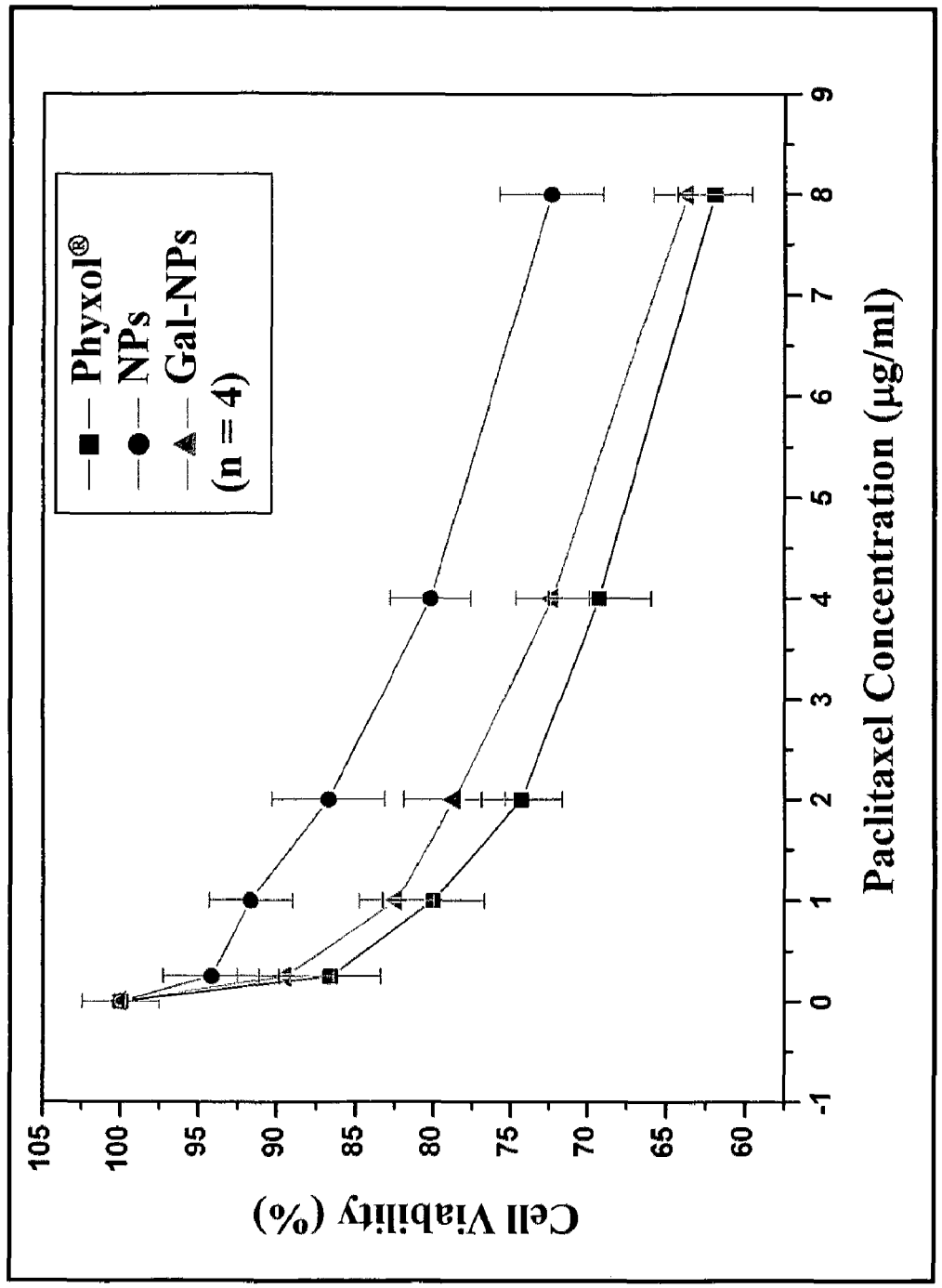
FIG. 6 shows viability of HepG2 cells treated with distinct paclitaxel formulations with varying paclitaxel concentrations. Phyxol®: cells treated with a clinically available paclitaxel formulation (Sinphar Pharmaceutical); NPs: cells treated with the paclitaxel-loaded nanoparticles without galactosamine conjugated; and Gal-NPs: cells treated with the paclitaxel-loaded nanoparticles with galactosamine conjugated.

FIG. 6 shows the viability of HepG2 cells treated with distinct paclitaxel formulations investigated in the study. As shown, the activity in inhibiting the growth of cells by the Gal-NPs was comparable to that of a clinically available paclitaxel formulation (Phyxol®, p>0.05), while the NPs displayed a significantly less activity (p<0.05).

Example No. 10

Immunofluorescence Analysis of HepG2 Cells

HepG2 cells were grown on glass coverslips and then treated with distinct paclitaxel formulations with a final paclitaxel concentration of 8 µg/ml. After incubation for 3 days, the cells were fixed with 3.7% formaldehyde in PBS for 10 min at room temperature and then permeabilized in 0.1% Triton X-100 in PBS containing 1% bovine serum albumin (PBS-BSA) and RNase 100 µg/ml. After washing 3 times with PBS-BSA, the cells were treated with Oregon Green® 514 palloidin (1:100 v/v, Molecular Probes) in PBS-BSA for 20 min. Cells were then incubated for 60 min with anti-bovine α-tubulin mouse mAb (1 µg/ml, Molecular Probes) in PBS-BSA. The Alexa Fluor® 633-conjugated goat anti-mouse IgG antibody (2 µg/ml, Molecular Probes) was added and incubated for another 60 min. Subsequently, cells were rinsed 3 times with PBS-BSA and treated with 100 nM propidium iodide (PI, Sigma) for 5 min.

Before mounting the samples for the CLSM examinations, cells were washed again with PBS and deionized water. Oregon Green® 514 palloidin, PI, or Alexa Fluor® 633 staining were visualized with excitations at 488, 543, and 633 nm, respectively, using an inversed CLSM (TCS SL, Leica, Germany). Superimposed images were performed with an LCS Lite software (version 2.0).

Example No. 11

Altered Cycling States of HepG2 Cells Treated with Distinct Paclitaxel Formulations To demonstrate whether paclitaxel released from the prepared NPs or the Gal-NPs could restrict HepG2 cells in specific cell cycle stages, flow cytometric studies were performed. HepG2 cells treated with distinct paclitaxel formulations with a final paclitaxel concentration of 1 µg/ml for 3 days were pelleted at 1500 rpm for 5 min and then were resuspended in PBS. The cell suspension was then added with 100% methanol precooled to −20° C. for 15 min and centrifuged at 1500 rpm for 5 min. The supernatant was discarded, and the cell pellet was rehydrated with PBS. The pellet was stained with a DNA staining solution (10 µg/ml PI and 1 mg/ml RNase A) for 45 min. The DNA content of each cell was measured using a Becton Dickinson FACSCalibur flow cytometer (San Jose, Calif.).

Some aspects of the invention relate to the paclitaxel-loaded nanoparticles with galactosamine conjugated that are configured to be internalized into HepG2 cells via a receptor-mediated endocytosis, resulting in the inhibition of the growth of cells. Therefore in one embodiment, the prepared nanoparticles are provided as a potential drug delivery system for the targeted delivery to liver cancers.

Example No. 12

Animal Study

Male Balb/c mice (5-7 weeks old, 18-22 g) and Balb/c-nu/nu nude mice (5-7 weeks old, 16-20 g) were obtained from the National Laboratory Animal Center (Taipei, Taiwan) and acclimatized for 7 days after arrival. Nude mice were housed in individually ventilated cages (IVC cages) of isolated ventilation to avoid microbial contamination. Balb/c-nu/nu nude mice were injected subcutaneously in the right flank with 0.1 ml of cell suspension containing $10^6$ human hepatoma cells (HepG2) and allowed to grow to a mean volume of 50 mm$^3$. Animal care and use was performed in compliance with the "Guide for the Care and Use of Laboratory Animals" prepared by the Institute of Laboratory Animal Resources, National Research Council, and published by the National Academy Press, revised 1996.

Example No. 13

Biodistribution of the Prepared Nanoparticles

In the study, rhodamine-123 was used as a model fluorescent probe that can be encapsulated in the hydrophobic core of the prepared nanoparticles. The prepared rhodamine-123-containing nanoparticles in PBS were injected into the tail vein of normal or tumor-bearing mice at a dose of 10 mg/kg. At different time intervals after injection, mice were sacrificed, blood was drawn, and various tissues such as the brain, liver, spleen, lung, kidney, and tumor were excised. An aqueous solution (10 ml) containing deionized water and ethanol (50/50 by v/v) was added to each tissue, and the mixture was homogenized. The mixtures were subsequently centrifuged at 14,000 rpm for 30 min. The supernatants were then lyophilized and resuspended in 1 ml deionized water. Finally, the fluorescence intensities of the solutions were measured using a spectrofluorometer (F-2500, Hitachi, Tokyo, Japan) at an emission wavelength of 520 nm and an excitation wavelength of 490 nm.

Biodistributions of the prepared nanoparticles in various organs in normal mice and hepatoma-tumor-bearing nude mice were evaluated at distinct durations after the injection of the NPs or the Gal-NPs loaded with rhodamine 123. For normal mice, the NPs were distributed mainly in the spleen (FIG. 7a) due to the splenic filtration, whereas the amount of the Gal-NPs observed in the spleen decreased significantly (p<0.05, FIG. 7b). It was found that the Gal-NPs are mainly accumulated in the liver.

For hepatoma-tumor-bearing nude mice, similar observations were observed in the spleen and the liver for the groups injected with the NPs (FIG. 8a) or the Gal-NPs (FIG. 8b). It should be noted that the amount of nanoparticles observed at the tumor site for the group injected with the Gal-NPs was significantly greater than that injected with the NPs (p<0.05).

These observations were further confirmed by our CLSM inspection of the spleen, liver, and tumor sections retrieved from the mice injected with the NPs or the Gal-NPs loaded with rhodamine 123. For the group injected with the NPs, the intensity of fluorescence observed in the spleen was much stronger than in the liver and the tumor site. In contrast, for the group injected with the Gal-NPs, the intensities of fluorescence observed in the liver and the tumor site increased significantly. The aforementioned results indicated that the galactosylated nanoparticles prepared in the study had a specific interaction with liver's parenchymal cells and HepG2 tumor cells via ligand-receptor recognition.

Example No. 14

Anti-Tumor Efficacy of the Prepared Nanoparticles

The anti-tumor efficacy of distinct paclitaxel formulations against the subcutaneously implanted solid tumors induced by HepG2 cells in nude mice was evaluated. Treatments were started when the tumors in nude mice reached a tumor volume of 50 mm$^3$ and this day was designated day 0. Mice were divided into four different groups [treated with PBS (control), Phyxol®, the NPs, or the Gal-NPs], consisting of four mice in each group. Distinct paclitaxel formulations were then injected via tail vein administration at a single dose of 20 mg paclitaxel/kg in PBS on days 0, 4, 8, 12, 16. The size of the tumor and the change of body weight of each mouse were recorded.

Figure 9:
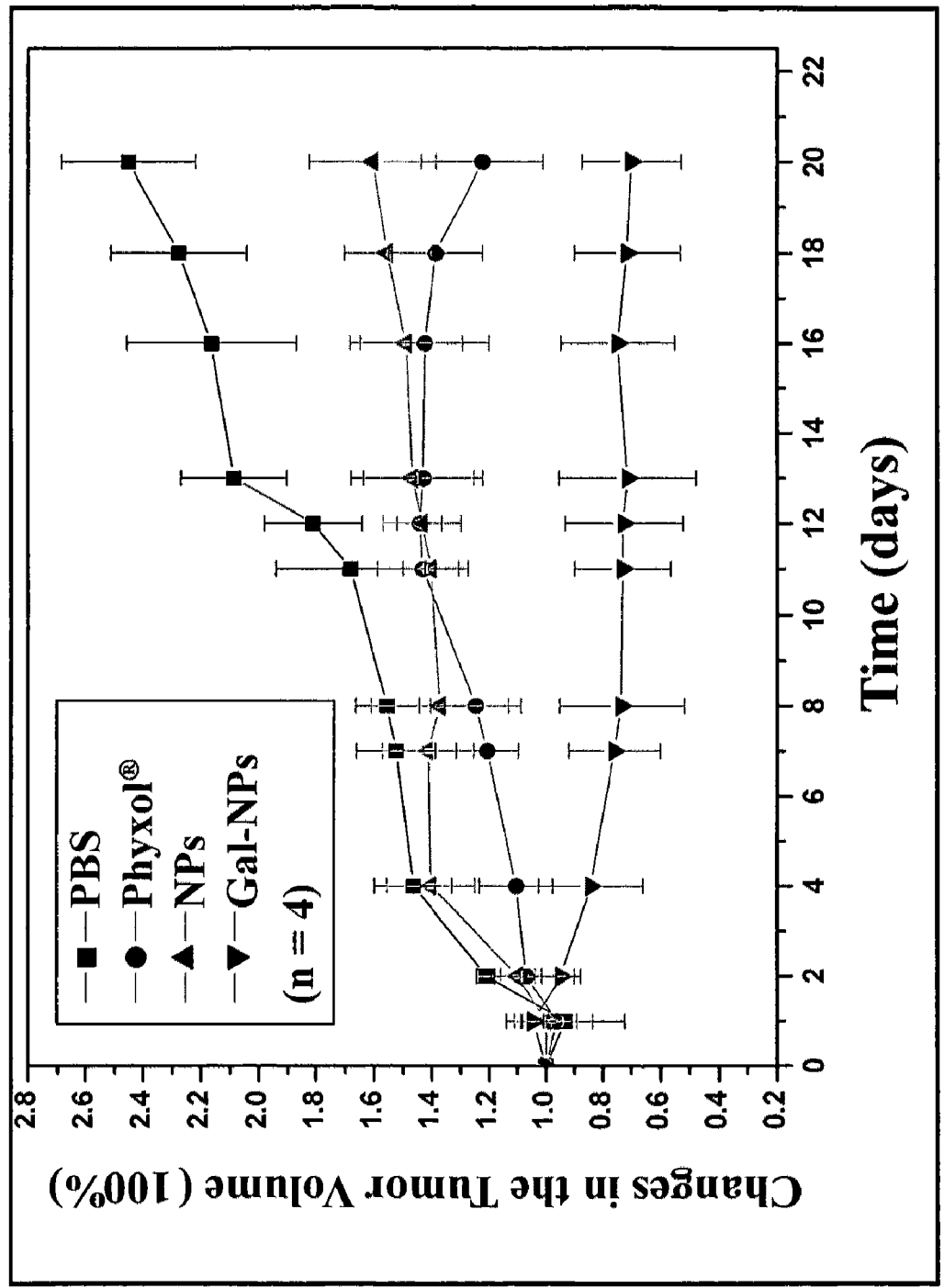
FIG. 9 shows changes in the tumor volume of the hepatoma-tumor-bearing nude mice injected with distinct paclitaxel formulations. PBS: mice injected with PBS; Phyxol®: mice injected with a clinically available paclitaxel formulation (Sinphar Pharmaceutical); NPs: mice injected with the paclitaxel-loaded nanoparticles without galactosamine conjugated; and Gal-NPs: mice injected with the paclitaxel-loaded nanoparticles with galactosamine conjugated.

The anti-tumor efficacy of the NPs and the Gal-NPs was studied in hepatoma-tumor-bearing nude mice. FIG. 9 shows the progress of the tumor growth observed for 20 days in nude mice injected with PBS (control) or distinct paclitaxel formulations. It was found that the size of the tumor for the control group increases significantly with time, indicating that PBS has no significant effect in preventing the tumor growth. In contrast, the groups injected with Phyxol®, the NPs or the Gal-NPs significantly delayed the tumor growth as compared to the control group (p<0.05). Among all study groups, the group injected with the Gal-NPs appears to have the most significant efficacy in the reduction of the size of the tumor (p<0.05). This is because a large number of the Gal-NPs actively targets at the tumor site as mentioned earlier (FIG. 8b), and subsequently release their encapsulated paclitaxel to inhibit the growth of the tumor.

Some weight loss was observed with time for all study groups, with the exception of the group injected with the Gal-NPs (p>0.05). The observation of weight loss was particularly remarkable for the group injected with Phyxol® (p<0.05). These observations implied that for the group injected with Phyxol® (a free form of paclitaxel), paclitaxel is delivered not only to the tumor cells but also to other normal cells in nude mice, whereas the Gal-NPs are mainly accumulated at the tumor site and the liver.

Plasmid DNA

Plasmids (pEGFP-N2, 4.7 kb) containing a CMV promoter and an enhanced green fluorescence protein reporter (EGFP reporter) were obtained from BD Biosciences Clontech (Palo Alto, Calif., USA). pEGFP-N2 was amplified and isolated using a Plasmid Mega Kit (QIAGEN, Valencia, Calif., USA). The recovered plasmids were stored at 4° C. in sterile deionized (DI) water. The purity of plasmids was analyzed by gel electrophoresis (0.8% agarose), while their concentration was measured by UV absorption at 260 nm (V-530, Jasco, Tokyo, Japan). One aspect of the invention relates to preparation of the NPs (i.e., CS/γ-PGA/DNA NPs) encapsulated with a plasmid DNA containing a reporter gene. Physicochemical characteristics of the prepared NPs were examined by Fourier transformed infrared (FT-IR) spectroscopy and transmission electron microscopy (TEM) as well as small angle X-ray scattering (SAXS) and dynamic light scattering (DLS) measurements.

Example No. 15

Preparation of NPs

The charge ratio (N/C/P) of NPs was expressed as the ratio of moles of the amino groups (N) on CS to the carboxyl groups (C) on γ-PGA and the phosphate groups (P) on DNA or siRNA. Test NPs at various known N/C/P molar ratios (study groups of 8:0:1, 8:1:1, 8:2:1, 8:4:1 and 8:6:1) were prepared by an ionic-gelation method. By ways of illustration, an aqueous DNA (pEGFP-N2, 33 μg) was mixed with an aqueous γ-PGA (20 kDa, Vedan, Taichung, Taiwan) at different concentrations (12.8 μg, 25.6 μg, 51.2 μg or 76.8 μg, final volume 80 μl). NPs were obtained upon addition of the mixed solution, using a pipette, into an aqueous CS (80 kDa, 0.4 μg/μl, 400 μl, pH 6.0, Challenge Bioproducts, Taichung, Taiwan). The solutions were thoroughly mixed for 10-15 seconds and left for at least 1 hour at room temperature. NPs were collected by centrifugation at 14,000 rpm for 30 min. Supernatants were discarded and NPs were resuspended in DI water at pH 6.0 for further studies.

Characteristics of CS/γ-PGA/DNA NPs

The pKa values of CS and γ-PGA are 6.5 and 2.9, respectively. In DI water (pH 6.0), CS and γ-PGA are in ionized forms. The ionized CS, γ-PGA and DNA can form polyelectrolyte complexes (CS/γ-PGA/DNA NPs) by ionic interactions between the positively charged amino groups ($-NH_3^+$) on CS and the negatively charged carboxyl groups ($-COO^-$) on γ-PGA and phosphate groups ($-PO_4^-$) on DNA. The particle size, polydispersity index, zeta potential and DNA encapsulation efficiency of NPs prepared at varying N/C/P molar ratios, obtained by DLS, are shown in Table 3. It can be seen that the prepared NPs are in the nanometer scale (150-250 nm) with a positively charged zeta potential. With increasing amount of the negatively charged γ-PGA, the positively charged zeta potential of NPs decreases.

TABLE 3

Particle size (nm), polydispersity index (PI), zeta potential (mV) and encapsulation efficiency (EE, %) of CS/DNA or CS/γ-PGA/DNA nanoparticles prepared at varying N/C/P molar ratios (n = 5). CS: chitosan; γ-PGA: poly-γ-glutamic acid.

| N/C/P Ratio | 8:0:1 | 8:1:1 | 8:2:1 | 8:4:1 | 8:6:1 |
|---|---|---|---|---|---|
| Particle Size | 229.3 ± 29.2 | 174.5 ± 12.1 | 146.0 ± 8.6 | 146.6 ± 10.2 | 173.9 ± 14.7 |
| PI | 0.54 ± 1.81 | 0.43 ± 0.15 | 0.28 ± 0.09 | 0.14 ± 0.03 | 0.17 ± 0.05 |
| Zeta Potential | 36.2 ± 0.5 | 34.3 ± 0.8 | 32.9 ± 1.5 | 20.6 ± 0.8 | 16.4 ± 1.4 |
| EE | 98.4 ± 1.9 | 97.0 ± 2.5 | 96.8 ± 3.1 | 98.1 ± 1.4 | 98.5 ± 1.2 |

The encapsulation efficiencies of DNA in the NPs prepared at distinct N/C/P ratios are about the same and approached 100%, even with the incorporation of the negatively charged γ-PGA. Among all study groups, the NPs prepared at an N/C/P ratio of 8:4:1 have the smallest polydispersity index. Polydispersity index, obtained by the photon correlation spectroscopy analysis, is a parameter defining the particle size distribution of NPs. It is a dimensionless number extrapolated from the autocorrelation function and ranges from a value of 0.01 for monodispersed particles up to a value around 0.5-0.7. A value greater than 0.7 is characteristic of samples with a very broad size distribution. For a better control of DNA delivery or for gene expression, the NPs prepared at an N/C/P ratio of 8:4:1, which display the smallest size distribution among all study groups, were chosen for further studies. However, the NPs at N/C/P ratio range of 8:1:1 to 8:6:1 all show favorably a PI of between about 0.45 and 0.1 and an average particle size of between about 200 nm and 100 nm.

Figure 13:
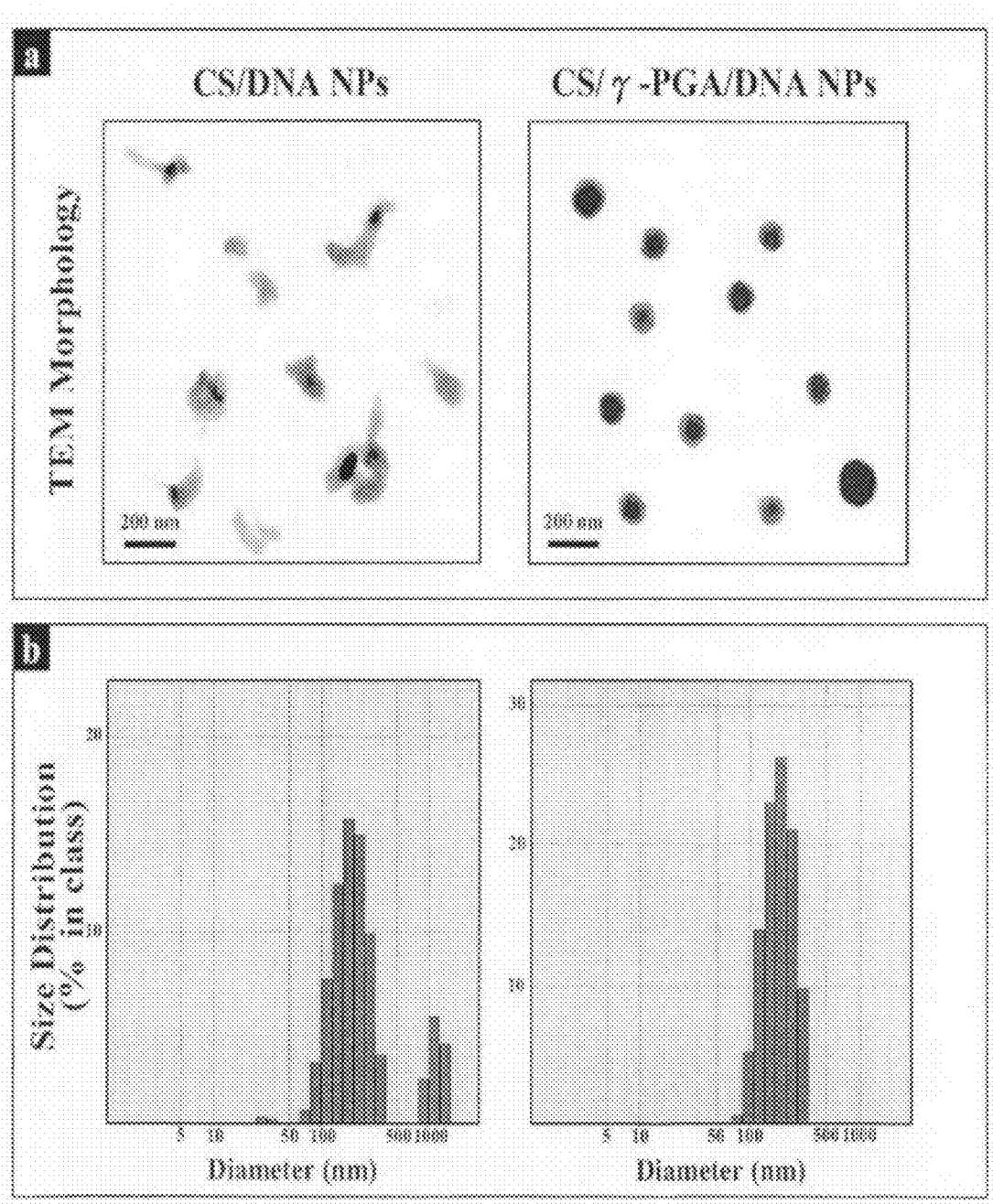
FIG. 13 shows (a) TEM micrographs of CS/DNA and CS/γ-PGA/DNA NPs; (b) size distribution of CS/DNA and CS/γ-PGA/DNA NPs obtained by dynamic light scattering. CS: chitosan; γ-PGA: poly-γ-glutamic acid; NPs: nanoparticles.

In one embodiment, the CS/γ-PGA/DNA NPs (N/C/P ratio of 8:4:1) prepared in DI water (pH 6.0) are spherical in shape with a relatively homogeneous size distribution (FIGS. 13a and 13b). In contrast, CS/DNA NPs (N/C/P ratio of 8:0:1) have a heterogeneous size distribution with a donut, rod or pretzel shape. Similar observation was also reported by other groups on the control CS/DNA NPs. Additionally, the CS/γ-PGA/DNA NPs appear to be more compact than CS/DNA NPs. All other CS/γ-PGA/DNA NPs (N/C/P ratio of 8:1:1 to 8:6:1) are all in spherical or spheroidal shape.

The diameters of NPs observed by TEM (FIG. 13a) (JEOL, Tokyo, Japan) are significantly smaller than those obtained by DLS (Table 3). This is because the diameters of NPs obtained by DLS reflect the hydrodynamic diameters of NPs swollen in aqueous solution, while those observed by TEM are the diameters of dried NPs.

Stability of NPs at Different pH Environments

No aggregation of CS/DNA NPs or CS/γ-PGA/DNA NPs during storage in DI water (pH 6.0) for at least 8 weeks is observed and changes in their particle size and zeta potential are minimal, as a result of the electrostatic repulsion between the positively charged NPs. Precipitation of particles is observed with time (within 2 weeks) for aqueous suspensions of CS/γ-PGA/DNA NPs but not for CS/DNA NPs, indicating that the density of CS/γ-PGA/DNA NPs is greater than that of CS/DNA NPs. However, the precipitated CS/γ-PGA/DNA NPs can be resuspended in DI water after a vigorous vortex.

Figure 14:
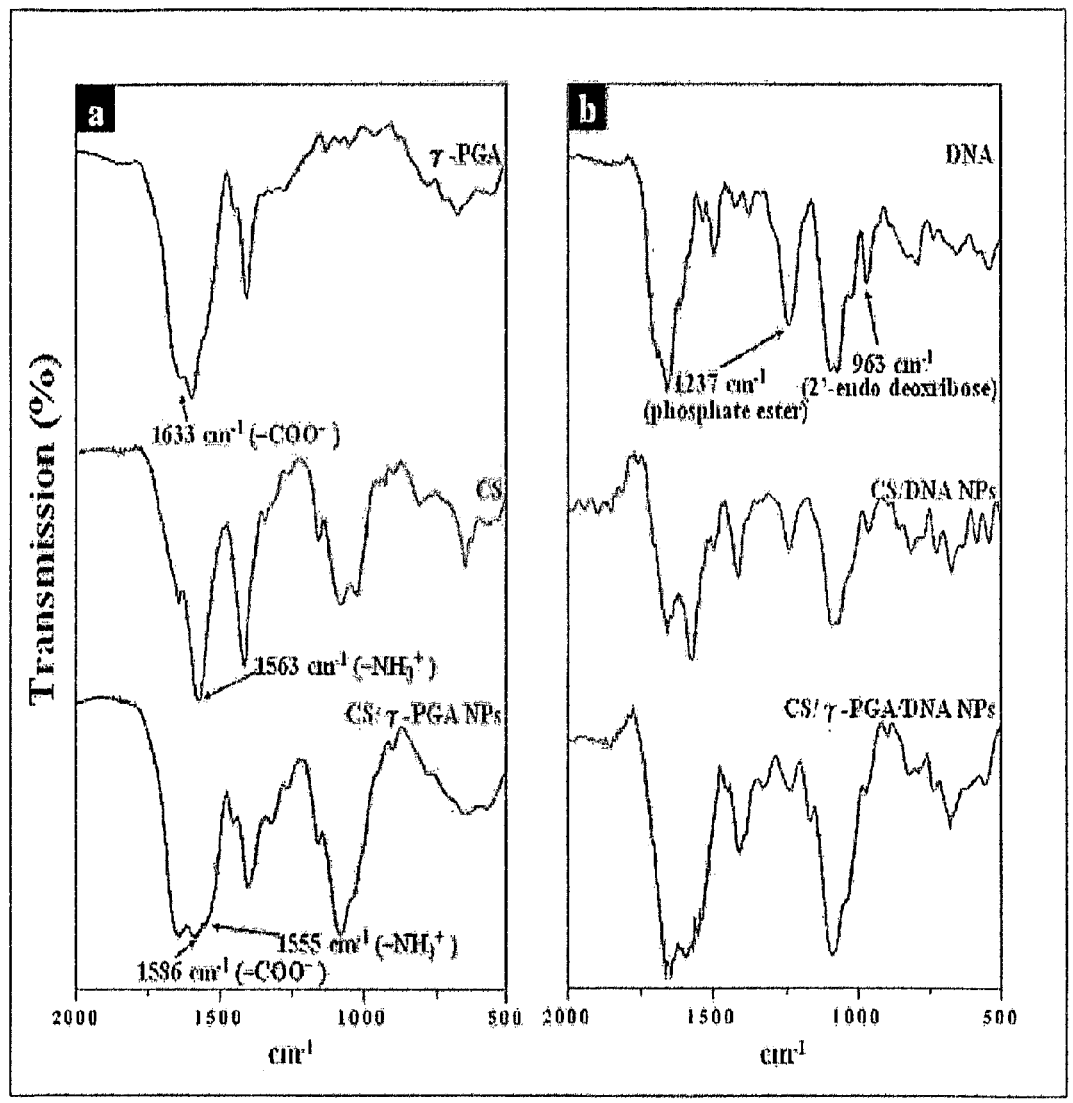
FIG. 14(a)-(b) show TEM micrographs of CS/DNA NPs and CS/γ-PGA/DNA NPs at pH 7.2 and pH 7.6 (simulating the pH environments in the cytoplasm and nuclei of cells, respectively). CS: chitosan; γ-PGA: poly-γ-glutamic acid; NPs: nanoparticles.

At pH 7.2 and pH 7.6 (simulating the pH environments in the cytoplasm and nuclei of cells, respectively), most amino groups on CS are in the form of —$NH_2$. There is little electrostatic interaction between the deprotonated CS and DNA/γ-PGA. CS/DNA NPs and CS/γ-PGA/DNA NPs become unstable and subsequently break apart (FIG. 14). These results indicate that both CS/DNA and CS/γ-PGA/DNA NPs are pH-sensitive.

DNA Protection against DNase I Treatment

It was reported that the plasmid DNA encapsulated in CS/DNA NPs can be protected from nuclease degradation. The plasmid DNA must remain intact to assure its functionality once inside the cell. It is noted that the encapsulation results in a transformation of DNA from the supercoiled to the open circular form. These results indicate that CS/γ-PGA/DNA NPs are able to effectively retain the encapsulated DNA and protect it from nuclease degradation.

Animal Study with CS/γ-PGA/DNA NPs

A carrier must release its encapsulated DNA at some point in the delivery process. The NPs prepared herein are pH-sensitive. At pH values simulating the environments of cytoplasm and nuclei within the cell, both CS/DNA NPs and CS/γ-PGA/DNA NPs become unstable and break apart in a short time (FIG. 14). Therefore, once into skin cells, both test NPs and control NPs might collapse, subsequently release the encapsulated DNA and facilitate expression of the encoded protein.

The Balb/C mice (female, 10-12 weeks old; n=5) were used in the study of DNA delivery. Mice were anesthetized using pentobarbital prior to experiment. After removing the hair covering the abdomen, the skin was wiped with an alcohol swab and allowed to air dry. Subsequently, control NPs (CS/DNA NPs) or test NPs (CS/γ-PGA/DNA NPs) containing 10 μg pEGFP-N2 in sterile DI water (5 μl) were loaded in a low-pressure gene gun and then bombarded into the skin. The helium pressure used was about 100 psi.

CLSM was used to visualize the penetration depth of the FITC-labeled NPs bombarded into the mouse skins using a low-pressure gene gun (about 50-150 psi). This non-invasive method allows for optical sectioning and imaging of the bombarded NPs in the mouse skins, without disrupting their structures. Both test NPs and control NPs are able to penetrate into the mouse skins after bombardment.

CS/DNA NPs were found in the superficial layer of epidermis (including the stratum corneum), whereas CS/γ-PGA/DNA NPs were able to penetrate into deeper regions in the epidermis. Also, there are more CS/γ-PGA/DNA NPs bombarded into the skin as compared with CS/DNA NPs. These observations could be attributed to the fact that CS/γ-PGA/DNA NPs are more compact in their internal structures (with a better integrity propensity; less propensity for breaking-up) and have a greater density than the density of their CS/DNA counterparts, thus having a larger momentum to penetrate into the skin barrier. Some aspects of the invention relate to a nanoparticle system that enhances penetrating efficiency overcoming the skin barrier when bombarded into the skin, wherein the nanoparticle system comprises a composition of CS, γ-PGA, and DNA.

The animal test results show more EGFP (enhanced green fluorescent protein) expression for CS/γ-PGA/DNA NPs than for CS/DNA NPs at 24 hours after bombardment. EGFP expression was mainly localized to the suprabasal layers of epidermis for the group bombarded by CS/γ-PGA/DNA NPs. In contrast, for the group of CS/DNA NPs, EGFP expression was limited to the superficial layer of epidermis. Selective gene expression in the epidermis has potential advantages in gene therapies for various epidermal disorders.

Ligand-Receptor Binding

Some aspects relate to a system, method and pharmaceutical composition of nanoparticles for lodging in tissue cells in situ of a patient, the nanoparticles comprising γ-PGA-PLA block copolymers that are conjugated with a ligand, wherein the ligand has ligand-receptor binding affinity for the ligand to bind a surface receptor of the tissue cells. In biochemistry, a receptor is a protein on the cell membrane or within the cytoplasm or cell nucleus that binds to a specific molecule (a ligand), such as a neurotransmitter, hormone, or other substance, and initiates the cellular response to the ligand. Ligand-induced changes in the behavior of receptor proteins result in physiological changes that constitute the biological actions of the ligands through a ligand-receptor binding process. Ligand binding to a receptor is an equilibrium process. Not every ligand that binds to a receptor it also activates the receptor. Antagonists bind to the receptor but do not activate it. This results in a receptor blockade that inhibits the binding of agonists. In one embodiment, the ligand of the present invention is a receptor-antagonist ligand.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Only the agonists that can maximally stimulate the receptor are defined as a "full agonist". An agonist that can only partially activate the physiological response is called a "partial agonist". Ligands that bind to a receptor but fail to activate the physiological response are receptor "antagonists".

Receptors exist in different types, dependent on their ligand and function. Some receptor proteins are peripheral membrane proteins. Many hormone receptors and neurotransmitter receptors are transmembrane proteins. Transmembrane receptors are embedded in the lipid bilayer of cell membranes that allow the activation of signal transduction pathways in response to the activation by the binding molecule, or ligand. Metabotropic receptors are coupled to G proteins and affect the cell indirectly through enzymes that control ion channels. Ionotropic receptors contain a central pore that functions as a ligand-gated ion channel. Another major class of receptors is intracellular proteins such as those for steroid and intracrine peptide hormone receptors. These receptors often can enter the cell nucleus and modulate gene expression in response to the activation by the ligand. Some transmembrane receptors include, for example, Muscarinic acetylcholine receptor, Adenosine receptors, Adrenoceptors, GABA receptors, Angiotensin receptors, Cannabinoid receptors, Dopamine receptors, Glucagon receptors, Histamine receptors, Olfactory receptors, and so on.

In biochemistry, a ligand is a molecule that is able to bind to and form a complex with a biomolecule to serve a biological purpose. In a narrower sense, it is an effector molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors alters the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters. Radioligands are radioisotope labeled compounds and used in vivo as tracers in PET studies and for in vitro binding studies.

The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme. One aspect of the invention comprises a nanoparticle having a high affinity binding ligand so that the nanoparticle stays with the tissue cells long enough to biodegrade and/or release encapsulated bioactive agent within the nanoparticle.

An advantage of administering a protein or peptide via a biodegradable nanoparticle capable of producing an immune response is the ability to cause the immunogen to be effectively presented to the animal or human over an extended period of time. Similarly, an advantage of administering siRNA via a biodegradable nanoparticle is the ability for siRNA to interfere with the expression of a specific gene over an extended period of time or in a control-release manner. RNA silencing, the process triggered by siRNA molecules, can turn off the ability of cancer cells to produce the key proteins that make them different from normal cells, and by doing so, stop malignancy in its tracks.

Some aspects of the invention provide a pharmaceutical composition of nanoparticles for lodging in a target tissue of an animal subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 µm to 500 µm in size.

Freeze-Dried Nanoparticles

A pharmaceutical composition of nanoparticles of the present invention may comprise a first component of at least one bioactive agent, a second component of chitosan (including regular molecular weight and low molecular weight chitosan), and a third component that is negatively charged. In one embodiment, the second component dominates on a surface of the nanoparticle. In another embodiment, the low molecular weight chitosan has a molecular weight lower than that of a regular molecular weight chitosan. The nanoparticle may further comprise tripolyphosphate and magnesium. For example, a first solution of (2 ml 0.1% γ-PGA aqueous solution @pH 7.4+0.05% Insulin+0.1% Tripolyphosphate (TPP)+0.2% MgSO4) is added to a base solution (10 ml 0.12% chitosan aqueous solution @pH 6.0) as illustrated in Example no. 4 under magnetic stirring at room temperature. Nanoparticles were collected by ultracentrifugation at 38,000 rpm for 1 hour. Supernatants were discarded and nanoparticles were resuspended in deionized water for freeze-drying preparation. Other operating conditions or other bioactive agent (such as protein, peptide, siRNA, growth factor, the one defined and disclosed herein, and the like) may also apply.

Several conventional coating compounds that form a protective layer on particles are used to physically coat the nanoparticles before a freeze-drying process. The coating compounds may include trehalose, mannitol, glycerol, and the like. Trehalose, also known as mycose, is an alpha-linked (disaccharide) sugar found extensively but not abundantly in nature. It can be synthesized by fungi, plants and invertebrate animals. It is implicated in anhydrobiosis—the ability of plants and animals to withstand prolonged periods of desiccation. The sugar is thought to form a gel phase as cells dehydrate, which prevents disruption of internal cell organelles by effectively splinting them in position. Rehydration then allows normal cellular activity to resume without the major, generally lethal damage, which would normally follow a dehydration/rehydration cycle. Trehalose has the added advantage of being an antioxidant.

Trehaloze has a chemical formula as $C_{12}H_{22}O_{11} \cdot 2H_2O$. It is listed as CAS no. 99-20-7 and PubChem 7427. The molecular structure for trehalose is shown below.

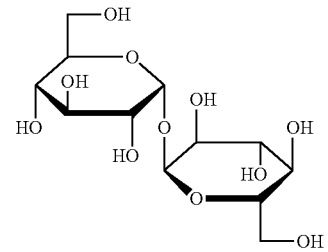

Trehalose was first isolated from ergot of rye. Trehalose is a non-reducing sugar formed from two glucose units joined by a 1-1 alpha bond giving it the name of α-D-glucopyranosyl-(1→1)-α-D-glucopyranoside. The bonding makes trehalose very resistant to acid hydrolysis, and therefore stable in solution at high temperatures even under acidic conditions. The bonding also keeps non-reducing sugars in closed-ring form, such that the aldehyde or ketone end-groups do not bind to the lysine or arginine residues of proteins (a process called glycation). Trehalose has about 45% the sweetness of sucrose. Trehalose is less soluble than sucrose, except at high temperatures (>80° C.). Trehalose forms a rhomboid crystal as the dihydrate, and has 90% of the calorific content of sucrose in that form. Anhydrous forms of trehalose readily regain moisture to form the dihydrate. Trehalose has also been used in at least one biopharmaceutical formulation, the monoclonal antibody trastuzumab, marketed as Herceptin. It has a solubility of 68.9 g/100 g $H_2O$ at 20° C.

Mannitol or hexan-1,2,3,4,5,6-hexyl($C_6H_8(OH)_6$) is an osmotic diuretic agent and a weak renal vasodilator. Chemically, mannitol is a sugar alcohol, or a polyol; it is similar to xylitol or sorbitol. However, mannitol has a tendency to lose a hydrogen ion in aqueous solutions, which causes the solution to become acidic. For this, it is not uncommon to add a substance to adjust its pH, such as sodium bicarbonate. Mannitol has a chemical formula as $C_6H_{14}O_6$. It is listed as CAS no. 69-65-8 and PubChem 453. The molecular structure for mannitol is shown below.

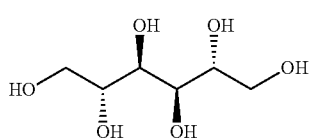

Glycerol is a chemical compound with the formula HOCH₂CH(OH)CH₂OH. This colorless, odorless, viscous liquid is widely used in pharmaceutical formulations. Also commonly called glycerin or glycerine, it is a sugar alcohol and fittingly is sweet-tasting and of low toxicity. Glycerol has three hydrophilic alcoholic hydroxyl groups that are responsible for its solubility in water and its hygroscopic nature. Glycerol has a chemical formula as $C_3H_5(OH)_3$. It is listed as CAS no. 56-81-5. The molecular structure for glycerol is shown below.

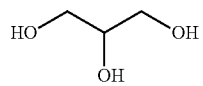

Example No. 16

Freeze-Drying Process for Nanoparticles

Nanoparticles (at 2.5% concentration) were mixed with solution from four types of liquid at a 1:1 volume ratio for about 30 minutes until fully dispersed. The mixed particle-liquid was then freeze-dried under a lyophilization condition, for example, at −80° C. and <25 mmHg pressure for about 6 hours. The four types of liquid used in the experiment include: (A) DI water; (B) trehalose; (C) mannitol; and (D) glycerol, whereas the concentration of the liquid (A) to liquid (C) in the solution was set at 2.5%, 5% and/or 10%. After a freeze-drying process, the mixed particle-liquid was rehydrated with DI water at a 1:5 volume ratio to assess the integrity of nanoparticles in each type of liquid. The results are shown in Table 4. By comparing the particle size, polydispersity index and zeta-potential data, only the nanoparticles from the freeze-dried particle-trehalose runs (at 2.5%, 5%, and 10% concentration level) show comparable properties as compared to those of the before-lyophilization nanoparticles. Under the same data analysis, the nanoparticles from the freeze-dried particle-mannitol runs (at 2.5%, and 5% concentration level) show somewhat comparable properties as compared to those of the before-lyophilization nanoparticles.

Nanoparticle Loaded with siRNA Compound

One aspect of the invention provides a method of administering a bioactive agent into tissue cells in an animal subject by injecting bioactive agent-containing nanoparticles of the present invention intravascularly, wherein the bioactive agent is RNA or siRNA. Ribonucleic acid (RNA) is a nucleic acid polymer consisting of nucleotide monomers that plays several important roles in the processes that translate genetic information from deoxyribonucleic acid (DNA) into protein products. RNA acts as a messenger between DNA and the protein synthesis complexes known as ribosomes, forms vital portions of ribosomes, and acts as an essential carrier molecule for amino acids to be used in protein synthesis. RNA is very similar to DNA, but differs in a few important structural details. RNA nucleotides contain ribose sugars while DNA contains deoxyribose and RNA uses predominantly uracil instead of thymine present in DNA. RNA is transcribed from DNA by enzymes called RNA polymerases and further processed by other enzymes. RNA serves as the template for translation of genes into proteins, transferring amino acids to the ribosome to form proteins, and translating the transcript into proteins.

Figure 12:
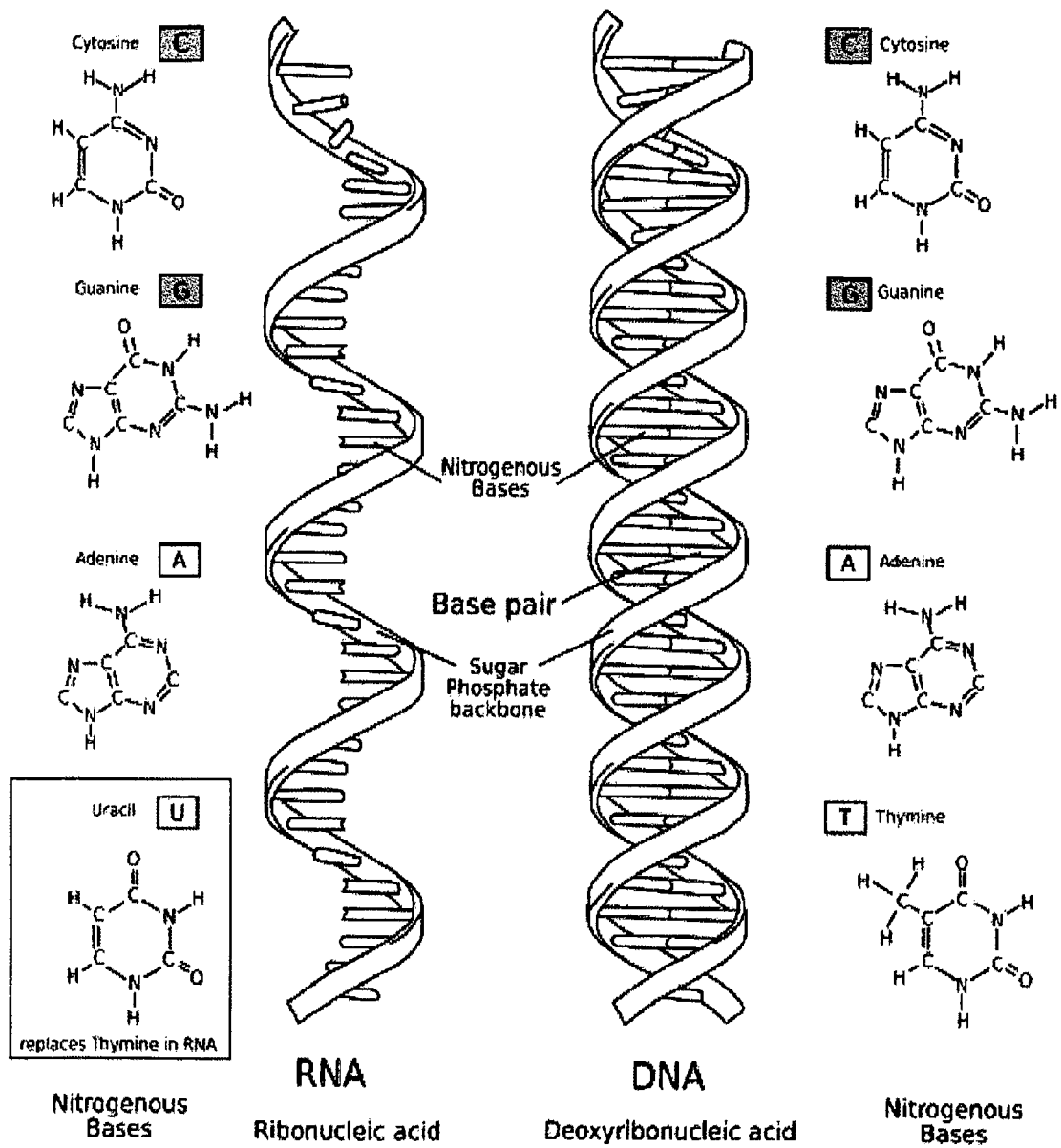
FIG. 12 show chemical and stereochemical structures for a representative RNA and DNA.

RNA is a polymer with a ribose and phosphate backbone and four different nucleotide bases: adenine, guanine, cytosine, and uracil. The first three are the same as those found in DNA, but in RNA thymine is replaced by uracil as the base complementary to adenine. This base is also a pyrimidine and is very similar to thymine. In DNA, however, uracil is readily produced by chemical degradation of cytosine, so having thymine as the normal base makes detection and repair of such incipient mutations more efficient. Thus, uracil is appropriate for RNA, where quantity is important but lifespan is not, whereas thymine is appropriate for DNA where maintaining sequence with high fidelity is more critical. FIG. 12 show chemical and stereochemical structures for a representative DNA and RNA (Wikimedia Commons).

There are also numerous modified bases and sugars found in RNA that serve many different roles. Pseudouridine (Ψ), in which the linkage between uracil and ribose is changed from a C—N bond to a C—C bond, and ribothymidine (T), are found in various places (most notably in the TΨC loop of tRNA). Another notable modified base is hypoxanthine (a deaminated Guanine base whose nucleoside is called Inosine). Inosine plays a key role in the Wobble Hypothesis of the Genetic Code. There are nearly 100 other naturally occurring modified nucleosides, of which pseudouridine and nucleosides with 2'-O-methylribose are by far the most common. The specific roles of many of these modifications in RNA are not fully understood. However, it is notable that in

TABLE 4

Properties of nanoparticles before and after an exemplary freeze-drying process.

| NPs solution | | A: DI Water<br>A: DI Water + NPs<br>(volume 1:1),<br>freeze-dried | | B: Trehalose<br>B: Trehalose + NPs<br>(volume 1:1), freeze-dried | | | C: Mannitol<br>C: Mannitol + NPs<br>(voltage 1:1), freeze-dried | | | D: Glycerol<br>D: Glycerol + NPs<br>(volume 1:1), freeze-dried | | |
|---|---|---|---|---|---|---|---|---|---|---|---|---|
| Conc. | 2.50% | Conc. | | Conc. | 2.50% | 5.00% | 10.00% | Conc. | 2.50% | 5.00% | Conc. | 2.50% | 5.00% | 10.00% |
| Size (nm) | 266 | Size (nm) | 9229.1 | Size (nm) | 302.4 | 316.7 | 318.9 | Size (nm) | 420.1 | 487.5 | Size (nm) | 6449.1 | 7790.3 | 1310.5 |
| Kcps | 352.2 | Kcps | 465.3 | Kcps | 363.7 | 327.7 | 352.2 | Kcps | 305.4 | 303.7 | Kcps | 796.1 | 356.1 | 493.3 |
| PI | 0.291 | PI | 1 | PI | 0.361 | 0.311 | 0.266 | PI | 0.467 | 0.651 | PI | 1 | 1 | 1 |
| Zeta Potential | 25.3 | Zeta Potential | | Zeta Potential | 25.6 | 24.6 | 24.7 | Zeta Potential | 24.4 | 25.3 | Zeta Potential | | | | ribosomal RNA, many of the post-translational modifications occur in highly functional regions, such as the peptidyl transferase center and the subunit interface, implying that they are important for normal function.

The most important structural feature of RNA, that distinguishes it from DNA is the presence of a hydroxyl group at the 2'-position of the ribose sugar. The presence of this functional group enforces the C3'-endo sugar conformation (as opposed to the C2'-endo conformation of the deoxyribose sugar in DNA) that causes the helix to adopt the A-form geometry rather than the B-form most commonly observed in DNA. This results in a very deep and narrow major groove and a shallow and wide minor groove. A second consequence of the presence of the 2'-hydroxyl group is that in conformationally flexible regions of an RNA molecule (that is, not involved in formation of a double helix), it can chemically attack the adjacent phosphodiester bond to cleave the backbone.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome; the complexity of these pathways is only now being elucidated.

SiRNAs were first discovered by David Baulcombe's group in Norwich, England, as part of post-transcriptional gene silencing (PTGS) in plants, and published their findings in *Science* in a paper titled "A species of small antisense RNA in posttranscriptional gene silencing in plants". Shortly thereafter, in 2001, synthetic siRNAs were then shown to be able to induce RNAi in mammalian cells by Thomas Tuschl and colleagues in a paper published in *Nature*. This discovery led to a surge in interest in harnessing RNAi for biomedical research and drug development.

SiRNAs have a well-defined structure: a short (usually 21-nt) double-strand of RNA (dsRNA) with 2-nt 3' overhangs on either end:

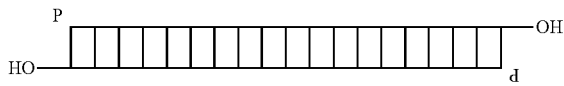

Schematic representation of a siRNA molecule: a ~19-21 basepair RNA core duplex that is followed by a 2 nucleotide 3' overhang on each strand. OH: 3' hydroxyl; P: 5' phosphate.

Each strand has a 5' phosphate group and a 3' hydroxyl (—OH) group. This structure is the result of processing by dicer, an enzyme that converts either long dsRNAs or small hairpin RNAs into siRNAs. SiRNAs can also be exogenously (artificially) introduced into cells by various transfection methods to bring about the specific knockdown of a gene of interest. Essentially any gene of which the sequence is known can thus be targeted based on sequence complementarity with an appropriately tailored siRNA. This has made siRNAs an important tool for gene function and drug target validation studies in the post-genomic era.

RNA interference (RNAi) is a phenomenon in which the introduction of double-stranded RNA (dsRNA) into a diverse range of organisms and cell types causes degradation of the complementary mRNA. Upon introduction into the cell, long dsRNAs enter a cellular pathway that is commonly referred to as the RNA interference pathway. First, the dsRNA's are cleaved into short 21-25 nucleotide small interfering RNAs, or siRNAs, by a ribonuclease known as Dicer. The siRNAs subsequently assemble with protein components into an RNA-induced silencing complex (RISC). The siRNA strands are then unwound to form activated RISCs. These activated RISCs then bind to complementary RNA molecules by base pairing interactions between the siRNA antisense strand and the mRNA. The bound mRNA is cleaved and sequence specific degradation of mRNA results in gene silencing. Although there are different methods to generate siRNA for gene silencing, the easiest and most efficient way to achieve RNAi is to use synthetic small-interfering RNA (siRNA).

In an exemplary illustration, RNA silencing, the process triggered by siRNA molecules, can turn off the ability of cancer cells to produce the key proteins that make them different from normal cells, and by doing so, stop malignancy in its tracks. Early proof-of-principle experiments in various tumor cells showed quickly that RNA silencing had great potential as a means for treating cancer.

RNA oligos are susceptible to degradation by exogenous ribonucleases introduced during handling. RNase-free reagents and supplies should be used. Oligonucleotides may be re-suspended at a convenient concentration in RNase-free sterile water. The use of DEPC-treated water is not recommended. DEPC-treated water is deionized diethylpyrocarbonate treated and 0.22 μm membrane-filtered. Dried RNA oligos are usually stable for 1 year at −20° C. Once re-suspended, oligonucleotides solutions are best kept frozen at −20° C. for several weeks and may remain stable for several months. The most important factor in storing working solutions is using nuclease-free, sterile water. Drying down of your oligos and keeping them at −20° C. is recommended for long-term storage. Some aspects of the invention relate to a siRNA-containing nanoparticle that has been lyophilized (for example, using a freeze dryer by Eyela Co. Ltd, Tokyo, Japan) and stored at −20° C. until it is ready for administering into the tissue cells intravascularly.

The function of a gene can be determined based on the behavior of cells in which the level of gene expression or level of activity of the gene product has been reduced. Experimental procedures can be used to specifically inactivate or silence a target gene or inhibit the activity of its gene product. Inhibition of protein activity can be brought about at the level of gene transcription, protein translation or post translational modifications. For instance, the activity of a protein can be inhibited by directly inhibiting the activity of the protein such as altering a catalytic domain or alternatively by reducing the amount of the protein in the cell by reducing the amount of mRNA encoding the protein. In each case, the level of protein activity in the cell is reduced. Various techniques can be used to knock dawn the activity of a protein and these include knockout technologies (antibodies, antisense RNA, and RNA interference) and compounds that specifically inhibit the protein activity.

The ability to specifically knock down expression of a target gene by siRNA has many benefits. For example, siRNA could be used to mimic true genetic knockout animals to study gene function. There have been reports of using siRNA for various purposes including the inhibition of luciferase gene expression in human cells, (see U.S. Patent Application publication no. 2002/0132788).

The in situ nano-projectile bombardment of the present invention discloses a method of administering a nanoparticle into cells intravascularly in an animal subject, the nanoparticle comprising potent and stable siRNA compounds (or siRNA-containing compounds) to silence the genes that causes serious diseases. The potent and stable siRNA compound may comprise a polynucleotide or vector for expressing short interfering RNAs (siRNAs) to inhibit the expression of a target gene. One aspect of the invention relates to delivering polynucleotides encoding polypeptides to vertebrate cells in vivo, preferably via a vein or an artery. The siRNA compound may include a composition comprising the siRNA of interest and a pharmaceutically acceptable carrier or diluent. The ability to inhibit or disrupt the function of a specific gene is highly desirable. The ability to modulate the expression of a mutated allele or of an inappropriately expressed wild type allele in various diseases or disorders may therefore be used to provide therapies to treat the disorders.

The nanoparticles of the present invention may further comprise an adenovirus vector, wherein the adenovirus vector comprises a polynucleotide construct that may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/of increase half-life, and conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell. In an alternate embodiment, the nanoparticles of the present invention may further comprise an adenovirus vector, wherein the adenovirus vector comprises a siRNA.

Example No. 17

Dual-Particle Tumor Targeting System

In the past few decades, scientists hypothesized that the proteins presented at the surface of a cancer cell will become useful markers to distinguish a malignant cell from normal tissue. Their goal has not been achieved yet because the difference between the surface protein expression patterns of normal and abnormal cells are negligible. It is difficult to find a protein specifically expressed on a tumor cell surface but not on the surface of normal cells. Laboratory experiments and clinical trial results have proved that the drugs or toxins targeting the "tumor marker" are not able to prevent the normal tissue from impairment completely. For example, a clinical trial with immunotoxin-diphtheria toxin/GMCSF fusion protein (DT388GMCSF) on 31 patients with refractory or relapsed acute myeloid leukemia revealed dose-related toxicity such as liver injury, fever, chills, hypoxemia, and transient post-infusion hypotension (Clin Cancer Res 2002; 8:1004-1013).

Tissue functions depend on adequate supply of oxygen and nutrition through blood vessels. The term "angiogenesis" is used to describe the growth of new blood vessels sprouting from preexisting vasculature. Angiogenesis is involved in many physiological and pathological processes such as wound healing, age-related macular degeneration, and tumor progression. Solid tumors require a functional blood supply for their continued growth, and the established tumor vasculature is therefore an attractive target for therapy (Nature Rev. Cancer 2005; 5:423-435). Therapeutic vascular targeting has so far concentrated on anti-angiogenic approaches, which aim to prevent the neovascularization process in tumors. It is disclosed herein that the specific pathological property of most newly formed, immature blood vessels in solid tumors is utilized to direct the specially designed nanoparticles to target these tumors, rather than directly destroy the angiogenic vasculature. This phenomenon is called "EPR effect" (enhanced permeability and retention effect).

The most powerful growth factor secreted by tumor that promotes angiogenesis is VEGF (vascular endothelial growth factor), also named as VPF (vascular permeability factor), which does not only support new blood vessel formation but also enhance permeability of the vasculature. In addition to this protein growth factor, tumor cells also produce other factors such as bradykinin, nitric oxide (NO) and matrix metalloproteinases (MMP) that further increase the permeability of capillaries within a tumor. Based on the synergistic effect of molecules mentioned above, tumor vasculature becomes leaky and allows large substances to pass through. The previous data (Journal of Controlled Release 2000; 65:271-284) using macromolecules and synthetic polymers that hardly penetrate normal blood vessel showed that they are entrapped and accumulate in solid tumors and that they are retained there at high concentrations for prolonged periods. This EPR effect for macromolecules has been observed in many human solid tumors, including hepatoma, renal cancer, lung cancer, and brain tumors. When this kind of drug carrier is used, large amount of polymer or macromolecules will still remain in circulating blood, and finally be caught by lymph nodes, liver, kidney or other organs (Journal of Controlled Release 2000; 65:271-284). The above observation suggests that normal tissue would still possibly be harmed by administration of macromolecules-anticancer drug conjugates that target tumors by EPR effect.

Human body is a very complicated bio-system that consists of billions of different cells and myriads of proteins. As described above, it is impossible to distinguish a tumor from normal tissue and treat the tumor solely with either ligand-mediated specific tumor cell targeting approach or EPR effect-mediated tumor vasculature targeting approach. Thus, it is beneficial to combine advantages of the two targeting methods and limit their shortcomings.

Some aspects of the invention relate to a dual-particle tumor targeting system. By ways of illustration, hepatoma (liver cancer) is used as an experimental demo model. Nanoparticles composed of biodegradable polymers of the present invention are used as drug and gene carriers. A first nanoparticle(s) conjugates with proteins or ligands (for example, galactosamine) which bind to the surface receptor (for example, ASGP receptor) of hepatocyte (normal cells) and hepatocyte-derived cell lines such as hepatoma (abnormal cells). The first conjugated nanoparticle is swallowed up (that is, up-taken) by receptor-mediated endocytosis of those cells. A second nanoparticle(s) that depends upon the EPR effect would accumulate in the angiogenic vasculature within hepatoma. The biodistribution of the above-disclosed two nanoparticles of the dual-particle tumor targeting system would only co-localize within hepatoma to be effective but not in other organs of the human body.

In a co-pending patent application, U.S. application Ser. No. 11/029,082, filed Jan. 4, 2005 and entitled "Nanoparticles For Paracellular Drug Delivery", now U.S. Pat. No. 7,265, 090, entire contents of which are incorporated herein by reference, it is disclosed a nanoparticle made of chitosan or a mixture of chitosan and γ-PGA. In one embodiment, the chitosan is a low molecular weight chitosan. Some aspects of the invention provide a dual-particle tumor targeting system comprising a first ligand-mediated targeting nanoparticle and a second EPR-mediated targeting nanoparticle, wherein the first, the second, or both nanoparticles are made of chitosan or a mixture of chitosan and γ-PGA or a negatively charged substrate.

In a co-pending patent application, U.S. application Ser. No. 11/284,734, filed Nov. 21, 2005 and entitled "Nanoparticles For Protein Drug Delivery", now U.S. Pat. No. 7,282,194, entire contents of which are incorporated herein by reference, it is disclosed a nanoparticle made of crosslinked chitosan or a mixture of crosslinked chitosan and γ-PGA. In one embodiment, the chitosan is a low molecular weight chitosan. Some aspects of the invention provide a dual-particle tumor targeting system comprising a first ligand-mediated targeting nanoparticle and a second EPR-mediated targeting nanoparticle, wherein the first, the second, or both nanoparticles are made of crosslinked chitosan or a mixture of crosslinked chitosan and γ-PGA.

In a further embodiment, it is disclosed to produce cytotoxic effect in tumor cells by using enzyme/substrate system. As is well known to one ordinary skilled in the art, HSV (Herpes-simplex-virus) thymidine kinase gene does not exist in human body; the product of this gene is thymidine kinase enzyme that is nontoxic for human cells. The enzyme only acts on its substrate, e.g., the pro-drug ganciclovir, and thus turn ganciclovir into DNA analogue which can be incorporated into replicating chromosome and thereafter interrupt the DNA replication procedure. After that, cell cycle would be arrested at G2-M phase and then go through apoptosis (J Nucl Med 1997; 38:1230-1233; Science 1992; 256:1550-1552). In one embodiment, the HSV thymidine kinase gene is loaded in a nanoparticle and is used as a suicide gene.

The pro-drug ganciclovir is packaged in the first nanoparticle(s) that targets the hepatocyte/hepatoma cell lines by conjugated with galactosamine, the ligand of ASGP receptor of liver cell surface. The second nanoparticle(s) using EPR effect-mediated targeting contains the suicide gene, for example, HSV thymidine kinase gene. The first and second nanoparticles would only be effective when they co-localize in tumors as described herein. After cancer cells internalize the first and second nanoparticles together, thymidine kinase would digest ganciclovir and produce cytotoxic effect, and then these cancer cells would be killed or inactivated.

Figure 10:
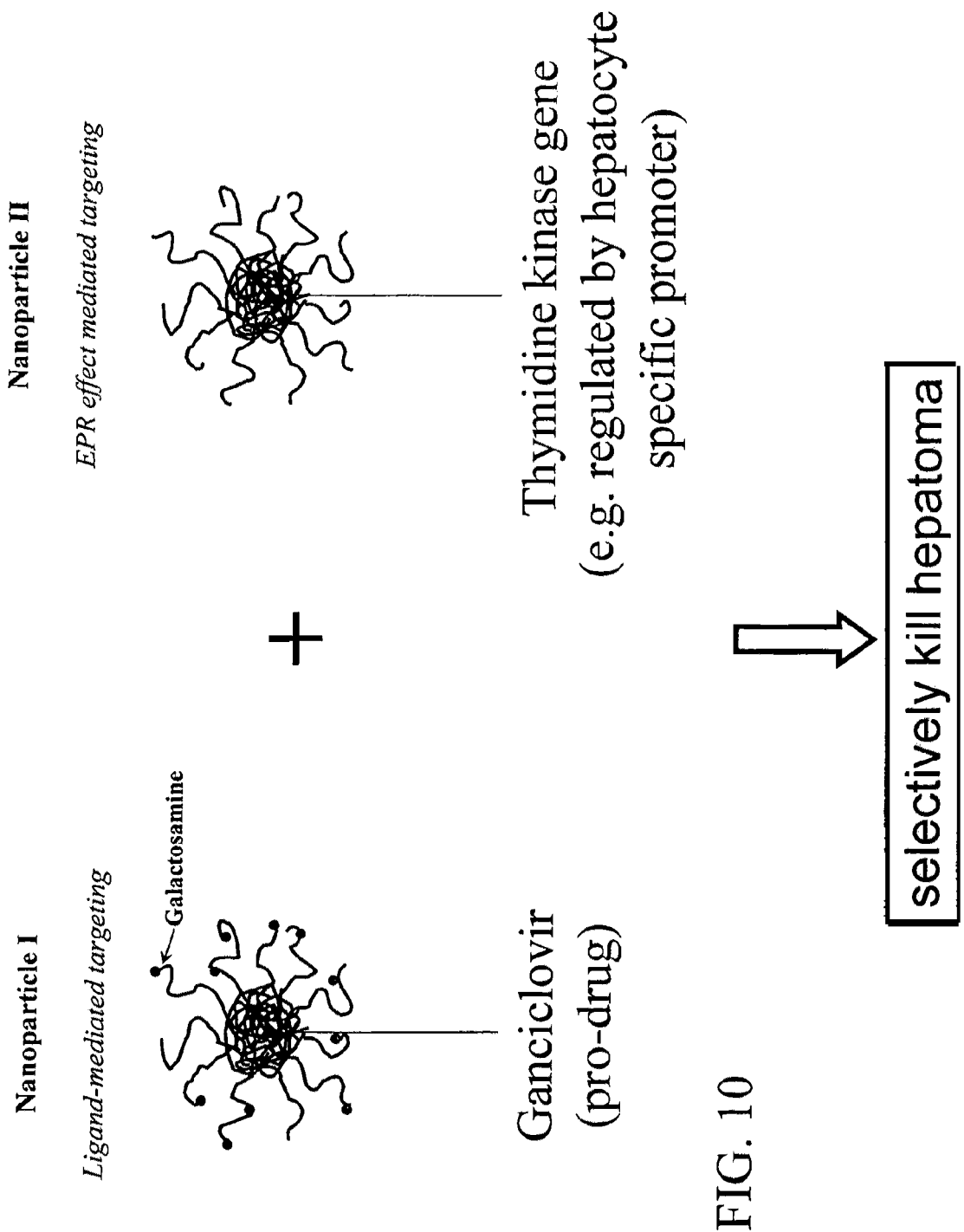
FIG. 10 shows a dual-particle tumor targeting system comprising a first ligand-mediated targeting nanoparticle and a second EPR mediated targeting nanoparticle.

The drug delivery system of the present invention could suppress the tumor progression and destroy the abnormal tissue specifically. The other tissues/organs of human body may gather either the first nanoparticle alone or the second nanoparticle alone, but not produce any cytotoxic effect due to absence of any conjugatable ingredient, thus maintain the side effects at minimum. In one embodiment, the conjugatable ingredient may comprise galactosamine from liver tumor or a ligand of other tumor receptors. For additional safety precaution, a hepatocyte specific promoter could be used to make sure the HSV-thymidine kinase gene would only express at liver-related cells. FIG. 10 shows a dual-particle tumor targeting system comprising a first ligand-mediated targeting nanoparticle(s) with a pro-drug and a second EPR mediated targeting nanoparticle(s) with a thymidine kinase gene. Some aspects of the invention provide a dual-particle tumor targeting system comprising a first ligand-mediated targeting nanoparticle(s) and a second EPR-mediated targeting nanoparticle(s).

In a first alternate embodiment to the dual-particle tumor targeting system of FIG. 10, the matrix metalloproteinase (MMP) promoters would be used to regulate the expression of HSV thymidine kinase (HSV-TK) gene in the second nanoparticles. As is known to one ordinary skilled in the art, matrix metalloproteinases express on most of invasive cancer cells and help them to degrade the extracellular matrix (ECM) and proceed metastasis (Nature Reviews of Cancer 2003; 3:489-501). Using MMP promoter/HSV-TK gene construct enables that this suicide gene would only express within the invasive cancer cells.

Matrix metalloproteinases (MMPs) are zinc-dependent endopeptidases; other family members are adamalysins, serralysins, and astacins. The MMPs belong to a larger family of proteases known as the metzincin superfamily. Collectively they are capable of degrading all kinds of extracellular matrix proteins, but also can process a number of bioactive molecules. They are known to be involved in the cleavage of cell surface receptors, the release of apoptotic ligands (such as the FAS ligand), and chemokine inactivation or activation. MMPs are also thought to play a major role on cell behaviors such as cell proliferation, migration (adhesion/dispersion), differentiation, angiogenesis, apoptosis and host defense. MMPs are distinguished from other endopeptidases by their dependence on metal ions as cofactors, their ability to degrade extracellular matrix, and their specific evolutionary DNA sequence. The MMPs share a common domain structure. The three common domains are the pro-peptide, the catalytic domain and the haemopexin-like C-terminal domain which is linked to the catalytic domain by a flexible hinge region.

Archetypal MMPs include: (A) the collagenases that are capable of degrading triple-helical fibrillar collagens into distinctive ¾ and ¼ fragments, for examples, MMP-1 (interstitial collagenase), MMP-8 (neutrophil collagenase), MMP-13 (collagenase 3), MMP-18, MMP-14 (MT1-MMP), and MMP-2; (B) the stromelysins that display a broad ability to cleave extracellular matrix proteins but are unable to cleave the triple-helical fibrillar collagens, for examples, MMP-3 (stromelysin 1, progelatinase), MMP-10 (stromelysin 2), and MMP-11 (stromelysin 3); (C) other MMPs, for examples, MMP-12 (metallloelastase, macrophage elastase), MMP-19 (RASI-1), Enamelysin (MMP-20), and MMP-27 (MMP-22, C-MMP); (D) the Matrylysins, for examples, MMP-7 (Matrylysin), and MMP-26 (Matrylysin-2); (E) the Gelatinases, for examples, MMP-2 (expressed in most tissues) and MMP-9 (predominantly found in neutrophils); (F) convertase-activatable MMPs, for examples, MMP-11 (stromelysin 3), MMP-21 (X-MMP), and MMP-28 (epilysin); (G) the Membrane Bound MMPs, for examples, the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively); and (H) MMP-23A and MMP-23B.

In a second alternate embodiment to the dual-particle tumor targeting system of FIG. 10, the HSV-TK gene is co-formulated or combined with an endothelial cells specific promoter response for angiogenesis (for example, VEGF receptor-2 promoter, $\alpha_v\beta_3$ integrin promoter, bFGF receptor promoter, and the like), the suicide gene would only destroy the newly formed, immature capillaries within a tumor and shutdown the blood supply to the tumor. The vascular endothelial growth factor (VEGF) receptor-2 (Flk-1) is the first endothelial receptor tyrosine kinase to be expressed in angioblast precursors, and its function is essential for the differentiation of endothelial cells and hematopoietic precursors (Blood 1999; 93:4284-4292). Some aspects of the invention provide a method for selectively inhibiting angiogenesis within hepatoma. Furthermore, the second nanoparticle(s) of the system might contain EC-specific promoter/HSV-TK gene constructed plasmid that would further enhance antiangiogenesis by conjugating with the endothelial cells specific targeting domain at the surface of this second nanoparticle. This EC-specific targeting domain could enhance the specificity for endothelial cells targeting and lead to more efficient inhibition of angiogenesis within a tumor by the suicide gene. The pathological angiogenesis to be treated may include tumor, atherosclerotic plaques, retinopathy, rheumatoid arthritis, and the like.

Figure 11:
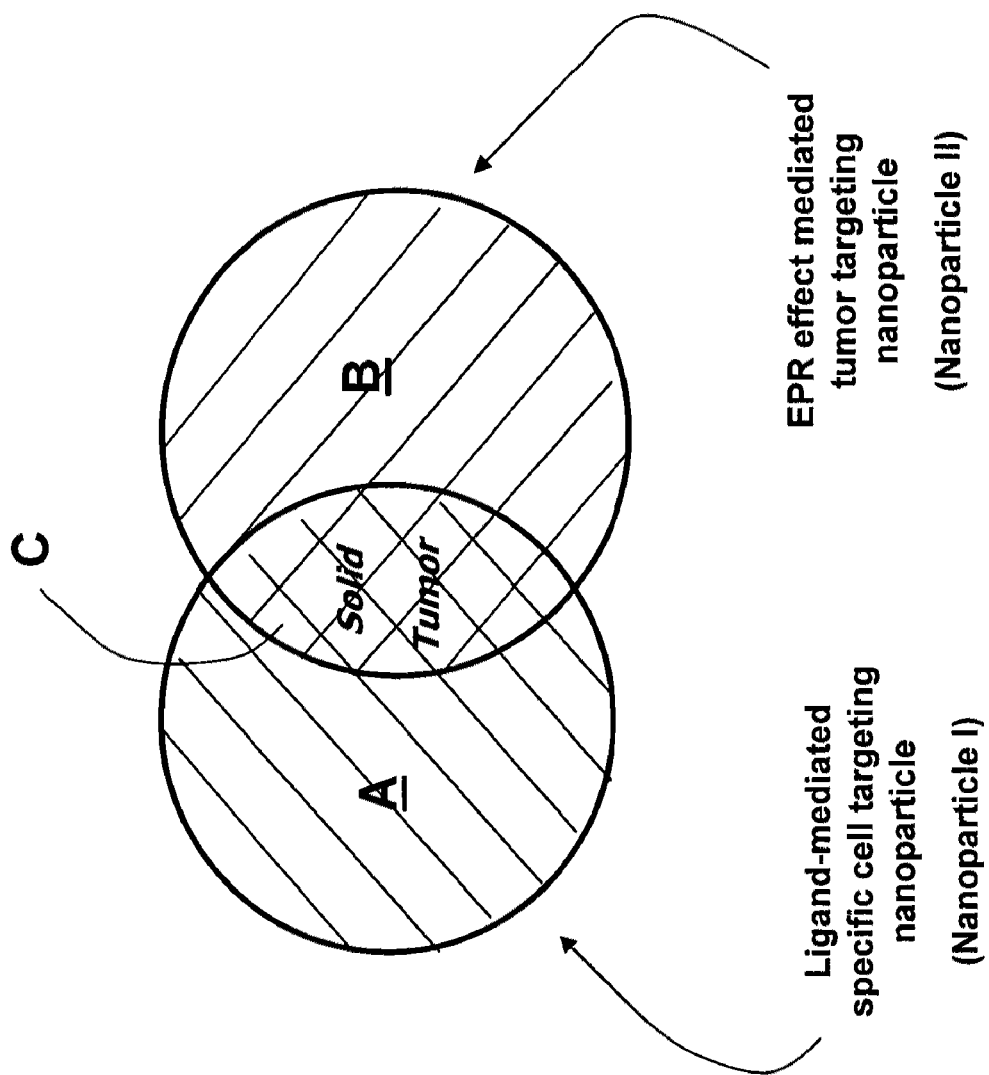
FIG. 11 shows a dual-particle tumor targeting system for locating a tumor.

Clinically, unable to detect (or unable to reliably detect) the early-stage tumors and metastases when they are quiescent with a small size is a major problem for cancer therapy. In addition to the therapeutic ability as disclosed herein, the "dual-particle tumor targeting system" of the invention has potential application to specifically pin point, target, identify, or locate the location of very small tumors. FIG. 11 shows a dual-particle tumor targeting system for locating a tumor, comprising a first ligand-mediated specific cell targeting nanoparticle and a second EPR mediated tumor targeting nanoparticle. The overlapped zone C between the first nanoparticle targeting zone A and the second nanoparticle targeting zone B is where the tumor could be located.

Example No. 18

Locating a Liver Tumor in a Patient

By ways of illustration, a dose of nanoparticles is administrated to a patient, wherein the dose comprises a first ligand-mediated cell targeting nanoparticle(s) and a second EPR-mediated tumor targeting nanoparticle(s). In one embodiment, the first or second nanoparticle is biodegradable. In another embodiment, the first or second nanoparticle is consisted of γ-PGA-PLA block copolymers. The first nanoparticle is conjugated with galactosamine for targeting hepatoma, wherein the first nanoparticle further comprises a radiotracer (for example, $^{18}$F-acyclovir for liver targeting) for locating purposes using a radioactivity counter or imaging instrument. The second nanoparticle comprises HSV thymidine kinase gene that is regulated by hepatocyte. The liver tumor cells that express this gene after up-taking both the first and the second nanoparticles possess radioactivity. It becomes feasible to take the radiograph of a patient to locate the liver tumor by using a PET (positron emission tomography) scan technique.

In a further alternate embodiment to the dual-particle tumor targeting system of FIG. 10, the HSV-TK suicide gene packaged in the second nanoparticle becomes a receptor gene whereas the first nanoparticle contains the radiotracer, for example, $^{131}$I/$^{124}$I-FIAU for RG2/W256 tumor, $^{18}$F-acyclovir for liver tissue, or $^{18}$F-FHPG for 9 L glioma tissue. The enzyme produced by HSV-TK gene would receive and digest the radiotracer resulting in immovable metabolite with radioactivity and then stays inside the tumor cells that express this gene. Using PET (positron emission tomography), SPET (single photon emission tomography), MRI (magnetic resonance imaging) scan technique to take the radiograph of a patient, we could monitor/image the location, size and number of in situ tumors, and metastases.

Example No. 19

Micelles

Figure 18:
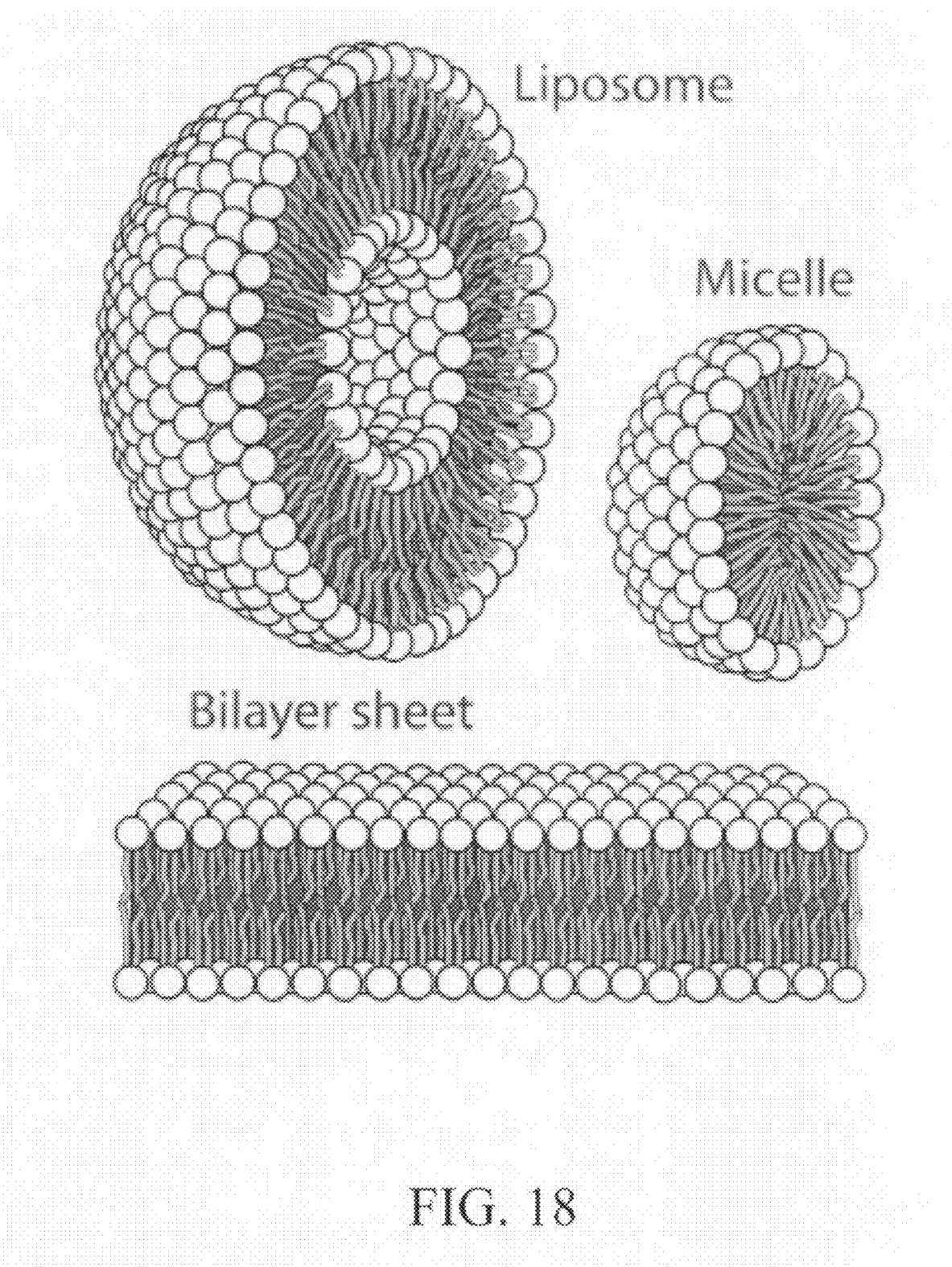
FIG. 18 shows cross-sections of different structures that phospholipids can take in an aqueous solution. The circles are the hydrophilic heads and the wavy lines are the fatty acyl side chains.

A micelle is an aggregate of surfactant molecules dispersed in a liquid colloid. A typical micelle in aqueous solution forms an aggregate with the hydrophilic "head" regions in contact with surrounding solvent, sequestering the hydrophobic single tail regions in the micelle centre (see FIG. 18). This phase is caused by the insufficient packing issues of single tailed lipids in a bilayer. The difficulty filling all the volume of the interior of a bilayer, while accommodating the area per head group forced on the molecule by the hydration of the lipid head group leads to the formation of the micelle. This type of micelle is known as a normal phase micelle (oil-in-water micelle). Inverse micelles have the headgroups at the centre with the tails extending out (water-in-oil micelle). Micelles are approximately spherical in shape. Other phases, including shapes such as ellipsoids, cylinders, and bilayers are also possible. The shape and size (typically a few nanometers to micrometers) of a micelle is a function of the molecular geometry of its surfactant molecules and solution conditions such as surfactant concentration, temperature, pH, and ionic strength. The process of forming micelles is known as micellization and forms part of the phase behavior of many lipids according to their polymorphism.

The ability of a soapy solution to act as a detergent has been recognized for centuries. The existence of "colloidal ions" or the highly mobile, spontaneously formed clusters came to be called micelles. Individual surfactant molecules that are in the system but are not part of a micelle are called "monomers." Lipid micelles represent a molecular assembly in which the individual components are thermodynamically in equilibrium with monomers of the same species in the surrounding medium. In water, the hydrophilic "heads" of surfactant molecules are always in contact with the solvent, regardless of whether the surfactants exist as monomers or as part of a micelle. However, the lipophilic "tails" of surfactant molecules have less contact with water when they are part of a micelle—this being the basis for the energetic drive for micelle formation. In a micelle, the hydrophobic tails of several surfactant molecules assemble into an oil-like core the most stable form of which has no contact with water. By contrast, surfactant monomers are surrounded by water molecules that create a "cage" of molecules connected by hydrogen bonds. This water cage is similar to a clathrate and, has an ice-like crystal structure and can be characterized according to the hydrophobic effect. The extent of lipid solubility is determined by the unfavorable entropy contribution due to the ordering of the water structure according to the hydrophobic effect.

Micelles composed of ionic surfactants have an electrostatic attraction to the ions that surround them in solution, the latter known as counterions. Although the closest counterions partially mask a charged micelle (by up to 90%), the effects of micelle charge affect the structure of the surrounding solvent at appreciable distances from the micelle. Ionic micelles influence many properties of the mixture, including its electrical conductivity. Adding salts to a colloid containing micelles can decrease the strength of electrostatic interactions and lead to the formation of larger ionic micelles. This is more accurately seen from the point of view of an effective change in hydration of the system.

Micelles only form when the concentration of surfactant is greater than the critical micelle concentration (CMC), and the temperature of the system is greater than the critical micelle temperature, or Kraft temperature. The formation of micelles can be understood using thermodynamics: micelles can form spontaneously because of a balance between entropy and enthalpy. In water, the hydrophobic effect is the driving force for micelle formation, despite the fact that assembling surfactant molecules together reduces their entropy. At very low concentrations of the lipid, only monomers are present in true solution. As the concentration of the lipid is increased, a point is reached at which the unfavorable entropy considerations, derived from the hydrophobic end of the molecule, become dominant. At this point, the lipid hydrocarbon chains of a portion of the lipids must be sequestered away from the water. Therefore, the lipid starts to form micelles. Broadly speaking, above the CMC, the entropic penalty of assembling the surfactant molecules is less than the entropic penalty of caging the surfactant monomers with water molecules. Also important are enthalpy considerations, such as the electrostatic interactions that occur between the charged parts surfactants.

In a non-polar solvent, it is the exposure of the hydrophilic head groups to the surrounding solvent that is energetically unfavorable, giving rise to a water-in-oil system. In this case, the hydrophilic groups are sequestered in the micelle core and the hydrophobic groups extend away from the centre. These inverse micelles are proportionally less likely to form on increasing headgroup charge, since hydrophilic sequestration would create highly unfavorable electrostatic interactions.

When surfactants are present above the CMC, they can act as emulsifiers that will allow a compound that is normally insoluble (in the solvent being used) to dissolve. This occurs because the insoluble species can be incorporated into the micelle core, which is itself solubilized in the bulk solvent by virtue of the head groups' favorable interactions with solvent species. The most common, example of this phenomenon is detergents, which clean poorly soluble lipophilic material (such as oils and waxes) that cannot be removed by water alone. Detergents also clean by lowering the surface tension of water, making it easier to remove material from a surface. The emulsifying property of surfactants is also the basis for emulsion polymerization.

Figure 16:
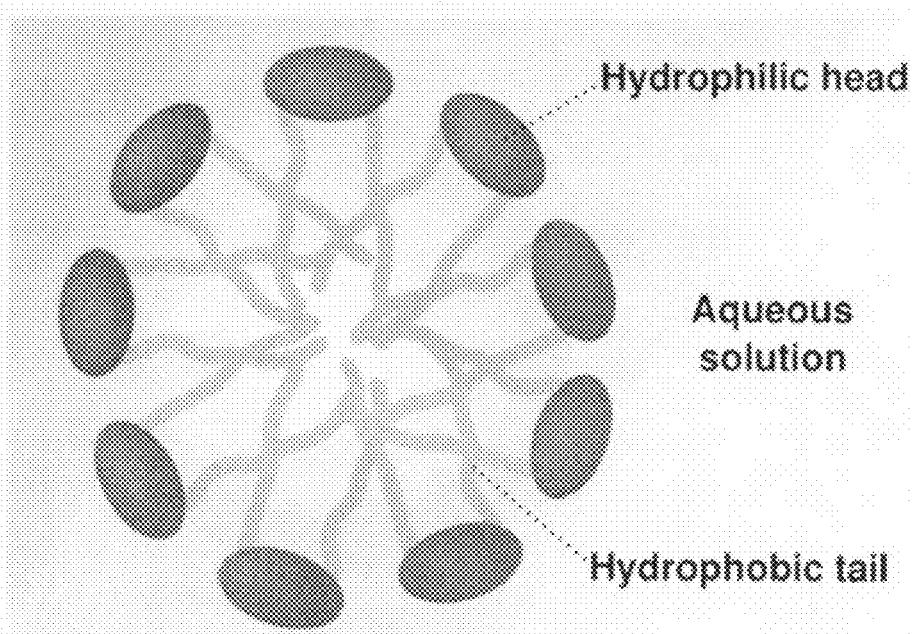
FIG. 16 shows scheme of a micelle formed by phospholipids in an aqueous solution.
Figure 17:
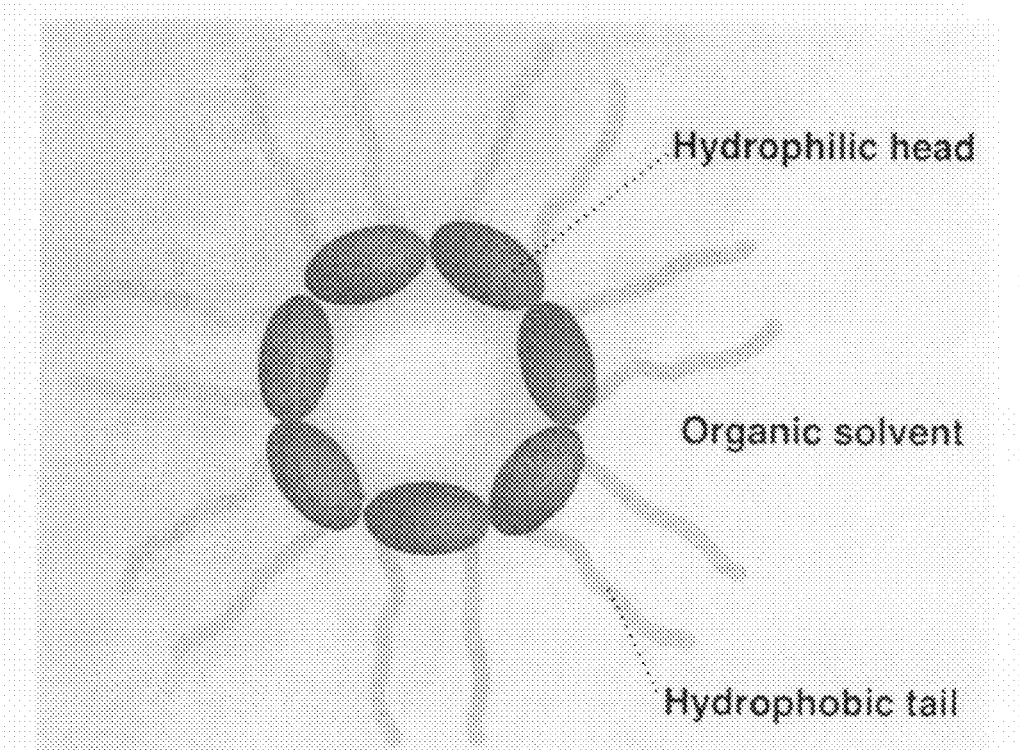
FIG. 17 shows scheme of a micelle formed by phospholipids in an organic solvent.

Micelle formation is essential for the absorption of fat-soluble vitamins and complicated lipids within the human body. Bile salts formed in the liver and secreted by the gall bladder allow micelles of fatty acids to form. This allows the absorption of complicated lipids (e.g., lecithin) and lipid soluble vitamins (A, D, E and K) within the micelle by the small intestine. FIG. 16 shows a schematic of a micelle formed by phospholipids in an aqueous solution, whereas FIG. 17 shows a schematic of a micelle formed by phospholipids in an organic solvent. In one embodiment, either scheme of micelles may be feasible to function as a drug delivery vehicle or be encapsulated in a nanoparticle formulation as disclosed in the present invention.

Example No. 20

Emulsifying Process for Micelles Formation

An emulsion is a mixture of two or more immiscible (unblendable) liquids. One liquid (the dispersed phase) is dispersed in the other (the continuous phase). Many emulsions are oil/water emulsions, with dietary fats being one common type of oil encountered in everyday life. Examples of emulsions include butter and margarine, milk and cream, and vinaigrettes; the photo-sensitive side of photographic film, magmas and cutting fluid for metal working. In butter and margarine, fat surrounds droplets of water (a water-in-oil emulsion). In milk and cream, water surrounds droplets of fat (an oil-in-water emulsion). In certain types of magma, globules of liquid NiFe may be dispersed within a continuous phase of liquid silicates. Emulsification is the process by which emulsions are prepared.

Emulsions are thermodynamically unstable liquid/liquid dispersions that are stabilized, in general, by surfactants. Surfactants are usually added to emulsion systems, assembling in the interface of the emulsion droplets, thus providing a protective membrane that prevents the droplets from flocculating or coalescing and thus enhancing the droplets formation and stability. Emulsion dispersion is not about reactor blends for which one polymer is polymerized from its monomer in the presence of the other polymers; emulsion dispersion is a novel method of choice for the preparation of homogeneous blends of thermoplastic and elastomer. In emulsion dispersion system the preparation of well-fined polymers droplets maybe acquired by the use of water as dispersing medium. The surfactant molecules adsorb on the surface of emulsion by creating a dispersion of droplets, which reduces interfacial tension and retards particle flocculation during mixing. The molecules of surfactant have polar and non-polar parts which act as an intermediary to combine polar and non-polar polymers; the intermolecular interactions between the polar and the non-polar polymer segments resemble the macroscopic hydrocarbon-water interface.

Emulsions tend to have a cloudy appearance, because the many phase interfaces (the boundary between the phases is called the interface) scatter light that passes through the emulsion. Emulsions are unstable and thus do not form spontaneously. Energy input through shaking, stirring, homogenizing, or spray processes are needed to form an emulsion. Over time, emulsions tend to revert to the stable state of the phases comprising the emulsion. Surface-active substances (surfactants) can increase the kinetic stability of emulsions greatly so that, once formed, the emulsion does not change significantly over years of storage. Vinaigrette is an example of an unstable emulsion that will quickly separate unless shaken continuously. This phenomenon is called coalescence, and happens when small droplets recombine to form bigger ones.

Emulsions are part of a more general class of two-phase systems of matter called colloids. Although the terms colloid and emulsion are sometimes used interchangeably, emulsion tends to imply that both the dispersed and the continuous phase are liquid. There are three types of emulsion instability: flocculation, where the particles form clumps; creaming, where the particles concentrate towards the surface (or bottom, depending on the relative density of the two phases) of the mixture while staying separated; and breaking and coalescence where the particles coalesce and form a layer of liquid. Whether an emulsion turns into a water-in-oil emulsion or an oil-in-water emulsion depends on the volume fraction of both phases and on the type of emulsifier. Generally, the Bancroft rule applies: emulsifiers and emulsifying particles tend to promote dispersion of the phase in which they do not dissolve very well; for example, proteins dissolve better in water than in oil and so tend to form oil-in-water emulsions (that is they promote the dispersion of oil droplets throughout a continuous phase of water).

The basic color of emulsions is white. If the emulsion is dilute, the Tyndall effect will scatter the light and distort the color to blue; if it is concentrated, the color will be distorted towards yellow. This phenomenon is easily observable on comparing skimmed milk (with no or little fat) to cream (high concentration of milk fat). Microemulsions and nanoemulsions tend to appear clear due to the small size of the disperse phase.

An emulsifier (also known as an emulgent) is a substance that stabilizes an emulsion, frequently a surfactant. Examples of food emulsifiers are egg yolk (where the main emulsifying chemical is lecithin), honey, and mustard, where a variety of chemicals in the mucilage surrounding the seed hull act as emulsifiers; proteins and low-molecular weight emulsifiers are common as well. In some cases, particles can stabilize emulsions as well through a mechanism called Pickering stabilization. Both mayonnaize and Hollandaise sauce are oil-in-water emulsions that are stabilized with egg yolk lecithin. Detergents are another class of surfactant, and will physically interact with both oil and water, thus stabilizing the interface between oil or water droplets in suspension. This principle is exploited in soap to remove grease for the purpose of cleaning. A wide variety of emulsifiers are used in pharmacy to prepare emulsions such as creams and lotions. Common examples include emulsifying was, cetearyl alcohol, polysorbate 20, and ceteareth 20.

Sometimes the inner phase itself can act as an emulsifier, and the result is nanoemulsion—the inner state disperses into nano-size droplets within the outer phase. A well-known example of this phenomenon, the ouzo effect, happens when water is poured in a strong alcoholic anize-based beverage, such as ouzo, pastis, arak or raki. The anisolic compounds, which are soluble in ethanol, now form nano-sized droplets and emulgate within the water. The color of such diluted drink is opaque and milky.

Microemulsions are clear, stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o). In ternary systems such as microemulsions, where two immiscible phases (water and 'oil') are present with a surfactant, the surfactant molecules may form a monolayer at the interface between the oil and water, with the hydrophobic tails of the surfactant molecules dissolved in the oil phase and the hydrophilic head groups in the aqueous phase. As in the binary systems (water/surfactant or oil/surfactant), self-assembled structures of different types can be formed, ranging, for example, from (inverted) spherical and cylindrical micelles to lamellar phases and discontinuous microemulsions, which may coexist with predominantly oil or aqueous phases.

The microemulsion region is usually characterized by constructing ternary-phase diagrams. Three components are the basic requirement to form a microemulsion: an oil phase, an aqueous phase and a surfactant. If a cosurfactant is used, it may sometimes be represented at a fixed ratio to surfactant as a single component, and treated as a single "pseudo-component". The relative amounts of these three components can be represented in a ternary phase diagram. Gibbs phase diagrams can be used to show the influence of changes in the volume fractions of the different phases on the phase behavior of the system. The three components composing the system are each found at an apex of the triangle, where their corresponding volume fraction is 100%. Moving away from that corner reduces the volume fraction of that specific component and increases the volume fraction of one or both of the two other components. Each point within the triangle represents a possible composition of a mixture of the three components or pseudo-components, which may consist (ideally, according to the Gibbs' phase rule) of one, two or three phases. These points combine to form regions with boundaries between them, which represent the "phase behavior" of the system at constant temperature and pressure.

Some aspects of the invention provide a formulation of liposome micelles and methods of formulating micelles, the micelles comprising a basic structure as described above and at least one compound or agent enclosed within. In one embodiment, the compound can be a thermal triggered phase-transition compound. In another embodiment, the agent can be hydrophobic or lipophilic agent. In another embodiment, the agent can be a cancer drug. In general, the micelles of the present invention may also be referred as 'bioactive micelles'. The micelles are generally less than about a few hundred nanometers, preferably less than about 20 nanometers, and most preferably less than about 10 nanometers.

Liposomes are artificially prepared vesicles made of lipid bilayer. Liposomes can be filled with drugs, and used to deliver drugs for cancer and other disease. Liposomes can be prepared by disrupting biological membranes, for example by conication. Liposomes can be composed of naturally-derived phospholipids with mixed lipid chains (like egg phosphatidylethanolamine) or other surfactants. Liposomes should not be confused with micelles and reverse micelles composed of monolayers. Liposomes are composite structures made of phospholipids and may contain small amounts of other molecules. Though liposomes can vary in size from low micrometer range to tens of micrometers, unilamellar liposomes are typically in the lower size range with various targeting ligands attached to their surface allowing for their surface-attachment and accumulation in pathological areas for treatment of disease. Another interesting property of liposomes is their natural ability to target cancer. The endothelial wall of all healthy human blood vessels is encapsulated by endothelial cells that are bound together by tight junctions. These tight junctions stop any large particles in the blood from leaking out of the vessel. Tumor vessels do not contain the same level of seal between cells and are diagnostically leaky. This ability is known as the Enhanced Permeability and Retention effect. Liposomes of certain sizes, typically less than about 200 nm, can rapidly enter tumour sites from the blood, but are kept in the bloodstream by the endothelial wall in healthy tissue vasculature. Anti-cancer drugs such as Doxorubicin (Doxil), Camptothecin and Daunorubicin (Daunoxome) are currently being marketed in liposome delivery systems. The thermal triggered phase-transition compound inside a liposome delivery system, after entering a cancer cell, functions to abruptly blow up the cancer cell for physical cancer therapy.

Formation of liposomes and nanoliposomes is not a spontaneous process. Lipid vesicles are formed when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes, which have many layers like an onion. Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for human use.

Some aspects of the invention provide a pharmaceutical composition of nanoparticles, the nanoparticles consisting of a positively charged chitosan, a negatively charged substrate, optionally a zero-charge compound, and liposome micelles. FIG. 15 shows a CS-γ-PGA chitosan-shelled nanoparticle having positive surface charges and the bioactive agent (a thermal triggered phase-transition compound) being associated in micelles before being encapsulated in nanoparticles.

Example No. 21

Thermal Triggered Phase-Transition Liposomes for Physical Cancer Therapy

Liposome micelles are manufactured by mixing a thermal triggered phase-transition compound (e.g., ammonium bicarbonate or other suitable compound) into liposome material. In one embodiment, the liposome material is comprised of HSPC (L-α-phosphatidylcholine, hydrogenated), which is a non-thermal responsible material serving as the base forming material, DOTMA (N-[1-(2,3-dioleyloxy)propyl]-N,N,N-trimethylammonium chloride) as an enhancer to increase cell uptake, and/or cholesterol ((10R,13R)-10,13-dimethyl-17-(6-methylheptan-2-yl)-2,3,4,7,8,9,11,12,14,15,16,17-dodecahydro-1H-cyclopenta[α]phenanthren-3-ol) as a stabilizer for liposome. In one exemplary embodiment, the molar ratio of HSPC:cholesterol:DOTMA of the liposome material is in the range of 6:4:0.5. The external surface of liposome micelles of the invention may be positive charged and have an average size of about 300 nm.

At room temperature, ammonium bicarbonate is a white, crystalline powder. Ammonium bicarbonate decomposes at 36 to 60° C. into ammonia, carbon dioxide, and water vapor in an endothermic process with rapid volume increase as shown below:

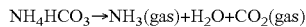

$$NH_4HCO_3 \rightarrow NH_3(gas) + H_2O + CO_2(gas)$$

The average liposome nanoparticle has been shown to be about 1200 nm after rapid decomposition of ammonium bicarbonate inside the nanoparticle; though the exploded nanoparticle is no longer in perfect spherical shapes. In one embodiment, the ammonium bicarbonate compound in the liposome nanoparticle formulation is a solid compound. Other thermal triggered phase-transition biocompatible compounds (for example, ammonium carbonate, ammonium sesquecarbonate, and the like) may be used in this liposome particle formulation. As used herein, the phrase "a thermal triggered phase-transition compound" means a temperature sensitive gaseous precursor, which denotes a solid or liquid compound that forms a gas following a change in temperature. In one embodiment, the compound may include the sublimable compound, wherein sublimation is the transition of a substance from the solid phase to the gas phase without passing through an intermediate liquid phase. Sublimation requires additional energy and is an endothermic change.

Some aspects of the invention relate to a pharmaceutical composition of liposome-shelled nanoparticles composed of at least one thermal triggered or triggerable phase-transition compound and at least one cancer drug. In clinical applications, the liposome-shelled nanoparticles are benign to a body as long as the liposome shell is intact. After the liposome-shelled nanoparticles are delivered to an animal subject following one of proposed endocytosis pathways (see FIG. 19, sources: *Nature Cell Biology Letter* 1 (2006)), some nanoparticles are heated to trigger phase transition of the loaded phase-transition compound and to cause physical damage of cancer cells as means for physical cancer therapy. Furthermore, the liposome-shelled nanoparticles may further comprise a cancer drug as means for a dual physical and biochemical cancer treatment.

The energy source for causing the phase transition of the enclosed 'at least one thermal triggered phase-transition compound' can be supplied from outside the animal subject toward the cancer or tumor cells. In one embodiment, the energy is applied via a radiofrequency catheter that contacts the target cancer cells in situ. In another embodiment, the ultrasound energy is applied through an intravascular ultrasound catheter. In another embodiment, the energy is provided via an external ultrasound system as a result of the ultrasound-induced hyperthermia, particularly with a high-intensity focused ultrasound (HIFU), toward the cancer cells. HIFU is a highly precise medical procedure using high-intensity focused ultrasound to heat and destroy pathogenic tissue rapidly. It is one modality of therapeutic ultrasound, and, although it induces hyperthermia, it should not be confused with this technique, which heats much less rapidly and to much lower therapeutic temperatures (in general <45° C.). In still another embodiment, the energy can be supplied via electromagnetic means toward the phase-transition compound from outside the animal subject. In an alternate embodiment, iron-containing quantum dots or tiny particles may be encapsulated within the liposome particles of the present invention. An external ultrasonic energy source could be applied to the iron-containing particles to provide heat to the phase-transition compound for blowing up the cancer cells.

In one embodiment, the liposome portion of the liposome nanoparticles is less thermal sensitive than the thermal triggerable phase-change compound of the liposome nanoparticles. In another embodiment, the thermal energy source for causing the phase transition of the encapsulated 'at least one thermal triggered phase-transition compound' is configured to be insufficient to cause any thermal damage to the liposome portion of the liposome nanoparticles of the present invention.

Some aspects of the invention relate to a pharmaceutical composition of liposome-shelled nanoparticles composed of at least one thermal triggered or triggerable phase-transition compound and at least one cancer targeting moiety as means for a dual function of cell targeting and physical cancer therapy.

Some aspects of the invention relate to a method of cell treating a cancer or tumor cell of an animal subject, comprising steps of: (a) providing a pharmaceutical composition of nanoparticles, wherein the nanoparticles comprise liposome and at least one thermal triggered phase-transition compound; (b) lodging the nanoparticles in the cancer or tumor cell in situ of the animal subject; and (c) supplying thermal energy to the at least one thermal triggered phase-transition compound, wherein the thermal energy is sufficient to cause a phase transition of the thermal triggered phase-transition compound. In one embodiment, the cell is a liver cell. In another embodiment, at least a portion of the nanoparticles comprises a hydrophilic outer shell or a hydrophobic outer shell.

Some aspects of the invention provide a method of cell treatment in an animal subject, comprising steps of: (a) providing a pharmaceutical composition of nanoparticles, wherein the nanoparticles comprise liposome and at least one thermal triggerable phase-transition compound; (b) lodging the nanoparticles in the cell in situ of the animal subject; and (c) supplying thermal energy to the at least one thermal triggerable phase-transition compound, wherein the thermal energy is sufficient to cause a phase transition of the thermal triggerable phase-transition compound.

Some aspects of the invention relate to a method of treating a cancer or tumor cell by providing a pharmaceutical composition of liposome nanoparticles of the present invention to an animal subject, wherein nanoparticles are further loaded with at least one bioactive agent. In one embodiment, the at least one bioactive agent is an anticancer drug, paclitaxel, a chemotherapy component, a deoxyribonucleic acid, or a small interfering ribonucleic acid.

Example No. 22

Imaging Drug Release by FRET

Chitosan (CS), a cationic polysaccharide, has been used extensively for various biomedical applications. It is known that the pKa of CS is approximately 6.5, and the charged state and physiochemical properties of CS are substantially influenced by its environmental pH value. In aqueous media at pH 7.4, CS forms dissociated precipitates because the aggregation of CS polymers occurs too rapidly and locally. To enhance the intermolecular contact of CS molecules while retaining their pH-sensitivity, a hydrophobic palmitoyl group was conjugated onto the free amine groups of CS, N-palmitoyl CS(NPCS). NPCS is a comblike polyelectrolyte characterized by the presence of alternating charges (protonated amine groups) and hydrophobic side chains (palmitoyl groups, FIG. 20a). Through a proper balance between charge repulsion and hydrophobic interaction, this associated polyelectrolyte can undergo a rapid hydrogelation triggered simply by its environmental pH within a narrow pH range.

The cationic polysaccharide chitosan has been extensively studied for oral drug delivery. Representatives of the modified chitosan are N-trimethyl chitosan, thiolated chitosan, carboxymethyl chitosan and derivatives, hydrophobic chitosan, chitosan succinate and phthalate, PEGylated chitosan and chitosan-enzyme inhibitor conjugates. However, the N-palmitoyl CS(NPCS) is unique and exhibits special features such as: a comblike polyelectrolyte, having alternating charges (protonated amine groups), having hydrophobic side chains, and able to undergo a rapid hydrogelation triggered simply by its environmental pH within a narrow pH range.

In diluted aqueous media, NPCS polymers are able to self-assemble into nanoparticles (NPs), due to the hydrophobic interaction between their conjugated palmitoyl groups. NPs made from hydrophobically-modified polymers have been used as a drug-delivery vehicle; previous studies have reported that they could accumulate passively in the tumor tissue for therapeutic applications.

A variety of forms of endocytosis have been demonstrated in the cellular uptake of polyplexes. Current evidences suggest that endocytosis is the main mode of CS-based NPs entering into the cells. In one embodiment, doxorubicin (DOX) is encapsulated in pH-responsive NPCS NPs as an anticancer delivery device. The drug release mechanism from delivery carriers was mostly conducted in vitro in simulated release media. Using polymeric micelles loaded with DOX, the intracellular drug release behavior was previously reported. One aspect of the invention is to disclose the fate of test particles with respect to their intracellular localization and drug release mechanism enabling rational design of drug carriers.

The prepared NPs were characterized using dynamic light scattering (DLS) and their cytotoxicity was evaluated by the MTT (3-(4,5-dimethylthiazol-2-yl)-2,5-diphenyl tetrazolium bromide) assay. The conformation transition of NPCS NPs in response to the environmental pH was modeled by molecular dynamic (MD) simulations. The emission spectra and dual-emission images of fluorescent DOX-loaded Cy5-NPCS NP suspensions at distinct pH values were determined by a fluorescence spectrometer and an In Vivo Imaging System (IVIS), respectively. The in vitro release profile of DOX from Cy5-NPCS NPs was examined in different release media; their intracellular drug release mechanism was monitored/imaged using Förster resonance energy transfer (FRET).

Cyanine (Cy) is a non-systematic name of a synthetic dye family belonging to polymethine group. Cyanines have many uses as fluorescent dyes, particularly in biomedical imaging. Depending on the structure, they cover the spectrum from IR to UV. Cy3 and Cy5 are reactive water-soluble fluorescent dyes of the cyanine dye family. Cy3 dyes are green (550 nm excitation, ~570 nm emission and therefore appear green), while Cy5 is fluorescent in the red region (~650/670 nm) but absorbs in the orange region (~649 nm). They are usually synthesized with reactive groups on either one or both of the nitrogen side chains so that they can be chemically linked to either nucleic acids or protein molecules. Labeling is done for visualization and quantification purposes. They are used in a wide variety of biological applications including comparative genomic hybridization and in gene chips, which are used in transcriptomics. They are also used to label proteins and nucleic acid for various studies including proteomics and RNA localization.

Stimuli-responsive NPs serve as a drug-delivery vehicle for therapeutic applications. Such nanosized particles could store and protect various drugs from surrounding environment, and their stimuli-responsive release of nanoparticle contents may significantly enhance therapeutic efficacy and minimize possible side effects. One object of the invention is to intracellularly monitor and/or image the drug release characteristics of a pH-responsive NPCS NP system using FRET principle. FRET involves the non-radiative transfer of energy from an excited state fluorophore (donor) to a second fluorophore (acceptor) in a close proximity (typically <10 nm apart). Consequently, FRET is capable of resolving molecular interactions or a single molecular event such as its conformational transition with a spatial resolution far exceeding what is available through the optics of conventional light microscopes.

Figure 20B:
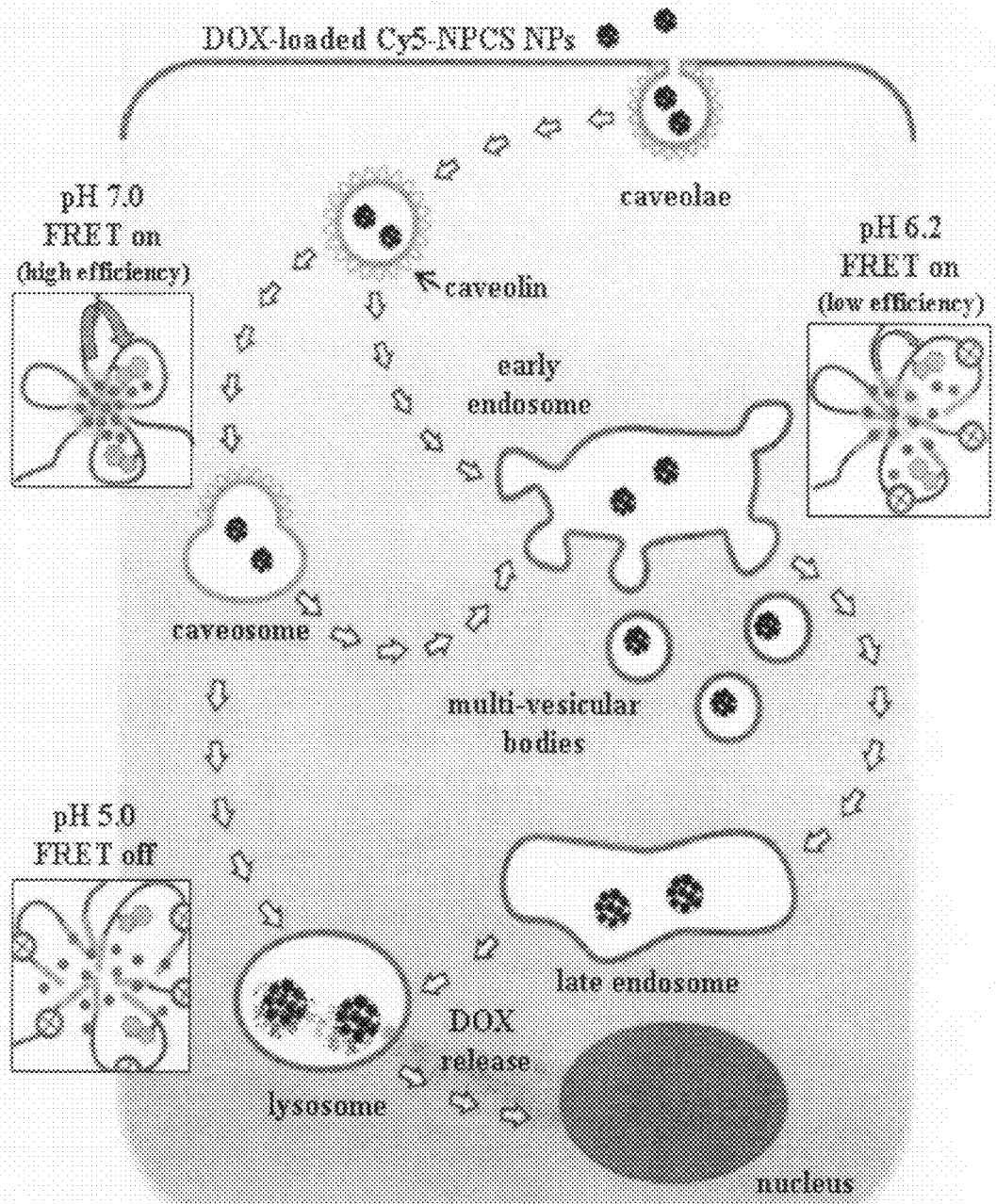
FIG. 20 shows schematic illustrations of the NPCS nanoparticles; (a) pH-responsive doxorubicin (DOX)-loaded nanoparticles (NPs), made of N-palmitoyl chitosan bearing a Cy5 moiety (Cy5-NPCS), were prepared as an anticancer delivery device; (b) using the technique of Förster resonance energy transfer (FRET), the drug release behavior of DOX-loaded Cy5-NPCS NPs as being monitored/imaged intracellularly.

The scientific concept of the invention is schematically illustrated in FIG. 20a and FIG. 20b. NPCS was prepared by conjugating a hydrophobic palmitoyl group onto the free amine groups of CS. Here a tiny amount of Cy5 moiety (FRET acceptor) is attached to the backbone of NPCS to yield Cy5-NPCS (DS, ca. 0.4%). In aqueous solution containing DOX (FRET donor), the hydrophobic palmitoyl groups tend to form local aggregates that act as physical crosslinks between Cy5-NPCS polymers, thus producing DOX-loaded Cy5-NPCS NPs spontaneously. A representative TEM micrograph of the prepared NPs is shown in FIG. 20a. At pH≧7.0, the distance of DOX molecules and Cy5 moieties in NPs was close enough to each other for energy transfer (i.e., FRET on). In contrast, at low pH where the amine groups on Cy5-NPCS were protonated, the polymer chains in NPs expanded due to the charge repulsion; thus DOX and Cy5 became inaccessible to each other for energy transfer (i.e., FRET off). As a result, the ability of Cy5-NPCS to self-associate offers the close proximity between the donor (DOX) and the acceptor (Cy5) required for FRET, while the pH-driven structure transition prescribes the on-to-off switch of the energy transfer.

Materials and Methods for Nanoparticles

CS (viscosity 5 mPa·s, 0.5% in 0.5% acetic acid, MW 50 kDa) with a degree of deacetylation of approximately 85% was purchased from Koyo Chemical Co. Ltd. (Tokyo, Japan). Palmitic acid N-hydroxysuccinimide (NHS) ester and DOX hydrochloride were obtained from Sigma-Aldrich (St. Louis, Mo., USA). NHS-functionalized cyanine 5 (Cy5-NHS) and fluorescein (fluorescein-NHS) were acquired from Amersham Biosciences (Piscataway, N.J., USA) and Thermo Scientific (Chicago, Ill., USA), respectively. All other chemicals and reagents used were of analytical grade.

The procedure used for the synthesis of NPCS with different degrees of substitution (DS; NPCS-5%, NPCS-10%, NPCS-15% and NPCS-20%) was described in details in our previous report [Biomaterials 2009; 30:4877-4888]. A mixture of CS (1 g) and aqueous acetic acid (50 mL, 1% w/v) was stirred for 24 hours to ensure total solubility. The pH was adjusted to 6.0 by slow addition of 1N NaOH and the final volume of CS solution was 100 mL. A solution of palmitic acid N-hydroxysuccinimide ester (0.1, 0.2, 0.3 or 0.4 g) in absolute ethanol was added drop-wise to the CS solution at 98° C. and reacted for 36 hours. Subsequently, the prepared solution was cooled at room temperature, added acetone, and precipitated by adjusting its pH value to 9.0. The precipitate (NPCS) was then filtered, washed with an excess of acetone and air-dried. The synthesized NPCS was analyzed by the proton nuclear magnetic resonance ($^1$H-NMR) and Fourier transformed infrared (FT-IR) spectroscopy. Additionally, the degree of substitution (DS) on NPCS was determined by the ninhydrin assay and the potassium polyvinylsulfate (PVSK) titration method.

Cy5-labeled NPCS (Cy5-NPCS) and fluorescein-labeled NPCS (fluorescein-NPCS) were synthesized. Briefly, a solution of Cy5-NHS or fluorescein-NHS in dimethyl sulfoxide (DMSO, 1 mg/mL) was prepared and added gradually into an aqueous NPCS (2 mg/mL) while stirring; the weight ratio of fluorescent dye to NPCS was kept at 1:50 (w/w). The reaction was maintained at pH 5.5 and stirred continuously for 12 hours in the dark. To remove the unconjugated fluorescent dyes, the synthesized Cy5-NPCS and fluorescein-NPCS were dialyzed in the dark against deionized (DI) water and replaced on a daily basis until no fluorescence (Cy5 or fluorescein) was detected in the supernatant. The resultant Cy5-NPCS and fluorescein-NPCS were then lyophilized in a freeze dryer.

Characteristics of Cy5-NPCS NPs

The synthesized Cy5-NPCS polymers with different DS were individually dissolved in 1% aqueous acetic acid and its pH value was adjusted to 4.0 by adding a few drops of 1N NaOH under magnetic stirring to form test NPs. The size distributions and zeta potential values of the prepared NPs at predetermined pH values (adjusted by phosphate buffer) were investigated using DLS (Zetasizer 3000HS, Malvern Instruments Ltd., Worcestershire, UK).

Preparation and Characterization of DOX-loaded Cy5-NPCS NPs

DOX was added into a Cy5-NPCS solution (in aqueous acetic acid); the weight ratio of DOX to Cy5-NPCS was 1:5. After stirring in the dark for 10 minutes, the pH of the mixture was adjusted to 7.4, and the mixture was stirred in the dark for another 20 minutes to form NPs. Subsequently, the mixture was dialyzed in the dark against DI water (pH 7.4) to remove free DOX in the solution. The morphology of the prepared NPs was examined by transmission electron microscopy (TEM, JEOL 2010F, Tokyo, Japan). The loading efficiency of DOX in NPs was determined by assaying the amount of free DOX in the supernatant using a fluorescence spectrometer (Spex FluoroMax-3, Horiba Jobin Yvon, Edison, N.J., USA).

Cytotoxicity of NPCS Nanoparticles

The cytotoxicity of test NPs that contain DOX was evaluated in vitro using the MTT assay; the group without any treatment was used as a control. HT1080 (human fibrosarcoma, ATCC CRL-121) cells were seeded in 12-well plates at $1\times10^5$ cells/well, allowed to adhere overnight and incubated with a growth medium [DMEM with fetal bovine serum (FBS), pH 7.4] containing test NPs at varying DOX concentrations (12.5, 25.0, 50.0 and 100.0 µg/mL). After 24 hours, test samples were aspirated and cells were incubated in the growth medium containing 1 mg/mL MTT reagent for an additional 4 hours; a 1000 µL of DMSO was added to each well to ensure solubilization of formazan crystals. Finally, the optical density readings were performed using a multiwell scanning spectrophotometer (Dynatech Laboratories, Chantilly, Va., USA) at a wavelength of 570 nm.

Cy5-NPCS with different DS in distinct pH environments form particles on the nanometer scale. In general, with increased DS, the diameter (FIG. 21a) and zeta potential value (FIG. 21b) of the prepared NPs decrease relatively, due to a stronger hydrophobic interaction between their palmitoyl side chains on NPCS and a lower degree of protonated amine groups. At low pH, the charge repulsion between the protonated amine groups on NPCS dominates, leading to the extension of polymer chains. Thus, only a fraction of the palmitoyl side chains are associated locally, resulting in a relatively swelling matrix structure. With increasing in pH, the electrostatic repulsion between NPCS polymers reduces appreciably due to the deprotonation of their amine groups; hence, the hydrophobic interaction between their palmitoyl side chains takes the control, causing a gradual reduction in the size of NPs. The transition from a swollen, highly charged structure at low pH to a condensed, weakly charged construction at high pH (or the pH-triggered NPCS conformational change) enabled the prepared NPs to act as a simple switch on-or-off in response to the changes in their environmental pHs.

In one embodiment, the drug loading efficiency in NPs increases significantly with increased DS of NPCS(NPCS-5%, 15.7%; NPCS-10%, 36.5%; NPCS-15%, 43.7%; and NPCS-20%, 49.7%). However, up to a critical DS (NPCS-20%), the sensitivity in particle size to the environmental pH becomes relatively poor (FIG. 21a) because of a strong association of the palmitoyl side chains between NPCS polymers. One aspect of the invention relates to NPs prepared with a content of NPCS up to 20%, preferably between 5 and 15%.

Cytotoxicity of DOX-Loaded Test NPs

Figure 22:
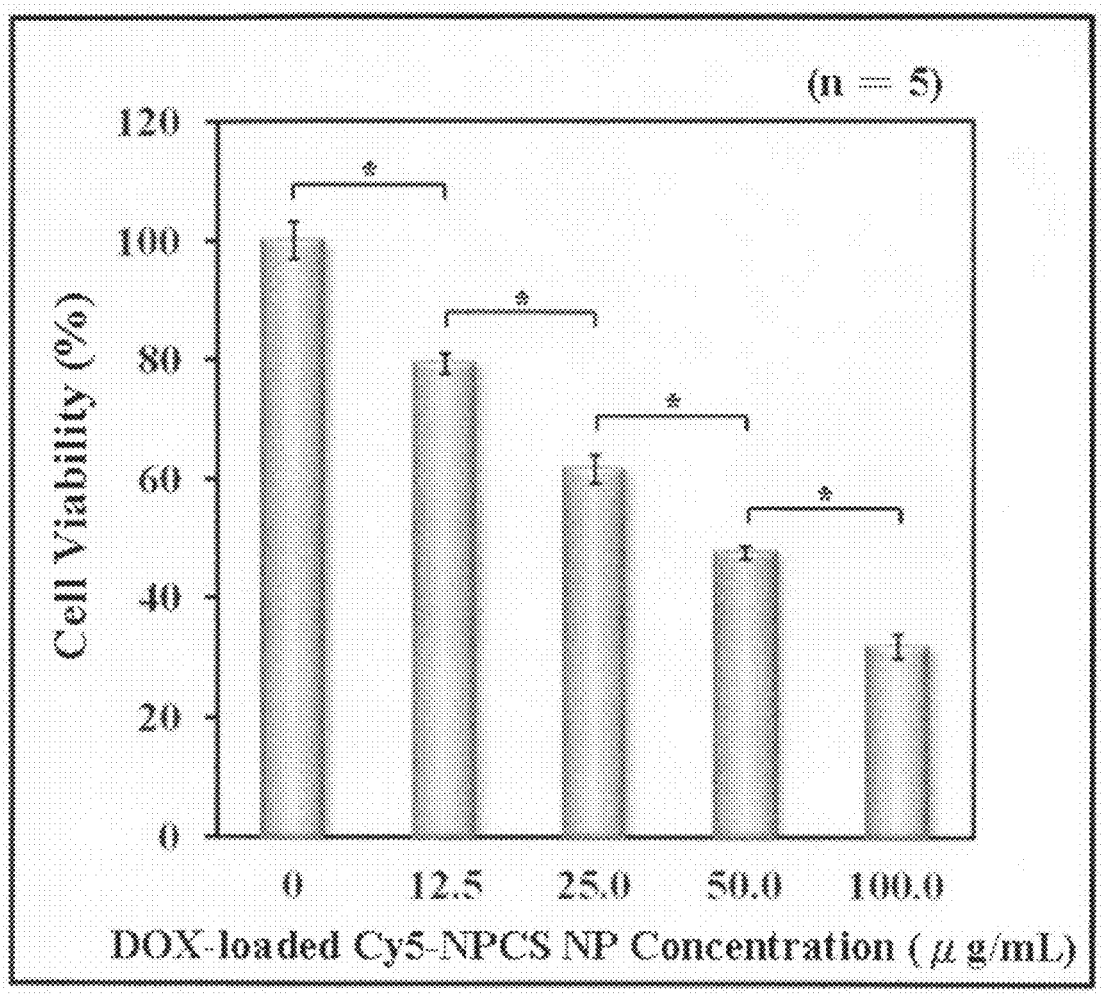
FIG. 22 shows the cell viability, obtained by the MTT assay, after being treated with doxorubicin (DOX)-loaded nanoparticles (NPs) at varying concentrations (n=5, *P<0.05).

DOX shows high antitumour activity and ranks among the most effective antitumor agents in clinical practice. To examine the cytotoxicity, we incubated HT1080 cells with DOX-loaded Cy5-NPCS NPs at varying concentrations for 24 hours; the viability of cells without any treatment was used as a control. After treatment, the mitochondrial activity of living cells was measured by the MTT assay. As shown in FIG. 22, the cell viability declines progressively when the concentration of test NPs is increased (P<0.05), and the $MTT_{50}$ value measured is approximately 50 µg/mL.

FRET Measurements

The emission spectra of the prepared fluorescent DOX-loaded Cy5-NPCS NP suspensions (100 µg/mL) at distinct pH values were determined by a fluorescence spectrometer. For FRET measurements, the donor (DOX) was excited at 485 nm and the emission spectra of the donor/acceptor were recorded at all wavelengths simultaneously. Dual-emission images of fluorescent NP suspensions at distinct pH environments were acquired using an IVIS (Xenogen, Alameda, Calif., USA). In the example, DOX-loaded Cy5-NPCS NP suspensions (100 µg/mL, 200 µL per well) were loaded in a 96-well plate. The plate was irradiated at a wavelength of 500±15 nm and then imaged with sequential emission filters (580±10 nm and 680±10 nm bandpass) to obtain unmixed DOX and Cy5 images.

Figure 21:
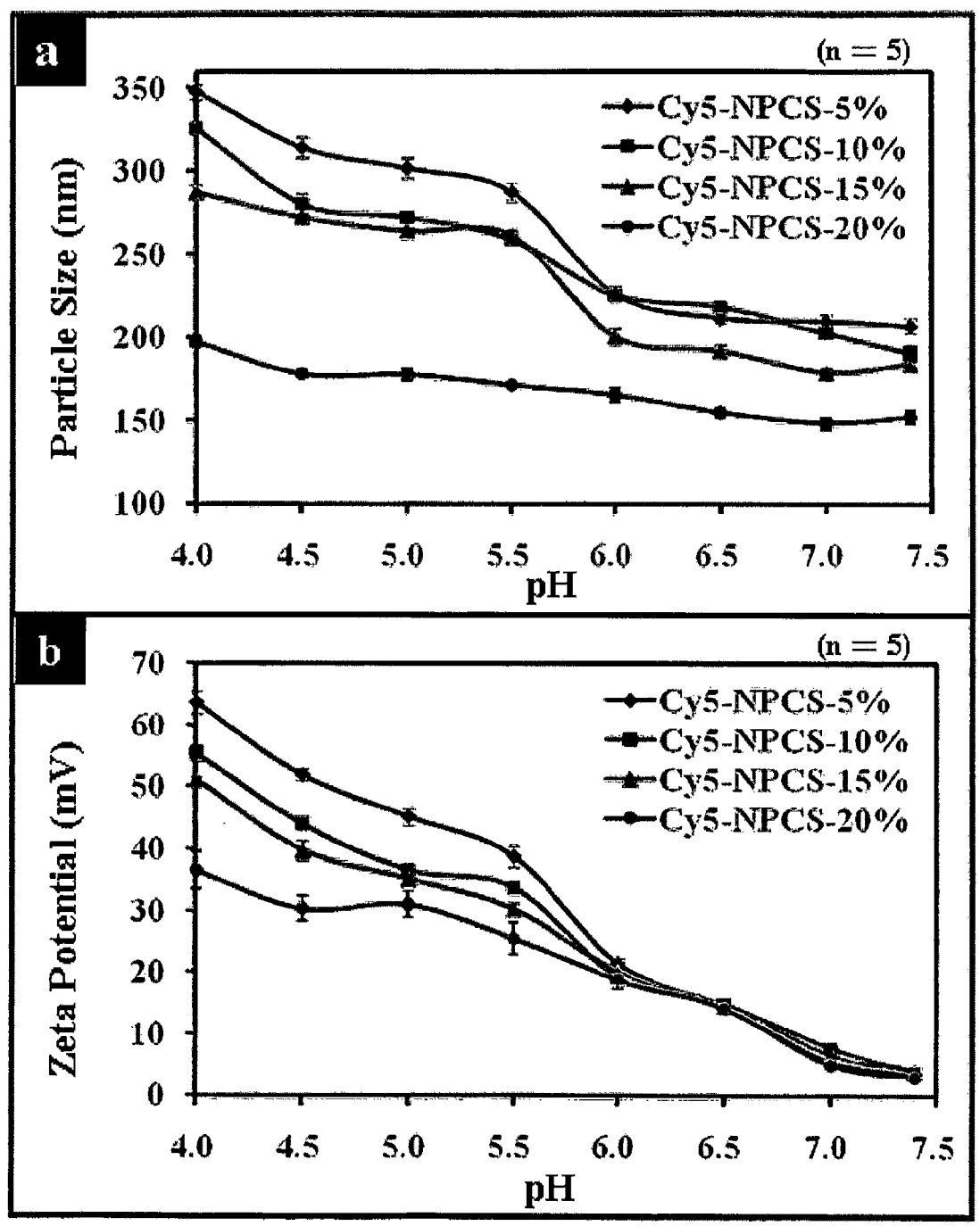
FIG. 21 shows the pH dependence of (a) the particle size and (b) the zeta potential value of test nanoparticles (NPs) prepared by Cy5-labeled N-palmitoyl chitosan (Cy5-NPCS) with different degrees of substitution (n=5).
Figure 23:
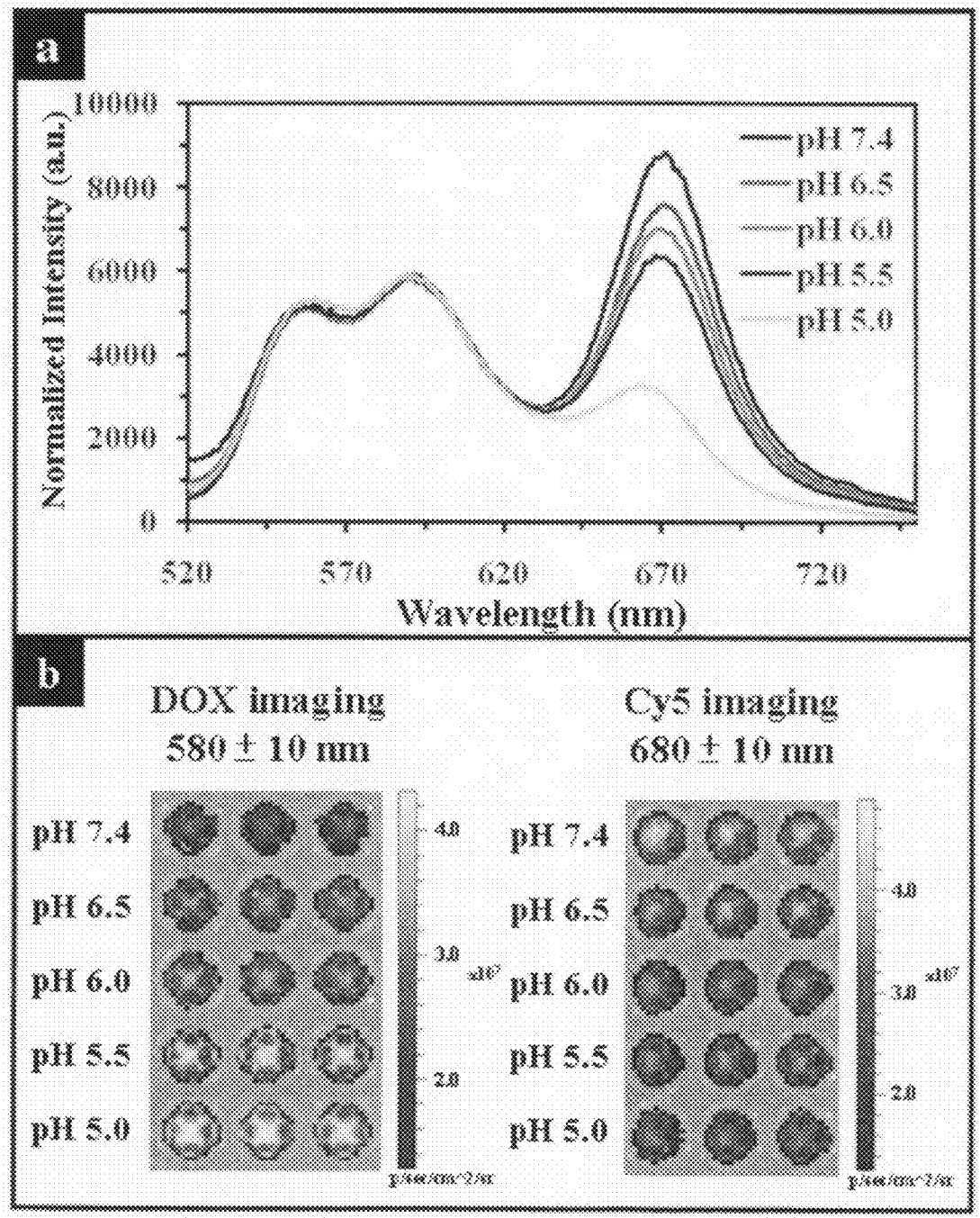
FIG. 23 shows (a) FRET spectra of DOX-loaded Cy5-NPCS NP suspensions, which were normalized to the maximum DOX donor peak around 590 nm, as a function of the environmental pH; (b) dual-emission images of DOX-loaded Cy5-NPCS NP suspensions, as a function of the environmental pH, obtained by an In Vivo Imaging System. The FRET spectra and dual-emission images were obtained by irradiating NP suspensions at 485 nm and 500±15 nm, respectively, corresponding to the excitation wavelength of the FRET donor, DOX.

The FRET spectra of aqueous DOX-loaded Cy5-NPCS NPs, which are normalized to the maximum DOX donor peak around 590 nm, as a function of the environmental pH are shown in FIG. 23a. All spectra are obtained by irradiating NP suspensions at 485 nm corresponding to the excitation wavelength of the FRET donor, DOX. With increased pH, sequential increase in the emission ratio of Cy5/DOX was observed due to an increase in FRET efficiency, indicating more energy being transferred from DOX to Cy5. The increase in FRET efficiency was consistent with an observation in the reduction in NP size in response to the increase in environmental pHs (FIG. 21a). FIG. 23b presents the dual-emission pH images obtained by IVIS. DOX and Cy5 images were acquired through 580 nm±10 nm and 680 nm±10 nm bandpass emission filters, respectively. When DOX-loaded Cy5-NPCS NP suspensions are excited at 500 nm±15 nm, the fluorescent intensity of DOX band gradually increases and that of Cy5 band decreases with decreased pH.

Molecular Dynamic Simulation

MD simulations of the conformation transition of DOX-loaded Cy5-NPCS NPs in response to their environmental pH were performed; simulations were accomplished with the program NAMD using parameters adapted from the CHARMM 27 force field. The models were minimized to remove unfavorable contacts, brought to 310 K by velocity resealing and equilibrated for 1 ns. Before any MD trajectory was run, 40 ps of energy minimization were performed to relax the conformational and structural tensions. This minimum structure was the starting point for the MD simulations. For this purpose, the molecule was embedded into a cubic simulation box of 80 Å. A cutoff distance of 12 Å was employed for the unbonded and electrostatic interactions. The heating process was performed from 0 to 310 K through Langevin damping with a coefficient of 10 $ps^{-1}$. A time step of 2 fs was employed for rescaling the temperature. After 20 ps heating to 310 K, equilibration trajectories of 1 ns were recorded, which provided the data for the structural and thermodynamic evaluations. The equations of motion are integrated with the Shake algorithm with a time step of 1 fs. Figures displaying atomistic pictures of molecules with hydrogen bonding is generated using UCSF Chimera.

Figure 24A:
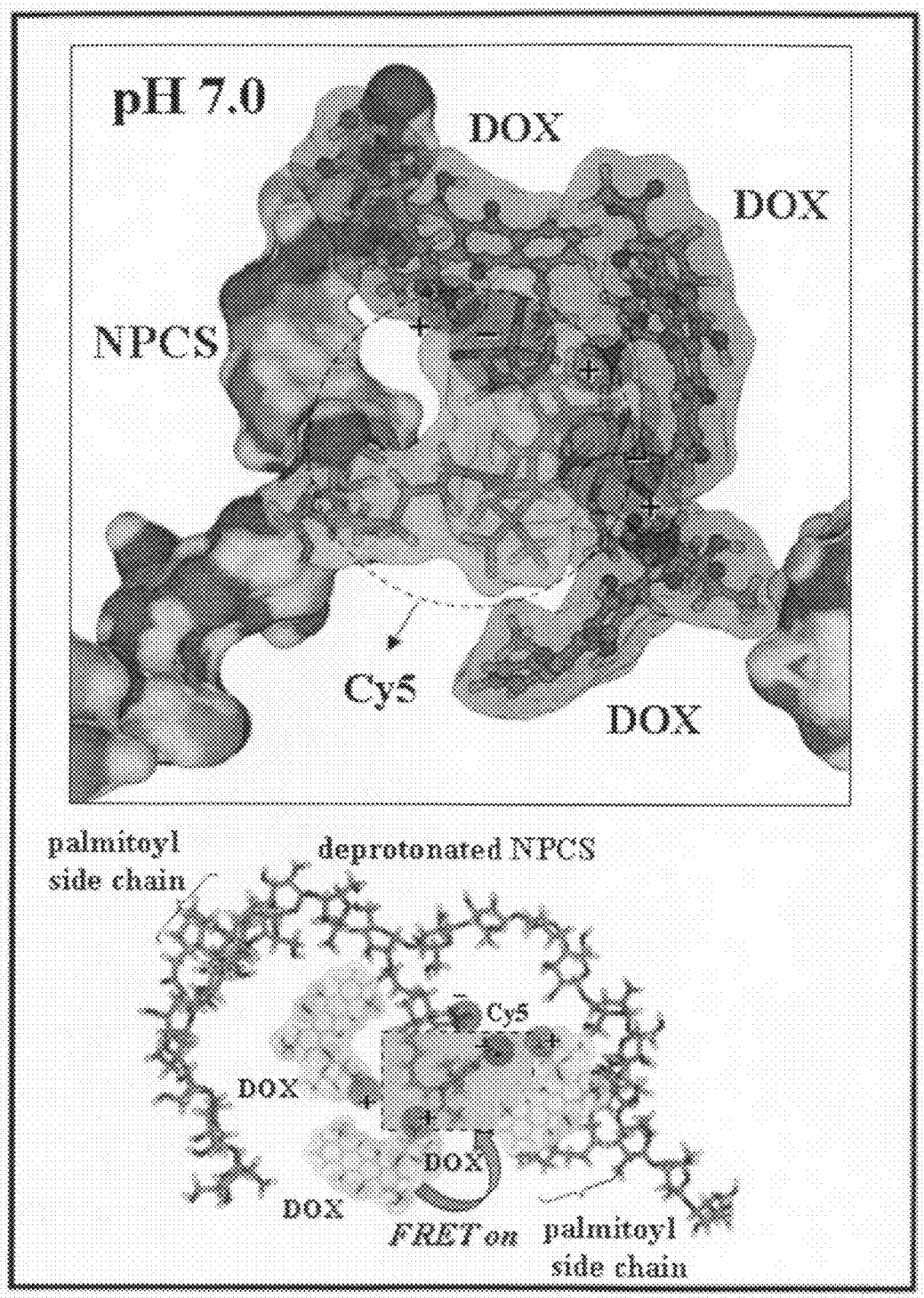

MD simulations were performed in a full-atom model to gain insight into the mechanism of drug release from DOX-loaded Cy5-NPCS NPs. At pH 7.0 (simulating the pH environment in the intracellular caveosomes), most amine groups on NPCS were in the form of $—NH_2$ because of deprotonation and the hydrophobic core of NPs can serve as microreservoirs for loading DOX (FIG. 24a and FIG. 24b). In this case, DOX (pKa=8.3) is positively charged and Cy5 negatively charged ($C_6H_5SO_3^-$, pKa=0.7); therefore, DOX molecules were in the close vicinity of Cy5 moieties, owing to an electrostatic interaction, for an efficient energy transfer (i.e., FRET on). At pH 5.0 (simulating the pH environment in the intracellular lysosomes), the amine groups on NPCS became protonated ($—NH_3^+$) and might therefore electrostatically interact with the negatively charged Cy5 moieties (FIG. 24 and FIG. 24b). In contrast, because of the electrostatic repulsion, DOX molecules were released from NPCS NPs and became inaccessible to the Cy5 moiety for energy transfer (i.e., FRET off).

Endocytosis Inhibition of NPCS Nanoparticles

To reveal the potential cellular uptake pathway of NPCS NPs, the interaction between NPCS NPs (fluorescein-labeled) and cell membranes was investigated, by treating cells with different chemical inhibitors and then analyzed by flow cytometry. HT1080 cells were seeded in 12-well plates at $1 \times 10^5$ cells/well and were allowed to adhere overnight. Subsequently, cells were pre-incubated with the following inhibitors individually at concentrations that were not toxic to the cells: 7 μg/mL of chlorpromazine, 500 nM wortamannin, 3 mM methyl-β-cyclodextrin (MβCD) or 200 μM genistein. Following the pre-incubation for 30 min, the inhibitor solutions were removed, and freshly prepared fluorescein-labeled NPCS NPs (10 μg/mL) in media containing the same inhibitor concentrations as those mentioned above were added and further incubated for 2 hours. After incubation, the cells were washed three times with phosphate buffered saline (PBS), detached by 0.025% trypsin/EDTA and then transferred to microtubes. Subsequently, cells were resuspended in PBS containing 1 mM EDTA and 2% FBS and fixed in 4% paraformaldehyde. Finally, the cells were introduced into a flow cytometer equipped with a 488-nm argon laser (Beckman Coulter, Fullerton, Calif., USA).

It has been reported that initial interaction between the cationic vectors and the negatively charged cell membranes is mediated by electrostatic interactions; the vectors are then likely taken up by the cells through endocytosis. To elucidate their potential endocytosis pathway, the interaction between NPCS NPs (fluorescein-labeled) and cell membranes was investigated by treating cells with different chemical inhibitors and then analyzed by flow cytometry; their counterparts in the absence of inhibitors were used as controls.

Figure 26:
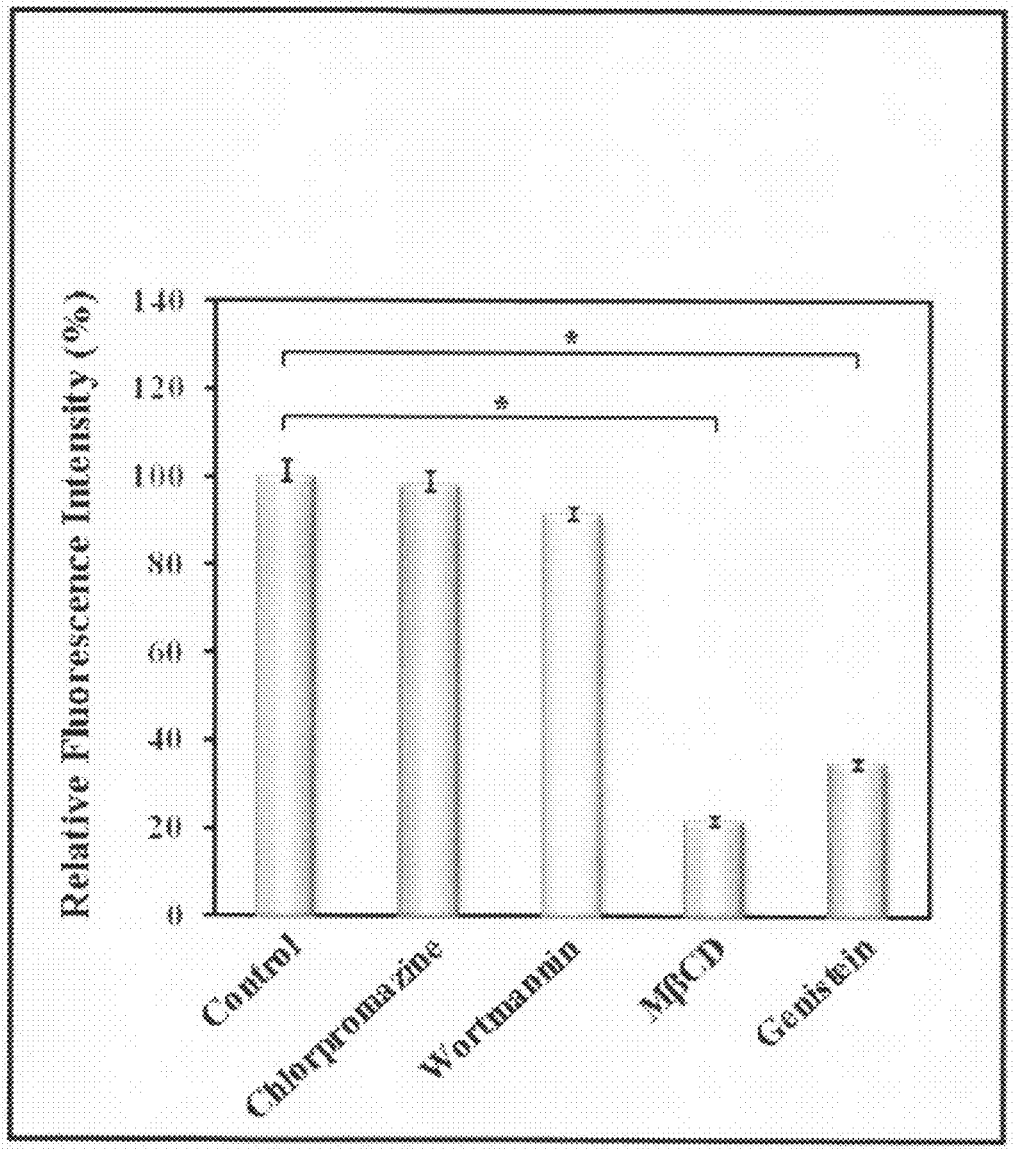
FIG. 26 shows effects of inhibitors on the internalization of NPCS nanoparticles (NPs) in the presence of chlorpromazine (7 µg/mL), wortmannin (500 nM), MβCD (methyl-β-cyclodextrin, 3 mM) or genistein (200 µM). Control: the counterpart in the absence of inhibitors (n=5, *P<0.05).

Inhibition of clathrin-mediated uptake was tested using the cationic amphiphilic drug chlorpromazine, which causes clathrin to accumulate in late endosomes, thereby inhibiting coated pit endocytosis. Wortmannin is a phosphatidyl inositol-3-phosphate inhibitor, which can inhibit macropinocytosis. As shown in FIG. 26, treatment with chlorpromazine or wortmannin did not result in a significant inhibition of uptake of NPCS NPs, indicating that neither clathrin-mediated endocytosis nor macropinocytosis was involved in the endocytosis. Methyl-β-cyclodextrin (MβCD, a water-soluble cyclic oligomer of glucopyranoside and an inhibitor of lipid rafts) and genistein (a tyrosine kinase inhibitor) are known to inhibit caveolae-mediated endocytosis, each acting by a different mechanism. As compared to the control, cells treated with MβCD or genistein significantly diminish the fluorescence intensity ($P<0.05$), an indication of caveolae-mediated endocytosis.

Endocytosis Pathway and Intracellular Trafficking

In one example, cells were treated with the Cy5-labeled NPCS NPs in the serum-free medium to study the intracellular trafficking of test NPs. After incubation at predetermined time points, cells were washed twice with the pre-warmed PBS before they were fixed in 4% paraformaldehyde. The fixed cells were investigated using the immunohistochemical stains to identify caveolae/caveosomes, early/late endosomes and lysosomes. The antibodies used in the study were polyclonal rabbit anti-caveolin-1 antibody (Cell Signaling Technology #3238, Beverly, Mass., USA), rabbit polyclonal anti-EEA1 antibody (Abcam #ab2900) and monoclonal mouse anti-LAMP2 antibody (Abcam #ab25631). The stained cells were counterstained to visualize nuclei by propidium iodide (PI, Sigma-Aldrich) and examined using CLSM (TCS SL, Leica, Germany).

In one embodiment, the extent of cellular uptake of NPs of NPCS significantly enhances with increased DS. The potential endocytosis pathway and intracellular trafficking of NPs of NPCS with a DS of 15% are investigated via a flow cytometer and a CLSM, respectively. In brief, the caveolae-mediated pathway played a major role in the internalization of NPCS NPs. Following the caveolae-mediated endocytosis, NPCS NPs trafficked within early endosomes, which matured into acidic late endosomes and lysosomes.

Free DOX molecules are known to enter cells via permeation through the cell membrane, while the drug-loaded NPs are generally internalized through an endocytosis pathway and thus localized in endocytic compartments. Following the entry of NPCS NPs via the caveolae-mediated pathway, the potential co-localization of test NPs and caveolae/caveosomes, early endosomes or late endosomes/lysosomes was investigated using a CLSM. Caveolae/caveosomes (pH 7.0) are characterized by the presence of a family of caveolin proteins including caveolin-1 (CAV1). After incubation for 30 min, the internalized NPs were found associated with CAV1-positive structures (caveosomes, in white) near the cell periphery. Subsequently, significant levels of NPs were found colocalized with early endosomes (EEA1, at 1 hour after); the early endosomes (pH 6.2) then matured into late endosomes, and then to lysosomes (pH 5.0) at longer incubation time points (1-4 hours, LAMP2). These results demonstrate that following the caveolae-mediated endocytosis, NPCS NPs trafficked within early endosomes, which matured into acidic late endosomes and lysosomes.

In Vitro DOX Release Study

The in vitro release profile of DOX from Cy5-NPCS NPs was examined by dialyzing the DOX-loaded NP suspension in different release media (PBS buffers at pH 7.0, 6.2, and 5.0) in the dark. Briefly, 2 mL of the DOX-loaded NP suspension (50 µg/mL) was dialyzed against 15 mL of buffer (MWCO: 12,000-14,000) and gently shaken in a thermostatic rotary shaker at 37° C., 100 rpm. Samples were removed at appropriate time intervals, and an equal amount of the same dissolution medium was added to maintain a constant volume. The amount of DOX released from test NPs was assayed by a fluorescence spectrometer (Spex FluoroMax-3, Horiba Jobin Yvon, Edison, N.J., USA) at 485 nm.

Figure 25:
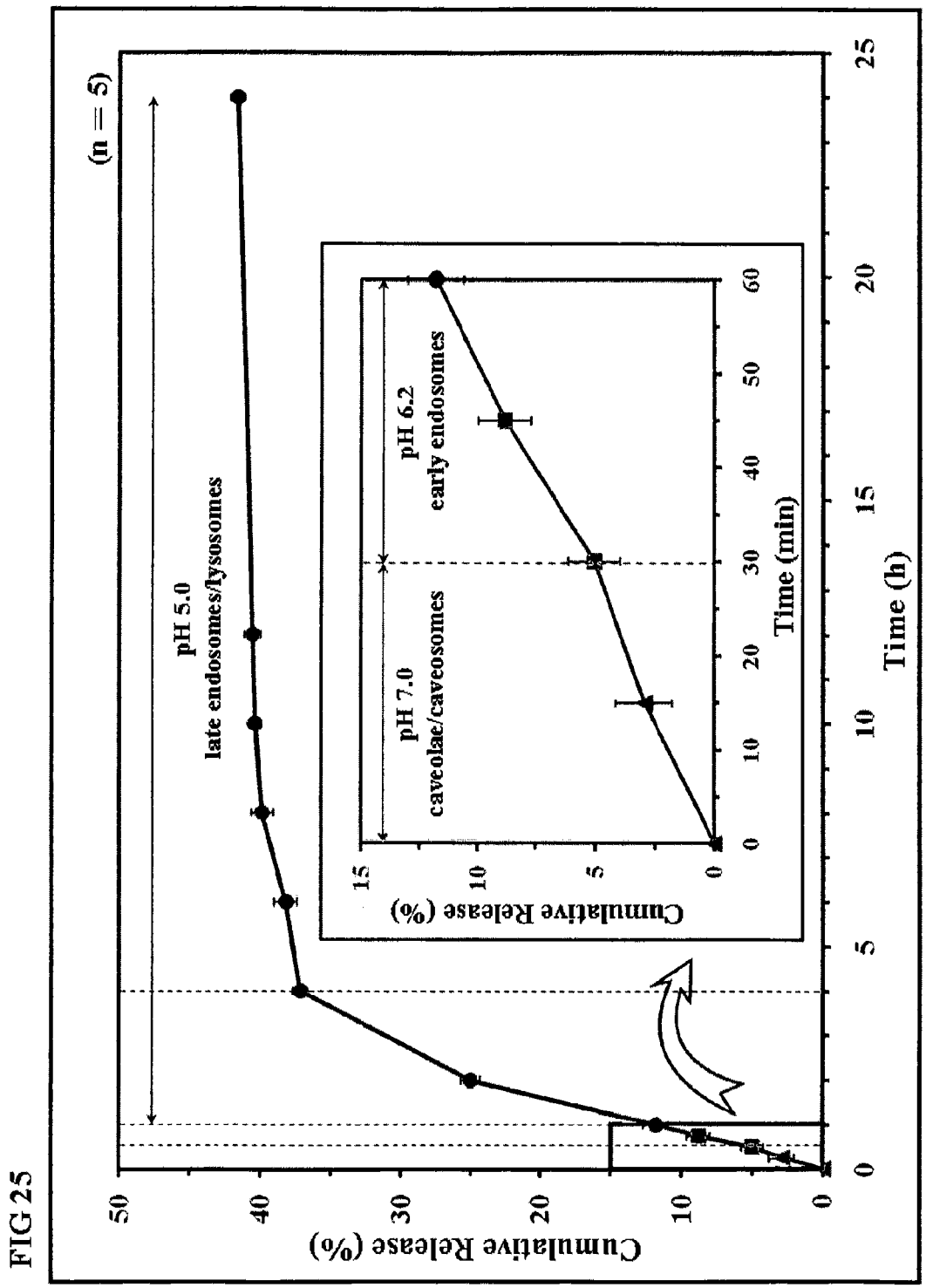
FIG. 25 shows in vitro drug release profile from DOX-loaded Cy5-NPCS nanoparticles (NPs) in different release media (PBS buffers at pH 7.0, 6.2 and 5.0) at 37° C. (n=5).

Results of the DOX release profile from test Cy5-NPCS NPs at pH 7.0, 6.2, and 5.0 (simulating the pH environments in the caveolae/caveosomes, early endosomes and late endosomes/lysosomes, respectively) are shown in FIG. 25. There was little release of DOX from test NPs in the pH environments of the caveolae/caveosomes (the first 30 min) and early endosomes (30 minutes to 1 hour). In contrast, a significant DOX release was found in the pH environment of the late endosomes/lysosomes (1-4 hour, $P<0.05$), showing that the release of DOX from Cy5-NPCS NPs was a pH dependent process due to a considerable increase of test NPs (FIG. 21a). This pH sensitive release behavior is of particular interest in achieving the intracellular DOX delivery.

Intracellular Monitoring/Imaging Drug Release Using FRET

To monitor the drug release from test NPs intracellularly, cells were treated with DOX-loaded Cy5-NPCS NPs (50 µg/mL) in the serum-free medium. After incubation at predetermined time intervals, cells were washed twice with the pre-warmed PBS before they were fixed in 4% paraformaldehyde. The fixed cells were examined using a confocal laser scanning microscope (CLSM). The FRET donor DOX was excited at 488 nm and fluorescence images were acquired in optical windows between 560-600 nm (DOX imaging channel) and 660-700 nm (Cy5 imaging channel).

The feasibility of using FRET to study the mechanism of drug release from DOX-loaded Cy5-NPCS NPs intracellularly was evaluated. Cells were incubated with test NPs for distinct durations and fluorescence images were then taken by CLSM in optical windows between 560-600 nm (DOX imaging channel) and 660-700 nm (Cy5 imaging channel) when irradiating NP suspensions at 488 nm. By 30 min after incubation, fluorescence indicative of NPCS NPs was observed in the Cy5 imaging channel, while no fluorescence was observed in the DOX imaging channel (not shown). After 1 hour, the intensity of Cy5 diminished significantly while a weak intensity of DOX fluorescence was observed in the cytosol (the second column), suggesting that the efficiency of FRET from DOX to Cy5 decreases relatively due to the swelling of NPs (thus an increase in the distance between DOX and Cy5). With time progressing (1-4 hour), the Cy5 fluorescence was not observed any more (the third column, FRET off), but the intensity of fluorescence seen in the DOX imaging channel became stronger, indicating that DOX was released significantly from Cy5-NPCS NPs into the cytosol. At 12 hours, DOX fluorescence was first located in the surrounding area of the cell nuclei (the fourth column) and then accumulated in the cell nuclei with time (at 24 hours after, the fifth column).

It has been shown that free DOX is localized in the cell nuclei within 30 min after incubation. In one example, a gradual accumulation of DOX in the cell nuclei was observed, suggesting that the release of DOX from Cy5-NPCS NPs was in a manner driven by the environmental pH in the acidic organelles. It is important to transport DOX into the nuclei to exert its cytotoxicity because its mechanism of action is to interact with DNA by intercalation and inhibition of macromolecular biosynthesis.

In one embodiment, the release of DOX from Cy5-NPCS NPs is pH dependent. After endocytosis, Cy5-NPCS NPs transiently localize in the caveolae/caveosomes wherein the release of DOX from NPs was not observed. Following Cy5-NPCS NPs trafficking into the acidic organelles, a significant release of DOX into the cytosol was noticed, due to the Cy5-NPCS conformational change triggered by the local pH values. The released DOX subsequently accumulates in the cell nuclei, exerting a considerable cytotoxicity. The aforementioned results indicate that we are able to use the FRET technique to intracellularly monitor and/or image the release of DOX from pH-responsive Cy5-NPCS NPs.

Some aspects of the invention relate to a pharmaceutical composition of nanoparticles, each nanoparticle comprising N-palmitoyl chitosan, a targeting moiety, and at least one anticancer agent. The anticancer agent include chemotherapeutic drug, wherein the majority of chemotherapeutic or anticancer drugs can be divided into alkylating agents, antimetabolites, anthracyclines, plant alkoloids, topoisomerase inhibitors, antimitotics, anticancer antibiotics, and other anti-tumor agents. These drugs affect cell division or DNA synthesis and function in some way. Some newer anticancer agents do not directly interfere with DNA. These anticancer agents include monoclonal antibodies and the new tyrosine kinase inhibitors, for example imatinib mesylate (Gleevec or Glivec), which directly targets a molecular abnormality in certain types of cancer (chronic myelogeneous leukemia, gastrointestinal stromal tumors). These are examples of targeted therapies that the pharmaceutical composition of nanoparticles of the present invention can be effective. In one embodiment, antineoplastic drugs inhibit and combat the development of cancer; they belong to a class of the anticancer agents of the invention.

Example No. 23

A Dual-Emission FRET Nanoprobe for Sensing/Imaging pH Changes in the Biological Environment Stimuli-responsive material is capable of probing environmental changes such as pH and temperature by detecting biological phenomena intracellularly or extracellularly. Intracellular pH is generally between 6.8 and 7.4 in the cytosol and between 4.5 and 6.0 in the cell's acidic organelles. When compared with conventional microelectrode techniques, fluorescent dyes provide an enhanced sensitivity required for optical pH measurements inside living cells and offer a greater spatial sampling capability. However, the optical change of fluorescent dyes is often relatively small and monotonous (in single-emission pattern), thus limiting their roles in probing intracellular pH changes. This highlights the need to develop improved fluorescent probes that can sense pH changes intracellularly. On the other hand, many pathological conditions such as cancers are associated with increased metabolic activity and hypoxia, resulting in an elevated extracellular acidity. Imaging acidic regions could provide valuable information about disease localization and progression and might enhance diagnosis and therapy. Therefore, developing a pH-responsive fluorescence probe able to detect variations in the environmental acidity is of significant interest.

Figure 27:
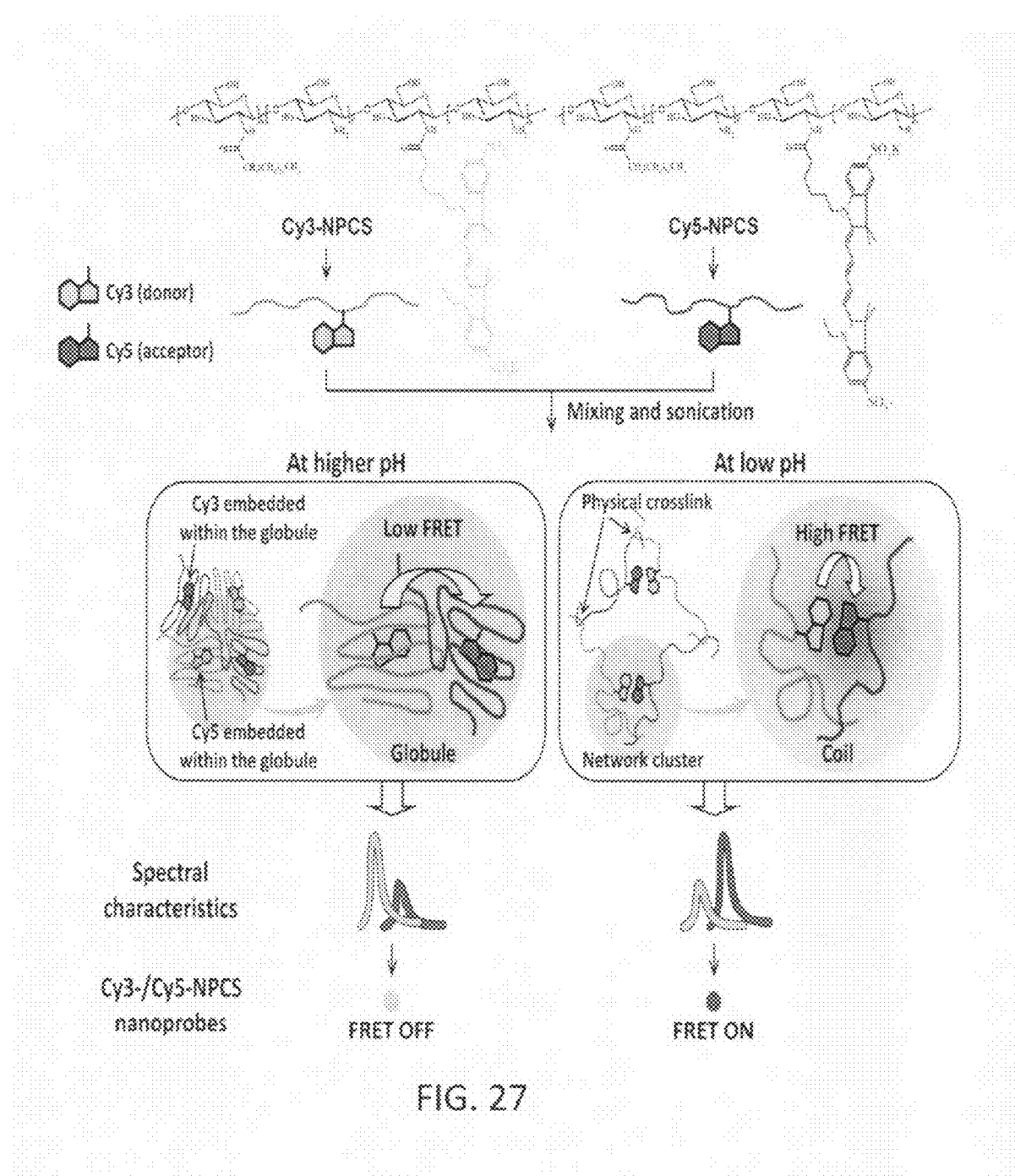
FIG. 27 shows the pH-responsive FRET nanoprobes. Schematic illustrations showing a dual-emission nanoprobe that can sense changes of the environmental pH, based on the concept of pH-responsive Förster resonance energy transfer (FRET) of a biocompatible polyelectrolyte, N-palmitoyl chitosan (NPCS), conjugated with a donor (Cy3) or an acceptor (Cy5) moiety.

Some aspects of the invention relate to a dual-emission nanoprobe that can sense changes of the environmental pH is developed based on the concept of pH-responsive Förster resonance energy transfer (FRET) of a biocompatible polyelectrolyte, N-palmitoyl chitosan (NPCS), conjugated with a donor (Cy3) or an acceptor (Cy5) moiety (FIG. 27). FRET involves the non-radiative transfer of energy from an excited state fluorophore (donor) to a second chromophore (acceptor) in a close proximity (less than 10 nm). FRET measurements offer a highly effective means of probing either molecular interactions or a single molecular event such as molecular cleavage and conformational transition of a protein, thus providing a platform to design a sensor molecule for detecting the variation in molecular environments. FRET imaging that allows the simultaneous recording of two emission intensities at different wavelengths in the presence or absence of analytes has provided a feasible approach for visualizing a complex biological process at the molecular levels. Therefore, developing dual-emission fluorescent probes provides ratiometric measurements of the emission intensities by modulating a FRET process.

Result from a Dual-Emission FRET Nanoprobe

As illustrated schematically in FIG. 27, NPCS is an associated polyelectrolyte characterized by the presence of alternating charges (protonated amine groups) and hydrophobic side chains (palmitoyl groups). NPCS in an aqueous environment exhibits a rapid nanostructure transformation within a narrow pH range through a proper balance between charge repulsion and hydrophobic interaction. In one embodiment, a tiny amount of Cy3 or Cy5 moiety is attached to the backbone of NPCS to yield Cy3-NPCS and Cy5-NPCS, respectively. The molar ratio of Cy3 or Cy5 to NPCS monomers was ca. 0.4%; therefore, a NPCS chain contained about one Cy3 or Cy5 group as estimated from the polymer molecular weight. Cy3-NPCS and Cy5-NPCS in equal amount are added into the aqueous solution with a prescribed pH to yield the solutions containing the mixture of these two species. It has been shown that the NPCS with a sufficiently high degree of substitution (DS, e.g. 15%) of palmitoyl group would form nanoscale network clusters [which will be called "nanoparticles (NPs)" hereafter] at low pH, where a fraction of the hydrophobic side chains associated to form micellar aggregates that act as the physical crosslinks tying NPCS chains to generate the network.

The NPCS chains between the physical crosslinks were highly expanded due to charge repulsion between the protonated amine groups on the backbone. Our quantitative analysis of the small angle X-ray scattering profile associated with these network clusters reveals that the characteristic mesh size of the network was in the order of 2 nm. As a result, in the network clusters containing both Cy3-NPCS and Cy5-NPCS chains, Cy3 and Cy5 moieties are well exposed to each other and their separation distance should be within the critical distance (about 10 nm) required for FRET. An energy transfer from Cy3 to Cy5 is hence expected to take place at a low pH. When pH is raised, the increase in hydrophobicity of NPCS arising from deprotonation of the amine groups induces the collapse of polymer chains into globules. Once the intrachain collapse dominates, Cy3 and Cy5 moieties will be embedded within the individual globules and hence become inaccessible to their counterpart for energy transfer. Consequently, the ability of NPCS to self-associate to form expanded network clusters offers the close proximity between the donor and acceptor moieties required for FRET, while the pH-driven conformational transition prescribes the on-to-off switch of the energy transfer.

NPCS was prepared by conjugating a hydrophobic palmitoyl group onto the free amine groups of chitosan (CS). CS, a natural-origin polysaccharide, is biodegradable, non-toxic and soft-tissue compatible, and thus has been used extensively in biomedical applications. The pH-triggered conformational transition was demonstrated by comparing the hydrodynamic radii ($R_h$) of NPCS with a DS of 15% (denoted as NPCS-15%) at pH 4.5 and 7.4 measured by dynamic light scattering at varying temperatures (not shown). It is noted that $R_h$ at pH 4.5 was always greater than that at pH 7.4 under a given temperature. At the physiological temperature (ca. 37° C.), for instance, $R_h$ at pH 4.5 was 145 nm as compared to 97 nm at pH 7.4. It is noted that the size of NPs measured was significantly larger than that expected for single polymer chains (at the order of several nm), thereby confirming that aggregates or clusters of NPCS were formed in aqueous media.

FIG. 26 shows the emission ratio of Cy5/Cy3 according to the FRET spectra of Cy3-/Cy5-NPCS-15% NP solutions, which were normalized to the maximum Cy3 donor peak around 570 nm, as a function of the environmental pH. All spectra were obtained by irradiating solutions at 520 nm corresponding to the excitation wavelength of the FRET donor, Cy3. As the environmental pH was changed, spectral changes were observed; sequential increases in the fluorescence emission ratio of Cy5/Cy3 were observed with decreased pHs. The increase in the emission ratio of Cy5/Cy3 was due to a higher FRET efficiency; that is, more energy transferred from Cy3 to Cy5 at lower pH.

The variation in the FRET efficiency with pH values was consistent with our postulated mechanism of the pH-triggered NPCS conformational change. This accordance implies that intrachain collapse of NPCS in the network clusters at higher pH should take place predominantly. In this case, Cy3 and Cy5 moieties were located at different globules such that their mutual interactions required for energy transfer was effectively shielded. If interchain collapse were the dominated mode, then a single globule would have contained both Cy3 and Cy5 moieties and hence energy transfer was still accessible. It is interesting to note that some Cy5 emission still existed at pH 8.0 (not shown). This may be due to the presence of some Cy3 and Cy5 groups at the surface of the collapsed aggregates, such that a small fraction of Cy3 moiety were still able to interact with Cy5 to induce the energy transfer.

It is noted that Cy3-/Cy5-NPCS with a DS of 15% represented the optimum prescription for attaining high FRET efficiency. NPCS with a lower DS was found to display lower FRET efficiency, given that the polymer chains could not form clusters effectively in aqueous media at lower pH due to a weaker hydrophobic interaction. In this case, a significant fraction of chains remained well dispersed and their large separation distance at low polymer concentration (100 μg/mL) frustrated the energy transfer from the Cy3 groups in a given chain to the Cy5 groups in others. On the other hand, the variation in size for the NPs prepared from NPCS with a DS larger than 15% became significant.

The aforementioned results suggest that the developed Cy3-/Cy5-labeled NPCS NPs can be used as a dual-emission nanoprobe for detecting variations in the environmental acidity, especially in the pH ranges of 7.5 to 4.0. Moreover, the environmental pH can be imaged from the ratio of signal intensity of Cy3 (FRET donor) and Cy5 (FRET acceptor) on NPCS via modulating a pH-responsive FRET process. Further, this technique was demonstrated in a cell model to access the possibility of using the developed Cy3-/Cy5-labeled NPCS NPs to probe, image or discriminate varied acidity of cellular organelles.

To elucidate their potential cellular uptake pathway, the interaction between NPCS-15% NPs (fluorescein-labeled) and cell membranes was investigated by treating cells (HT1080 human fibrosarcoma) with different chemical inhibitors and then analyzed by flow cytometry; the counterparts in the absence of inhibitors were used as controls. Chlorpromazine and wortmannin have been used as inhibitors for clathrin-mediated uptake and macropinocytosis, respectively. Treatment with chlorpromazine or wortmannin did not result in a significant inhibition of uptake of NPCS NPs, indicating that neither clathrin-mediated endocytosis nor macropinocytosis was involved in the endocytosis. Methyl-β-cyclodextrin (MβCD) and genistein are known to inhibit caveolae-mediated endocytosis, each acting by a different mechanism. As compared to the control, cells treated with MβCD or genistein significantly diminished the fluorescence intensity, an indication of caveolae-mediated endocytosis. The aforementioned results suggest that the caveolae-mediated pathway played a significant role in the internalization of NPCS NPs.

Caveolae are characterized by the presence of a family of caveolin proteins including caveolin-1 (CAV1). To further support the entry of NPCS NPs via the caveolae-mediated pathway, the potential co-localization of CAV1 and test NPs during and after entry into cells was investigated. NPCS NPs were initially observed in cell membranes and co-localized with CAV1 (caveolae marker, at 15 min after incubation). The internalized NPs were found associated with CAV1-positive structures (caveosomes, at 30 min after) near the cell periphery. Subsequently, significant levels of NPs were found colocalized with early endosomes (EEA1, at 1 hour after); the early endosomes then matured into late endosomes, and then to lysosomes at longer incubation time points (1 hour to 4 hours, LAMP2). These data demonstrate that following the caveolar endocytosis, NPCS NPs traffic within early endosomes, which mature into acidic late endosomes and lysosomes. One aspect of the invention relate to using the prepared fluorescent (Cy3-/Cy5-labeled) NPCS NPs to probe the intracellular acidic organelles (early endosomes, late endosomes and lysosomes).

Variations in the intracellular acidity can be further evaluated using the ratio of the signal intensities of Cy5 to Cy3 imaging channels analyzed by ZEN 2009 Light Edition Software. The Cy5/Cy3 emission ratio in cells varied with time after the internalization of test NPs. With time increasing, stimulated by the decrease in intracellular pH, an increase in the Cy5/Cy3 emission ratio was observed, an indication of a higher FRET efficiency. The higher FRET efficiency seen in a lower pH environment was induced by the pH-triggered NPCS conformational change as discussed above. The aforementioned results demonstrate that the developed Cy3-/Cy5-labeled NPCS NPs can be used effectively as a ratiometric fluorescent pH-sensor for probing the acidity of endocytic organelles in live cells. This feature is advantageous over the traditional fluorescent acidotropic probe (LysoTracker), which can only display a monotonous color and is therefore not able to distinguish the variation in environmental pH in intracellular organelles.

Some aspects of the invention relate to a sensitive and practical means for the detection of environmental pH changes in locating intracellular acidic organelles and acidified morbid tissues via FRET, which is a powerful technique in optical imaging. It substantially improves the performance of the conventional florescence-based probes, which display merely single-emission patterns with a modest change in fluorescence intensity when responding to the environmental stimuli. A few FRET-based pH sensing methods, including conjugating/entrapping a pH-sensitive fluorescent dye on quantum dots or in nanogels, have been reported in the literature; however, their pH sensitive capacity is limited to 6.0-8.0, thus restricting their biological applications below pH 6.0.

To address this concern, we develop a dual-emission FRET nanoprobe made of NPCS for sensing pH changes in the biological environment. With the modulation of their conformational transition in response to the environmental pH changes, the gradual alteration in accessibility of the donor (Cy3) to the acceptor (Cy5) on NPCS for energy transfer contributes to different FRET efficiencies. This conformational transition enables the developed NPCS nanoprobe functioning as a pH sensor in the range of 4.0-7.5, which is suitable for monitoring the pH changes intracellularly and extracellularly. Additionally, the developed pH-responsive nanoprobe can be used to produce ratiometric images and thus discriminate the variation in environmental pH at different length scales examined by IVIS or CLSM. Some aspects of the invention relate to a NPCS nanoprobe for sensing the pH in a range of pH 4.0 to 7.5 intracellularly or extracellularly, wherein the nanoprobe comprises a donor (for example Cy3) and an acceptor (for example Cy5) for energy transfer. In one embodiment, the energy transfer follows the Förster resonance energy transfer (FRET) principle.

Choosing specific fluorophores (donor and acceptor) for FRET-based imaging probes must consider their respective excitation and emission ranges. In our approach, several FRET pairs, not limited by fluorophore wavelengths, may be used to conjugate on NPCS to perform the energy transfer in response to their underlying conformation transition in mapping the environmental pH changes based on the needed experimental conditions for biological applications.

Some aspects of the invention relate to a dual-emission pH-responsive nanoprobe made of Cy3-/Cy5-labeled NPCS NPs. The change from a weakly charged, globule construction at high pH to a highly charged, expanded coil structure in the network clusters formed at low pH enables the prepared NPs to act as a simple switch off (suppress FRET) or on (gain FRET) in response to changes in the environmental pH, thus may be used to probe the intracellular acidic organelles such as early/late endosomes and lysosomes. Additionally, this technique may have the potential to localize diseases involving environmental pH changes and hence facilitates diagnosis and therapy.

Dual-emission images of fluorescent NP suspensions at distinct pH environments were acquired using an In Vivo Imaging System (IVIS, Xenogen, Alameda, Calif., USA). In the study, Cy3-/Cy5-labeled NP suspensions (100 µg/mL, 200 µL per well) were loaded in a 96-well plate. The plate was irradiated at a wavelength of 535±15 nm and then imaged with sequential emission filters (580±10 nm and 680±10 nm bandpass) to obtain unmixed Cy3 and Cy5 images. The composite images of unmixed Cy3 and Cy5 images were then processed using the Living Imaging® 3.0 Software.

Mapping Spatial pH Changes in Living Cells

To perform the intracellular fluorescence ratiometric imaging, cells were treated with Cy3-/Cy5-labeled NPs as per the procedure used in the intracellular trafficking study. The FRET donor Cy3 was excited at 543 nm and fluorescence images were monitored in a Cy3 imaging channel (560-600 nm) and a Cy5 imaging channel (660-700 nm). The corresponding pseudocolored ratio images were obtained by analyzing the ratio of the signal intensities of Cy5 to Cy3 imaging channels using ZEN 2009 Light Edition Software.

Some aspects of the invention relate to a pharmaceutical composition of nanoparticles, each nanoparticle comprising N-palmitoyl chitosan, a targeting moiety, and at least one anticancer agent. In one embodiment, the targeting moiety is conjugated onto the N-palmitoyl chitosan as illustrated in FIG. 20a. In one embodiment, the anticancer agent is a chemotherapy component. In another embodiment, the anticancer agent is doxorubicin (DOX), cyclophosphamide, paclitaxel, adriamycin, cisplatin, or 5-fluorouracil. In still another embodiment, the anticancer agent is selected from the group consisting of alkylating agents, antimetabolites, anthracyclines, plant alkoloids, topoisomerase inhibitors, antimitotics, and anticancer antibiotics. In one embodiment, the nanoparticles are adapted for delivery to a blood vessel of an animal subject. In one embodiment, the targeting moiety is galactosamine or Cy5.

Some aspects of the invention relate to A pH-responsive Förster resonance energy transfer (FRET) nanoprobe for sensing a change of environmental pH, wherein the nanoprobe comprises N-palmitoyl chitosan (NPCS) that is conjugated with a pair of donor moiety and an acceptor moiety. In one embodiment, the donor moiety is Cy3 and the acceptor moiety is Cy5.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A composition of nanoparticles, wherein each nanoparticle comprises N-palmitoyl chitosan (NPCS) that is conjugated with at least two different moieties, said moieties including a donor moiety and an acceptor moiety having a distance of 10 nm or less between said donor moiety and said acceptor moiety that enables Förster resonance energy transfer.

2. The composition of claim 1, wherein the donor moiety is an anticancer agent.

3. The composition of claim 2, wherein the anticancer agent is doxorubicin (DOX) or cyclophosphamide.

4. The composition of claim 2, wherein said anticancer agent is paclitaxel.

5. The composition of claim 2, wherein said anticancer agent is a chemotherapy component.

6. The composition of claim 2, wherein said anticancer agent is adriamycin, cisplatin, or 5-fluorouracil.

7. The composition of claim 2, wherein said anticancer agent is selected from the group consisting of alkylating agents, antimetabolites, anthracyclines, plant alkoloids, topoisomerase inhibitors, antimitotics, and anticancer antibiotics.

8. The composition of claim 2, wherein said acceptor moiety is Cy5 to form anticancer agent-loaded Cy5-NPCS nanoparticles.

9. The composition of claim 8, wherein said anticancer agent-loaded Cy5-NPCS nanoparticles are characterized with enhanced intracellular localization and anticancer agent release.

10. The composition of claim 1, wherein said acceptor moiety is galactosamine.

11. The composition of claim 1, wherein said acceptor moiety is Cy5.

12. The composition of claim 1, wherein said nanoparticles are adapted for delivery to a blood vessel of an animal subject.

13. The composition of claim 1, wherein the donor moiety is Cy3.

14. The composition of claim 13, wherein the acceptor moiety is Cy5.

15. The composition of claim 14, wherein said nanoparticles are adapted for sensing a change of an environmental pH intracellularly or extracellularly.

16. The composition of claim 15, wherein said change of an environmental pH is in the range of 4.0-7.5.

17. The composition of claim 14, wherein said nanoparticles are adapted for discriminating varied acidity of cellular organelles.

* * * * *